(12) United States Patent
Tisone et al.

(10) Patent No.: US 7,470,547 B2
(45) Date of Patent: Dec. 30, 2008

(54) METHODS AND SYSTEMS FOR DISPENSING SUB-MICROFLUIDIC DROPS

(75) Inventors: Thomas C. Tisone, Orange, CA (US); Michelle Rodriquez, Mission Viejo, CA (US); Michael K. Cabourne, Fullerton, CA (US)

(73) Assignee: Biodot, Inc., Irvine, CA (US)

( * ) Notice: Subject to any disclaimer, the term of this patent is extended or adjusted under 35 U.S.C. 154(b) by 840 days.

(21) Appl. No.: 10/909,934

(22) Filed: Aug. 2, 2004

(65) Prior Publication Data

US 2005/0056713 A1    Mar. 17, 2005

Related U.S. Application Data

(60) Provisional application No. 60/561,045, filed on Apr. 9, 2004, provisional application No. 60/560,860, filed on Apr. 9, 2004, provisional application No. 60/491,613, filed on Jul. 31, 2003.

(51) Int. Cl.
*G01N 1/10* (2006.01)
*B01L 3/02* (2006.01)

(52) U.S. Cl. .................. 436/180; 422/100; 73/863.32; 73/864; 239/690.1

(58) Field of Classification Search .............. 422/100; 436/180; 73/863.32, 864; 239/690.1
See application file for complete search history.

(56) References Cited

U.S. PATENT DOCUMENTS

| 2,264,564 A | 12/1941 | Connor |
| 2,512,743 A | 6/1950 | Hansell |
| 3,373,437 A | 3/1968 | Sweet et al. |
| 3,452,360 A | 6/1969 | Williamson |
| 3,512,173 A | 5/1970 | Damouth |
| 3,946,398 A | 3/1976 | Kyser et al. |
| 4,018,383 A | 4/1977 | Paton et al. |
| 4,121,466 A | 10/1978 | Reichler et al. |
| 4,199,013 A | 4/1980 | Reich et al. |
| 4,223,558 A | 9/1980 | Schmider et al. |
| 4,278,205 A | 7/1981 | Binoche |
| 4,369,664 A | 1/1983 | Bunce et al. |
| 4,478,094 A | 10/1984 | Salomaa et al. |
| 4,492,322 A | 1/1985 | Hieftje et al. |
| 4,555,957 A | 12/1985 | Frankel et al. |
| 4,681,742 A | 7/1987 | Johnson et al. |
| 4,717,049 A | 1/1988 | Green et al. |
| 4,748,043 A | 5/1988 | Seaver et al. |
| 4,877,745 A | 10/1989 | Hayes et al. |
| 4,922,852 A | 5/1990 | Price |
| 4,926,701 A | 5/1990 | Tompkins |
| 4,944,922 A | 7/1990 | Hayashi |
| 5,004,159 A | 4/1991 | Kistner |

(Continued)

FOREIGN PATENT DOCUMENTS

EP    0 810 438 A2    12/1997

(Continued)

*Primary Examiner*—Brian R. Gordon
(74) *Attorney, Agent, or Firm*—Knobbe, Martens, Olson & Bear, LLP

(57) ABSTRACT

The invention relates generally to dispensing of fluids and, in particular, to methods and systems for dispensing microfluidic or sub-microfluidic volumes of droplets of chemical, biological or other reagents or liquids. Embodiments of the invention have particular efficacy in accurately dispensing small drops having volumes from about 100 nL down into the picoliter range.

76 Claims, 29 Drawing Sheets

U.S. PATENT DOCUMENTS

| | | | |
|---|---|---|---|
| 5,041,266 A | 8/1991 | Fox | |
| 5,056,462 A | 10/1991 | Perkins et al. | |
| 5,132,097 A | 7/1992 | Van Deusen et al. | |
| 5,320,250 A | 6/1994 | La et al. | |
| 5,324,480 A | 6/1994 | Shumate et al. | |
| 5,334,353 A | 8/1994 | Blattner | |
| 5,338,688 A | 8/1994 | Deeg et al. | |
| 5,486,337 A * | 1/1996 | Ohkawa | 422/100 |
| 5,505,777 A | 4/1996 | Ciardella et al. | |
| 5,509,966 A | 4/1996 | Sykes | |
| 5,525,515 A | 6/1996 | Blattner | |
| 5,529,756 A | 6/1996 | Brennan | |
| 5,542,289 A | 8/1996 | Hool et al. | |
| 5,558,838 A | 9/1996 | Uffenheimer | |
| 5,593,839 A | 1/1997 | Hubbell et al. | |
| 5,593,893 A | 1/1997 | Kobashi et al. | |
| 5,601,980 A | 2/1997 | Gordon et al. | |
| 5,601,982 A | 2/1997 | Sargent et al. | |
| 5,621,443 A | 4/1997 | Buschulte et al. | |
| 5,636,788 A | 6/1997 | Wilson | |
| 5,658,802 A | 8/1997 | Hayes et al. | |
| 5,707,588 A * | 1/1998 | Tsukishima | 422/99 |
| 5,711,989 A | 1/1998 | Ciardella et al. | |
| 5,738,728 A | 4/1998 | Tisone | |
| 5,741,554 A | 4/1998 | Tisone | |
| 5,742,304 A | 4/1998 | Richtsmeier et al. | |
| 5,743,960 A | 4/1998 | Tisone | |
| 5,744,305 A | 4/1998 | Fodor et al. | |
| 5,747,102 A | 5/1998 | Smith et al. | |
| 5,750,881 A | 5/1998 | Dorenkott et al. | |
| 5,756,050 A | 5/1998 | Ershow et al. | |
| 5,763,278 A | 6/1998 | Sickinger et al. | |
| 5,770,151 A | 6/1998 | Roach et al. | |
| 5,770,160 A | 6/1998 | Smith et al. | |
| 5,807,522 A | 9/1998 | Brown et al. | |
| 5,811,306 A | 9/1998 | Komatsu | |
| 5,853,894 A | 12/1998 | Brown | |
| 5,886,716 A | 3/1999 | Heinzl et al. | |
| 5,916,524 A | 6/1999 | Tisone | |
| 5,925,732 A | 7/1999 | Ecker et al. | |
| 5,927,547 A | 7/1999 | Papen et al. | |
| 5,958,342 A | 9/1999 | Gamble et al. | |
| 5,967,202 A | 10/1999 | Mullen et al. | |
| 5,985,214 A | 11/1999 | Stylli et al. | |
| 5,999,949 A | 12/1999 | Crandall | |
| 6,044,212 A | 3/2000 | Flavin et al. | |
| 6,063,339 A | 5/2000 | Tisone et al. | |
| 6,083,762 A | 7/2000 | Papen et al. | |
| 6,100,030 A | 8/2000 | McCasky Feazel et al. | |
| 6,103,479 A | 8/2000 | Taylor | |
| 6,114,178 A | 9/2000 | Dezael et al. | |
| 6,121,048 A | 9/2000 | Zaffaroni et al. | |
| 6,143,252 A | 11/2000 | Haxo, Jr. et al. | |
| 6,150,173 A | 11/2000 | Schubert | |
| 6,203,759 B1 | 3/2001 | Pelc et al. | |
| 6,220,075 B1 | 4/2001 | Papen et al. | |
| 6,225,061 B1 | 5/2001 | Becker et al. | |
| 6,485,690 B1 | 11/2002 | Pfost et al. | |
| 6,537,505 B1 | 3/2003 | LaBudde et al. | |
| 6,548,263 B1 | 4/2003 | Kapur et al. | |
| 6,551,557 B1 | 4/2003 | Rose et al. | |
| 6,576,295 B2 | 6/2003 | Tisone | |
| 6,589,791 B1 | 7/2003 | LaBudde et al. | |
| 6,599,479 B1 | 7/2003 | Kietzmann et al. | |
| RE38,281 E * | 10/2003 | Tisone | 422/100 |
| 6,710,335 B2 * | 3/2004 | Ellson et al. | 250/288 |
| 6,713,021 B1 * | 3/2004 | Shvets et al. | 422/100 |
| 6,797,945 B2 * | 9/2004 | Berggren et al. | 250/288 |
| 6,816,742 B2 | 11/2004 | Kim et al. | |
| 6,838,051 B2 | 1/2005 | Marquiss et al. | |
| 6,995,024 B2 * | 2/2006 | Smith et al. | 436/180 |
| 7,179,423 B2 * | 2/2007 | Bohm et al. | 422/100 |
| 7,211,223 B2 * | 5/2007 | Fouillet et al. | 422/100 |
| 7,312,068 B2 * | 12/2007 | Pinkel et al. | 435/287.2 |
| 7,332,347 B2 * | 2/2008 | Li et al. | 436/177 |
| 2001/0014477 A1 | 8/2001 | Pelc et al. | |
| 2001/0016177 A1 | 8/2001 | Pelc et al. | |
| 2001/0036424 A1 | 11/2001 | Takahashi et al. | |
| 2002/0001675 A1 | 1/2002 | Tisone | |
| 2002/0064482 A1 | 5/2002 | Tisone et al. | |
| 2002/0092366 A1 * | 7/2002 | Brock et al. | 73/863.32 |
| 2002/0151085 A1 * | 10/2002 | Zaffaroni et al. | 436/180 |
| 2002/0158027 A1 * | 10/2002 | Moon et al. | 210/756 |
| 2002/0159919 A1 | 10/2002 | Churchill et al. | |
| 2002/0168297 A1 * | 11/2002 | Shvets et al. | 422/100 |
| 2003/0148538 A1 * | 8/2003 | Ng | 436/180 |
| 2003/0175163 A1 * | 9/2003 | Shvets et al. | 422/100 |
| 2003/0207464 A1 | 11/2003 | Lemmo et al. | |
| 2003/0215957 A1 | 11/2003 | Lemmo et al. | |
| 2003/0228241 A1 | 12/2003 | Legge | |
| 2004/0009611 A1 * | 1/2004 | Williams et al. | 436/180 |
| 2004/0091398 A1 * | 5/2004 | Gilbert et al. | 422/100 |
| 2004/0265185 A1 * | 12/2004 | Kitagawa | 422/100 |
| 2005/0003458 A1 | 1/2005 | Moore et al. | |
| 2005/0232823 A1 * | 10/2005 | Brock et al. | 422/100 |
| 2006/0211132 A1 * | 9/2006 | Miledi et al. | 436/180 |
| 2006/0263264 A1 * | 11/2006 | Bohm et al. | 422/100 |

FOREIGN PATENT DOCUMENTS

| | | |
|---|---|---|
| EP | 0 990 528 A2 | 4/2000 |
| EP | 0 990 528 A3 | 4/2000 |
| EP | 1 099 484 A1 | 5/2001 |
| EP | 1 128 310 A2 | 8/2001 |
| EP | 1 128 310 A3 | 8/2001 |
| EP | 1 179 364 A2 | 2/2002 |
| EP | 1 179 368 A2 | 2/2002 |
| EP | 1 179 368 A3 | 10/2002 |
| EP | 1 179 364 A3 | 2/2003 |
| EP | 1 658 894 A1 | 5/2006 |
| WO | WO 97/44134 | 11/1997 |
| WO | WO 99/30168 A1 | 6/1999 |
| WO | WO 99/42752 | 8/1999 |
| WO | WO 99/42804 | 8/1999 |
| WO | WO 03/072258 A1 | 9/2003 |

* cited by examiner

*Helium Pressurize*

*Pump Fill*

*Dispense*

*Electrostatic Dispense Field*

*Electrostatic Dispense Field*

*Electrostatic Dispense Field*

*Taylor Field*

*Electrostatic Dispense Field with Ionizer*

Tip Detail

Tip Detail

Helium Pressurize

*Pump Fill*

*Dispense*

Electrostatic Dispense Field

Electrostatic Dispense Field

Electrostatic Dispense Field

*Electrostatic Dispense Field with Ionizer*

METHODS AND SYSTEMS FOR DISPENSING SUB-MICROFLUIDIC DROPS

RELATED APPLICATIONS

This application claims the benefit of U.S. Provisional Application No. 60/491,613, filed Jul. 31, 2003, entitled METHODS AND SYSTEMS FOR DISPENSING SUB-MICROFLUIDIC DROPS, U.S. Provisional Application No. 60/561,045, filed Apr. 9, 2004, entitled LIQUID DISPENSING SYSTEM WITH HELIUM SPARGER DEGASSING AND ELECTROSTATIC BIAS, and U.S. Provisional Application No. 60/560,860, filed Apr. 9, 2004, entitled PULSED POSITIVE DISPLACEMENT MICROFLUIDIC LIQUID DISPENSING SYSTEM WITH ELECTROSTATIC BIAS, the entirety of each one of which is hereby incorporated by reference herein.

BACKGROUND OF THE INVENTION

1. Field of the Invention

The invention relates generally to dispensing of fluids and, in particular, to methods and systems for dispensing microfluidic or sub-microfluidic volumes of droplets of chemical, biological or other reagents or liquids.

2. Description of the Related Art

Both genomics and proteomics involve the handling, transfer and assaying of microfluidic and sub-microfluidic quantities of expensive reagents and other liquids. Microfluidic liquid handling is associated with areas such as DNA microarraying, protein crystallization, high-throughput screening and combinatorial chemistry, among others. It has application in key markets such as life science research, biodiagnostics, pharmaceutical, agrochemical and materials science, among others.

It can be a difficult task to precisely, accurately and efficiently handle, transfer and deliver accurate microfluidic and sub-microfluidic quantities of liquids. These quantities typically are in the range from the order of a nanoliter (nL) to tens of microliters (μL) though they may be smaller, such as in the picoliter range, or larger.

The complexity of the task is further increased when dealing with a wide variety of reagents, complex target geometries or configurations and when dispense volumes are of the order of a hundred nanoliters or less. Conventional technologies are generally unable to address these issues adequately.

SUMMARY OF THE INVENTION

The invention relates generally to dispensing of fluids and, in particular, to methods and systems for dispensing microfluidic or sub-microfluidic volumes of droplets of chemical, biological or other reagents or liquids. Embodiments of the invention have particular efficacy in accurately dispensing small drops having volumes from about 100 nL down into the picoliter range. In one embodiment, the drops have a volume in the range from about 1 nL to about 100 nL, including all values and sub-ranges therebetween.

Some embodiments provide a method of accurately dispensing sub-microfluidic droplets of a reagent. The method generally comprises providing a dispenser connected to a dispensing tip having a nozzle and a droplet emitting orifice at a distal end. An electric field is generated between the tip and an alignment member so that an electric field gradient is created substantially parallel to the intended droplet trajectory. The dispenser is actuated to dispense one or more droplets of a reagent into or onto a target.

Some embodiments provide a method of accurately dispensing sub-microfluidic droplets of a reagent onto or onto a target supported on a table. The method generally comprises providing a dispensing system comprising a substantially inert fluid path and a dispensing tip having a nozzle and a droplet emitting orifice at a distal end. An electric field is generated between the tip and the table by maintaining the tip at a first potential and the table at a second potential. The reagent is positively displaced through the tip to dispense droplets onto or into the target with the electric field providing a bias that facilitates droplet ejection and release from the tip so that droplets having a volume of less than about one microliter are reliably dispensed.

Some embodiments provide a method of accurately dispensing sub-microfluidic droplets of a reagent. The method comprises generally comprises pressurizing a reservoir containing a reagent to a degassing high first pressure by providing a static pressure from a helium source over the reagent to degas the reagent. The first pressure in the reservoir is reduced to a low second pressure. The reservoir is vented to ambient conditions. A pump connected to the reservoir is operated to draw the reagent from the reservoir into the pump. A tip having a dispense nozzle and a through lumen is provided with the tip being connected to the pump. A predetermined quantity of the reagent is metered from the pump to the tip to dispense one or more droplets of the reagent from the nozzle onto or into a target.

Some embodiments provide an apparatus for dispensing droplets of a reagent on a target that is not easily accessible. The apparatus generally comprises a dispenser, a positive displacement pump and a dispense tip. The dispenser has an inlet and an outlet and a valve adapted to be opened and closed at a predetermined frequency and duty cycle. The positive displacement pump is hydraulically arranged in series with the inlet of the dispenser for metering predetermined quantities of a reagent to the dispenser. The dispense tip is connected to the outlet of the dispenser to eject droplets of the reagent onto or into a substrate target. The dispense tip generally comprises a first conduit, a second conduit and a shaped surface. The first conduit originates at the outlet end of the dispenser and extends away from the outlet end of the dispenser. The first conduit has a first axis. The second conduit extends to form a droplet emitting orifice and is in fluid communication with the first conduit at a common junction. The second conduit has a second axis angled relative to the first axis. The shaped surface is proximate to the junction between the conduits to direct the reagent from the first conduit towards the orifice.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which.

DETAILED DESCRIPTION OF THE PREFERRED EMBODIMENTS

Figure 1:
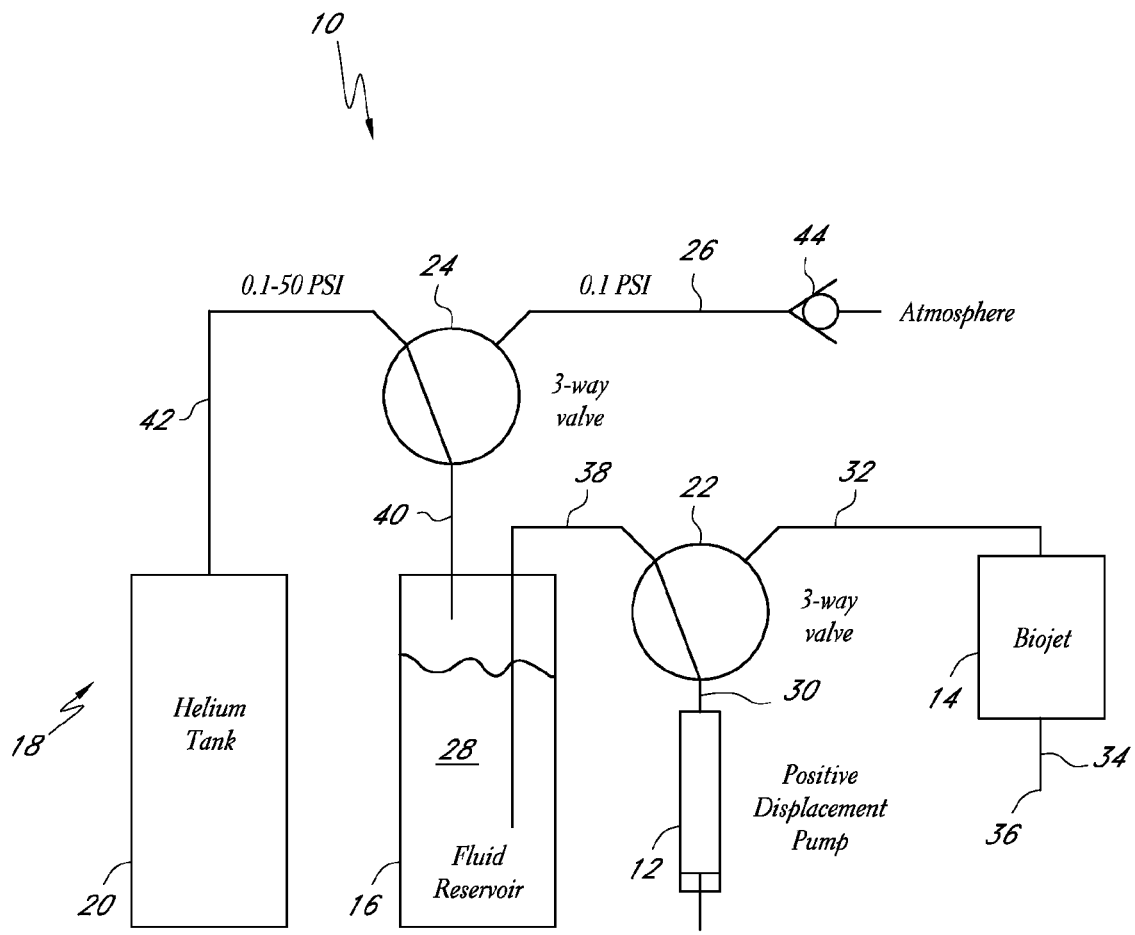
FIG. 1 is a simplified schematic view of a dispensing system including a static helium pressure system and illustrating a reservoir pressurization configuration having features and advantages in accordance with one embodiment of the invention.

The preferred embodiments of the invention described herein relate generally to dispensing of microfluidic or sub-microfluidic volumes of droplets of chemical, biological or other reagents or liquids and, in particular, to methods and systems for precisely and accurately dispensing liquid droplets having volumes less than about 100 nL and dispensing droplets in geometrically constrained target zones.

While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Embodiments of the invention have utility in a wide range of areas, applications and markets where handling, transfer and delivery of microfluidic or sub-microfluidic quantities of liquids is utilized. These include biotechnology and industrial uses, among others.

Examples include, but are not limited to, DNA microarraying, protein crystallization, combinatorial chemistry, high throughput screening (HTS), drug discovery, life science, diagnostics, pharmaceutical, medical, agrochemical and material science, among others. Other industrial examples include, but are not limited to, laser welding, adhesives, electronics and semiconductors, among others.

Embodiments of the invention can be used to dispense drops and form arrays on a wide variety of surfaces or substrates. These include, but are not limited to, membranes, glass or glass slides, microtiter plates, diagnostic strips, biochips, DNA-chips, gene-chips and special medical devices, among others. The substrates may have specialized surfaces depending on the particular application.

Advantages of small sub-microfluidic drops include lower cost since the dispensed reagents or other liquids can be expensive. Another advantage is that smaller drops can provide improved properties such as thermodynamic properties which may be useful to a particular application or use.

In one embodiment, the dispensed drop size is less than about 100 nL. In another embodiment, the dispensed drop size is in the range from about 100 nL to about 2,000 nL, including all values and sub-ranges therebetween.

Dispensing Systems with Actuator

Some dispensing and aspirating systems are disclosed in U.S. Pat. Nos. RE38,281 E, reissued Oct. 21, 2003, entitled DISPENSING APPARATUS HAVING IMPROVED DYNAMIC RANGE, and 6,063,339, issued May 16, 2000, entitled METHOD AND APPARATUS FOR HIGH-SPEED DOT ARRAY DISPENSING, the entirety of each one of which is hereby incorporated by reference herein. These patents disclose, among other things, a non contact dispensing system based on a positive displacement pumped solenoid dispenser or actuator. This system is capable of delivering individual drop sizes in the range of nanoliters up to microliters.

In this system, precise volumes of liquid are metered to the upstream side of a dispense solenoid valve, creating a low but positive fluid pressure. At coordinated time periods, the solenoid valve allows a subsequent release of fluid by the solenoid valve at the distal end. Upon exiting the solenoid, the fluid generally passes through a cylindrical conduit, which is coupled to an emitting orifice where upon drops of liquid are ejected. In this system, the solenoid valve, outlet fluid conduit, emitting orifice and ejected drops often share a common axis.

For drops having a volume below 100 nL and production applications with long duty cycles several problems can arise. One is an air bubble build up in the fluid lines due to precipitation of air from the liquid solution. Another is a build up of fluid droplets on the dispense nozzle surface which can interfere with the drop release from the nozzle tip. The build up of fluid droplets on the dispense nozzle surface can also be caused by the air bubbles passing through the ejection orifice and bursting to undesirably force fluid around the nozzle tip and cause ejection of unwanted satellite drops.

In the diagnostic and drug discovery markets there is a growing need to dispense drops down into the 1 nL range. Utilizing the solenoid actuated dispense systems of U.S. Pat. Nos. RE38,281 E and 6,063,339, feasibility for 1 nL and below drop dispensing has been demonstrated in a laboratory environment but not with sufficient stability to be suitable as a commercial product.

In addition to the drop release issues, with small drops (order of 1 nL), electrostatic deflection of the drops becomes an increasingly more important issue. Many target substrates tend to be dielectric and hence build up static charge that can produce electric fields strong enough to deflect the drops in flight.

Vacuum degassing can be used to prevent or reduce undesirable air bubbles within the liquid. The vacuum degassing involves applying a vacuum or reduced pressure to the reagent-containing reservoir so that dissolved gases precipitate as gas bubbles. In addition, ultrasonic stimulation can be applied to accelerate the precipitation of gas bubbles. Hence, the reagent withdrawn by the positive displacement pump will have reduced levels of dissolved gas.

One of the problems with the use of this vacuum degassing system is that it needs to be turned off when the syringe positive displacement system is pumping fluid from the degassed reservoir. Thus, disadvantageously, a mechanism is needed to turn the vacuum on and off during operation of the dispenser and hence the vacuum degasser becomes a relatively complicated solution to the degassing problem. It also becomes even more complicated and expensive if more than one reagent reservoir is being used in conjunction with a single dispensing machine.

Another issue with vacuum degassing is that when the vacuum is removed, atmospheric gases will quickly redissolve in the fluid hence this method is limited in how low the gas concentration can be reduced in the fluid during the machine operation. There is also a limit to how low a vacuum can be maintained with the fluid.

In some instances, the drops being dispensed often meet geometric constraints where the target zone is inaccessible because of the size of the dispensing device. In many product applications, this can force compromises in both product and dispenser design. This issue is not easily rectified by simply scaling down the size of existing technology.

Embodiments of the invention overcome one or more of the above disadvantages. Some embodiments provide a helium sparging degassing system and improve the quality of degassing of one or more reagent reservoirs. Some embodiments provide improved drop release from the nozzle tip for small drops (about 100 nanoliters down to the picoliter range).

Some embodiments provide an electric field generator to substantially eliminate or mitigate undesirable electrostatic deflections of small drops. Some embodiments provide an electric field generator to facilitate ejection of small drops (about 100 nanoliters down to the picoliter range) by providing an electrostatic bias. Some embodiments provide an electric field generator to control the droplet impact velocity.

Some embodiments provide ionized air flow over the dispense nozzles to control static charge. Some embodiments utilize a transverse dispensing tip configuration allow for ejecting drops at right angles to the conventional liquid flow path, thereby allowing entry into small dispense target zones.

The degassing embodiments provide several advantages. One advantage is reduced air in the hydraulic fluid lines. Another advantage is improved drop release. Yet another advantage is the elimination or reduction of bubble explosions, which is one source of satellites and fluid accumulation on the nozzles. A further advantage is improved dispensing robustness at small drop volumes from 100 nL down into the picoliter range.

The electric field embodiments provide several advantages. These include improved control of the drop trajectory to the substrate and facilitation of drop ejection. Another advantage is addition of an electrostatic deformation of the fluid meniscus to aid in the drop release of small volume drops from 100 nL down into the picoliter range. Yet another advantage is reduction of residual fluid on the nozzle surface in proximity to the tip orifice. The electric field embodiments may be used in conjunction with both pneumatically as well as hydraulically driven dispensers.

The dispense nozzle static control embodiments have several advantages. One advantage is reduction of residual fluid on the nozzle surface in proximity to the tip orifice. Another advantage is reduction in charging of substrates. The static control embodiments may be used in conjunction with both pneumatically as well as hydraulically driven dispensers.

The transverse drop emitting tip configurations provide several advantages. One advantage is enhanced droplet formation at the dispense orifice. Another advantage is the ability to dispense droplets at a predetermined angle to the main outlet fluid flow path.

In one embodiment, the dispensed droplets have a volume of about 1 nanoliters (nL). In another embodiment, the dispensed droplets have a volume in the range from about 0.5 nL to about 2 nL, including all values and sub-ranges therebetween. In yet another embodiment, the dispensed droplets have a volume in the range from about 0.25 nL to about 10 nL, including all values and sub-ranges therebetween. In still another embodiment, the dispensed droplets have a volume in the range from about 0.1 nL to about 100 nL, including all values and sub-ranges therebetween. In a further embodiment, the dispensed droplets have a volume less than about 100 nL.

Degassing

The degassing methods and systems disclosed, taught or suggested herein can be used in conjunction with any of the embodiments disclosed, taught or suggested herein. In some embodiments, and as discussed further below, helium sparging is used for efficient degassing of the reagent or liquid.

In one embodiment, the helium sparging involves substantially continuously bubbling helium gas through the reagent. This approach may be suitable for several types of reagents but may not be compatible with certain types of reagents such as reagents with certain types of surfactants and proteins. The bubbling action can cause foaming of some types of fluids, particularly those fluids with surfactants. The foaming can cause organic molecules to be torn apart on the surface of the foam bubbles, that is, protein denaturing.

Figure 2:
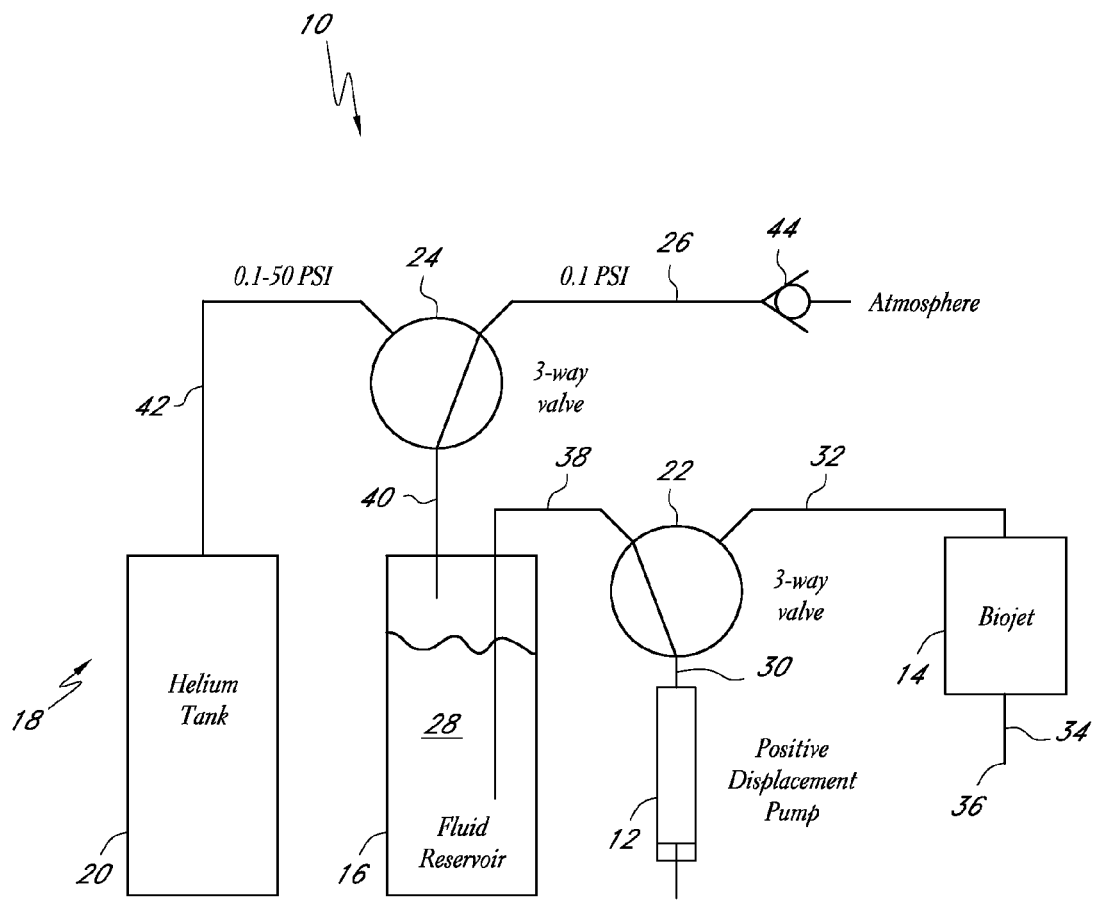
FIG. 2 is a simplified schematic view of the dispensing system of FIG. 1 illustrating a pump filling configuration having features and advantages in accordance with one embodiment of the invention.
Figure 3:
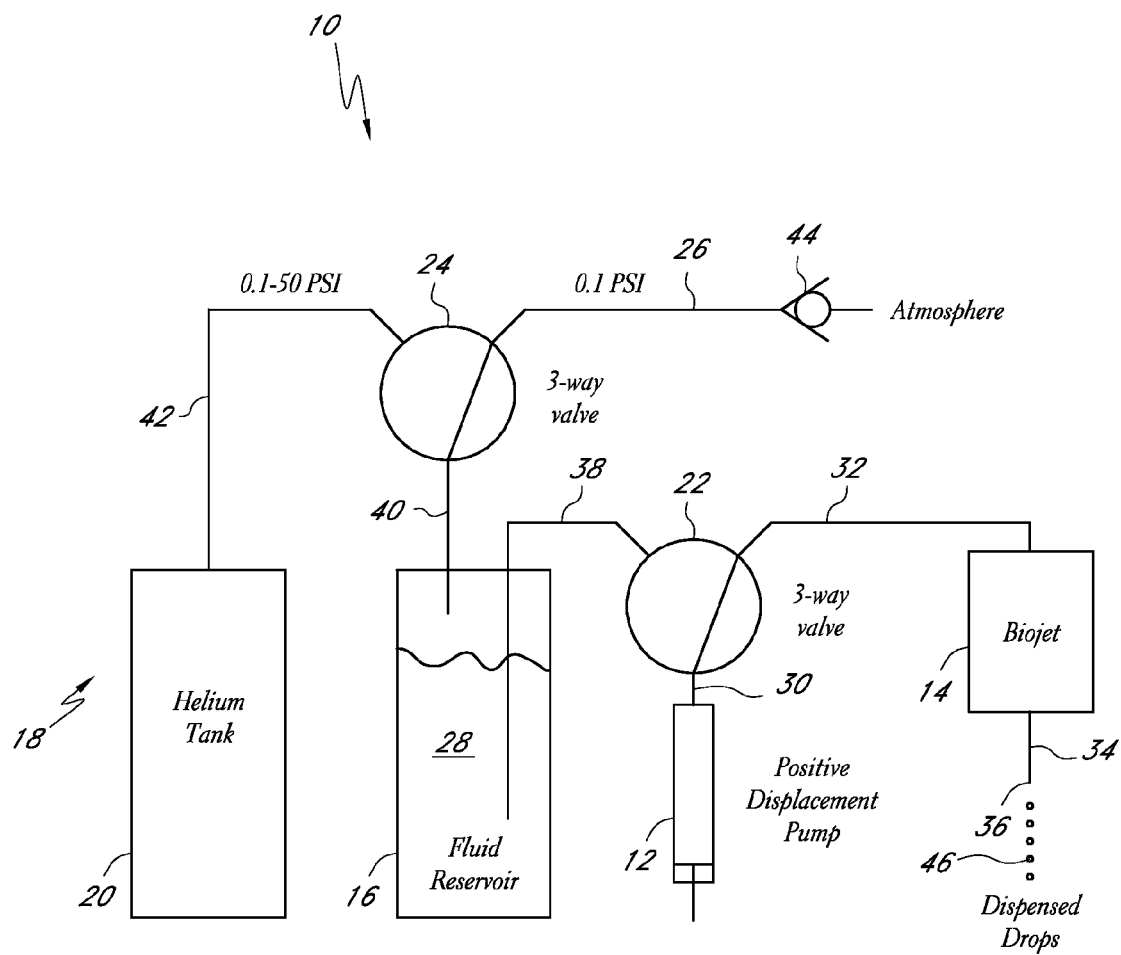
FIG. 3 is a simplified schematic view of the dispensing system of FIG. 1 illustrating a dispense mode configuration having features and advantages in accordance with one embodiment of the invention.

In accordance with another embodiment, which is substantially universally suitable for different types of reagents, the helium sparging involves holding a positive, static pressure over the reservoir reagent or fluid. FIGS. 1-3 schematically illustrate a dispensing system 10 and its operation which utilizes degassing by providing a static helium pressure system.

Referring in particular to FIGS. 1-3, in some embodiments, the dispensing system 10 generally comprises a positive displacement pump 12, a dispenser 14, a reagent reservoir 16 and a degassing helium pressure system 18 including a helium tank 20. A first three(3)-way valve 22 is connected via feedlines to the positive displacement pump 12, the dispenser 14 and the reservoir 16. A second three(3)-way valve 24 is connected to the reservoir 16, the helium tank 20 and a vent line 26.

The positive displacement pump 12 draws fluid or reagent 28 from the reservoir 16 and precisely meters it to the dispenser 14 at the desired flow rate. A feedline 30 connects the pump 12 to the 3-way valve 22. Any one of a number of suitable direct current fluid sources may be utilized. In one embodiment, the pump 12 comprises a syringe pump.

The dispenser 14 can comprise any one of a number of dispensers. In one embodiment, the dispenser 14 comprises a solenoid actuator or solenoid actuated dispenser adapted to be opened and closed at a predetermined frequency and duty cycle. A feedline 32 connects the dispenser 14 to the 3-way valve 22.

A dispensing tip 34 connected to the dispenser 14 and has a distal end nozzle 36 with an emitting orifice for dispensing reagent or fluid. In some embodiments, the tip 34 comprises a ceramic tip.

The reservoir 16 contains the reagent or other liquid 28 to be dispensed. A first feedline 38 connects the reservoir 16 to the 3-way valve 22 and extends through the surface of the fluid 28 in the reservoir 16. A second feedline 40 connects the reservoir 16 to the 3-way valve 24 and terminates above the surface of the fluid 28 in the reservoir 16.

The tank 20 contains helium that is used to pressurize the reservoir 16 and degas the reagent 28, as discussed further below. A feedline 42 connects the tank 20 to the 3-way valve 24.

The vent line 26 has a one(1)-way valve 44 and terminates at an end open to the atmosphere or other ambient conditions. Other suitable valves such as open-close valves and the like may be utilized, as needed or desired, to control the flow within the system.

The degassing helium pressure system 18 provides helium to create a static pressure within the reservoir 16. In one embodiment, the helium static pressure can be varied between about 0.1 psig to about 50 psig, including all values and sub-ranges therebetween. In another embodiment, the helium static pressure can be varied between about 0.05 psig to about 200 psig, including all values and sub-ranges therebetween. In yet another embodiment, the helium static pressure can be varied between about 0.01 psig to about 500 psig, including all values and sub-ranges therebetween.

Referring in particular to FIG. 1, in operation, the 3-way valve 24 is switched so that the helium tank 20 and the reservoir 16 are connected through the feedlines 40, 42. The reservoir 16 is pressurized by helium from the tank 20 to a high pressure $P_H$ for degassing the reservoir liquid 28. The pressure $P_H$ is maintained for a period of time so that the helium diffuses into the liquid 28 and displaces dissolved oxygen and nitrogen.

The pressure $P_H$ is selected to be high enough for suitable degassing of the liquid 28. In one embodiment, the pressure $P_H$ is in the range from about 10 psig to about 30 psig, including all values and sub-ranges therebetween. In another embodiment, the pressure $P_H$ is in the range from about 0.1 psig to about 50 psig, including all values and sub-ranges therebetween. In yet another embodiment, the pressure $P_H$ is in the range from about 4 psig to about 100 psig, including all values and sub-ranges therebetween. In still another embodiment, the pressure $P_H$ is in the range from about 2 psig to about 200 psig, including all values and sub-ranges therebetween. In a further embodiment, the pressure $P_H$ is in the range from about 1 psig to about 500 psig, including all values and sub-ranges therebetween. In other embodiments, suitable higher or lower pressures $P_H$ may be efficaciously used, as needed or desired.

The helium static pressure within the reservoir 16 is reduced to a low positive residual value $P_V$, slightly above atmospheric, suitable for venting the reservoir 16. The 3-way valve 24 is switched so that the reservoir 16 is connected to the vent line 26 through the feedline 40. The one(1)-way valve 44 is opened to atmospheric or ambient conditions thereby venting gas from the reservoir 16.

In one embodiment, the pressure $P_V$ is in the range from about 0.01 psig to about 1 psig, including all values and sub-ranges therebetween. In another embodiment, the pressure $P_V$ is in the range from about 0.02 psig to about 0.5 psig, including all values and sub-ranges therebetween. In yet another embodiment, the pressure $P_V$ is in the range from about 0.05 psig to about 0.2 psig, including all values and sub-ranges therebetween. In still another embodiment, the pressure $P_V$ is about 0.1 psig. In other embodiments, suitable higher or lower pressures $P_V$ may be efficaciously used, as needed or desired.

The pressurization to a high pressure $P_H$ followed by venting to the atmosphere at a low positive residual pressure $P_V$ is typically repeated a number of times. This serial dilution method of re-pressurizing and venting serves to substantially fully, or to a large degree, degas the reservoir reagent 28.

Referring in particular to FIG. 2, after degassing, the positive displacement pump 12 is filled with the reagent 28. The 3-way valve 22 is switched (if not already switched) so that the pump 12 and the reservoir 16 are connected through the feedlines 30, 38. The pump 12 is operated to draw reagent into its syringe barrel.

Referring in particular to FIG. 3, the 3-way valve 22 is switched so that the pump 12 and the dispenser 14 are connected through the feedlines 30, 32. The fluid pressure within the pump 12 and the dispenser 14 is adjusted to a predetermined, computed and/or steady state dispense pressure $P_{SS}$. The connection between the displacement pump 12 and solenoid dispenser 14 is hydraulically coupled and operates at a substantially constant pressure under steady state conditions.

The pump 12 is operated to meter reagent 28 to the dispenser 14 which is actuated to open and close at a predetermined frequency and/or duty cycle to dispense reagent droplets 46 through the nozzle 36 of the dispensing tip 34. A stepper motor or the like can be used to provide pulsed operation of the pump 12 which may be synchronized with the pulsed operation of the dispenser 14 or offset with a desired phase lag or lead, as needed or desired.

The arrangement of FIGS. 1-3 illustrates a process that provides efficient degassing of the reagent 28 while effectively maintaining the steady state pressure $P_{SS}$ for dispensing in the hydraulic side of the system. During dispensing, the reagent reservoir 16 is maintained at a small helium static pressure $P_D$ or it can, be vented to the atmosphere or ambient conditions.

In one embodiment, the pressure $P_D$ is in the range from about 0.01 psig to about 1 psig, including all values and sub-ranges therebetween. In another embodiment, the pressure $P_D$ is in the range from about 0.02 psig to about 0.5 psig, including all values and sub-ranges therebetween. In yet another embodiment, the pressure $P_D$ is in the range from about 0.05 psig to about 0.2 psig, including all values and sub-ranges therebetween. In still another embodiment, the pressure $P_D$ is about 0.1 psig. In other embodiments, suitable higher or lower pressures $P_D$ may be efficaciously used, as needed or desired.

Advantageously, the above degassing process allows increased stability in dispensing sub-microfluidic drops having volumes down to about 1 nL and even in the picoliter range. Another advantage is that the build up of liquid on the nozzle tip is reduced thereby allowing for greater precision and release of sub-microfluidic droplets.

Figure 4:
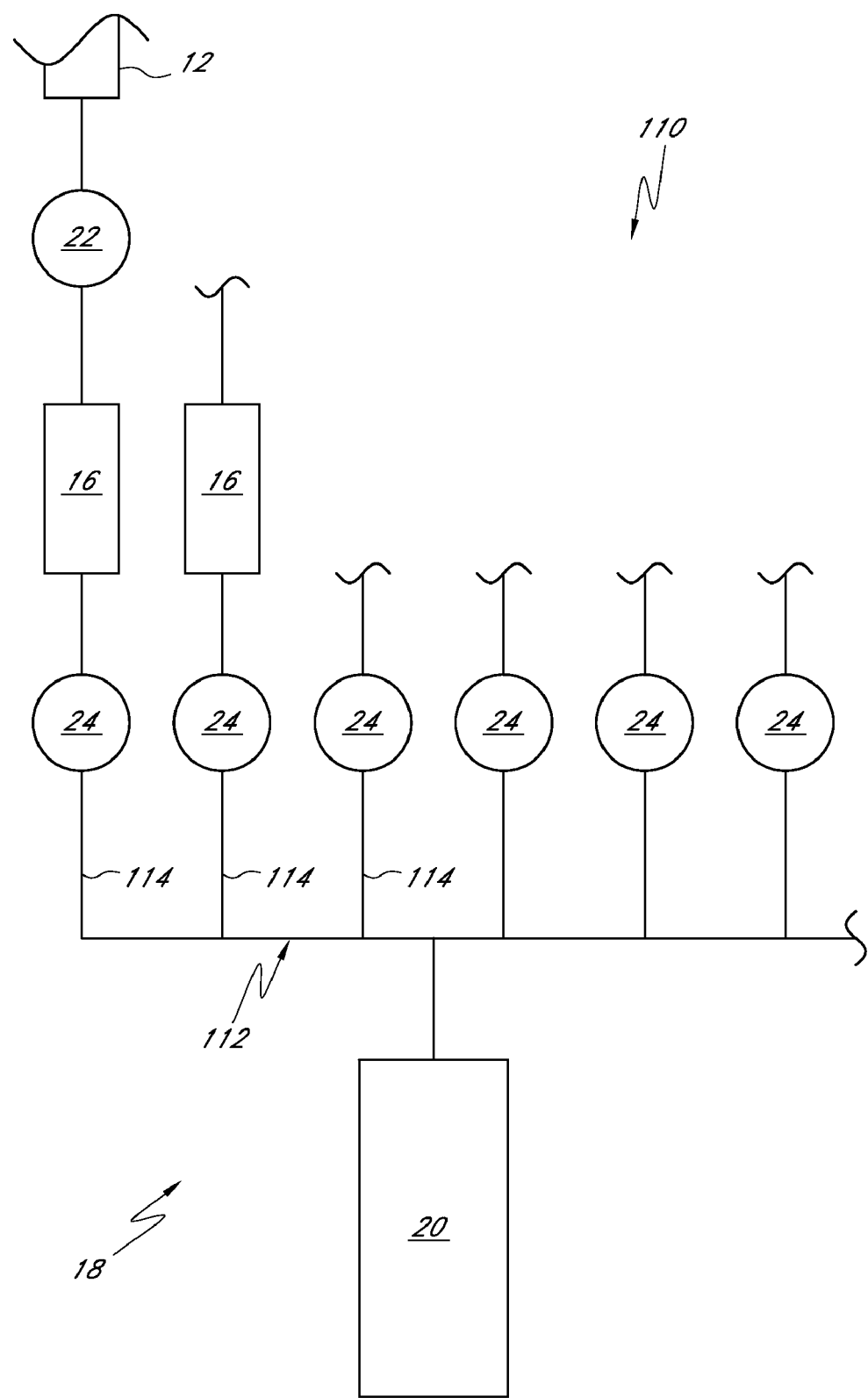
FIG. 4 is a simplified schematic partial view of a dispensing system including a multi-channel static helium pressure having features and advantages in accordance with one embodiment of the invention.

FIG. 4 illustrates a dispensing system 110 with a manifold system 112 that allows the helium sparging degassing process to be applied to a number of reagent reservoirs 16 which independently feed individual positive displacement pumps 12, such as on one machine. The manifold 112 has plurality of channels 114 connected to respective 3-way valves 24. A one-dimensional (1×N) or two-dimensional (M×N) manifold system may be utilized, as needed or desired. Advantageously, a single helium tank 20 connected to the manifold 112 can be used for degassing a plurality of reagent reservoirs 16.

Electrostatic Fields

In small drop dispensing, most substrates are made from dielectric materials and hence build up static charge. In addition, most reagents have some level of conductivity/charge associated with them. Thus, as the drop volumes become smaller the electric fields associated with the statically charged surfaces can deflect the drop from its intended trajectory.

In some embodiments, an electric field gradient is superimposed parallel to the intended drop trajectory so as to substantially eliminate or mitigate the static effects. The field direction is such as to attract the drop to the substrate surface. The electric field can also facilitate in biasing the drop release and ejection.

Figure 5:
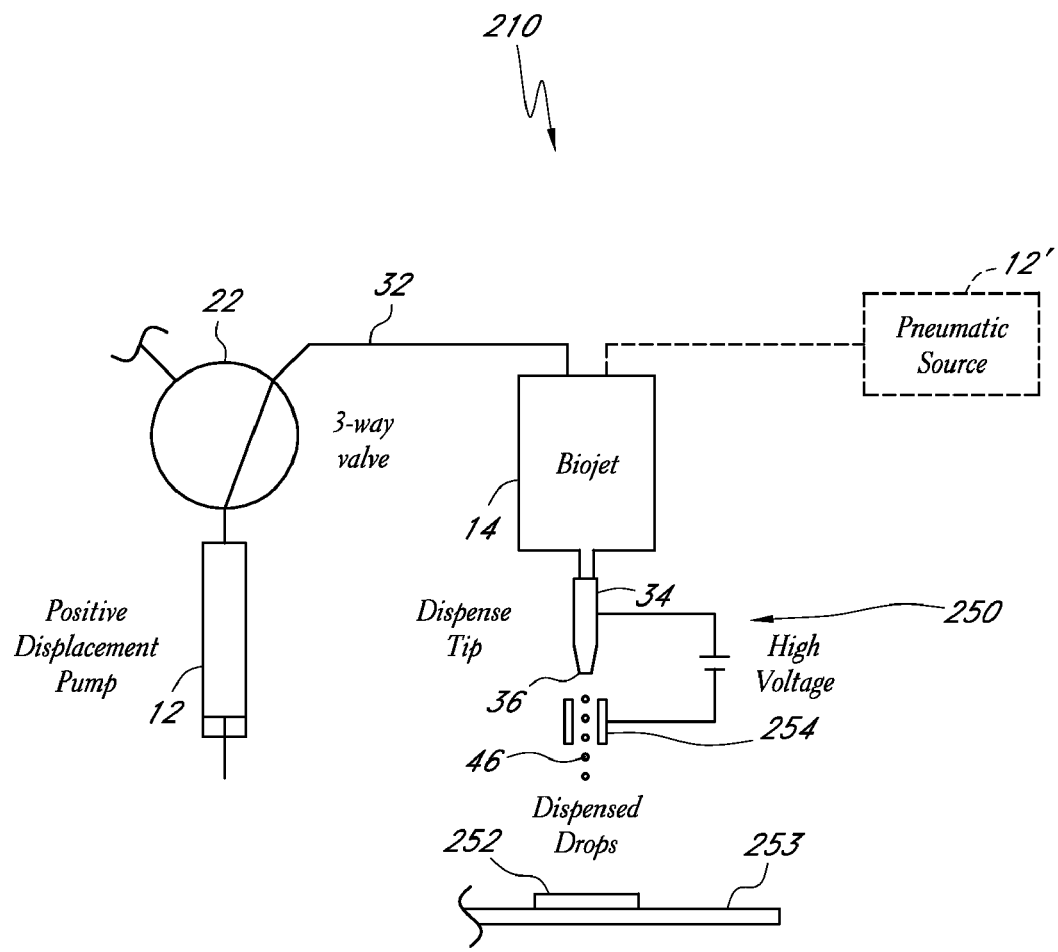
FIG. 5 is a simplified schematic partial view of a dispensing system including an electrostatic dispense field generator having features and advantages in accordance with one embodiment of the invention.
Figure 6:
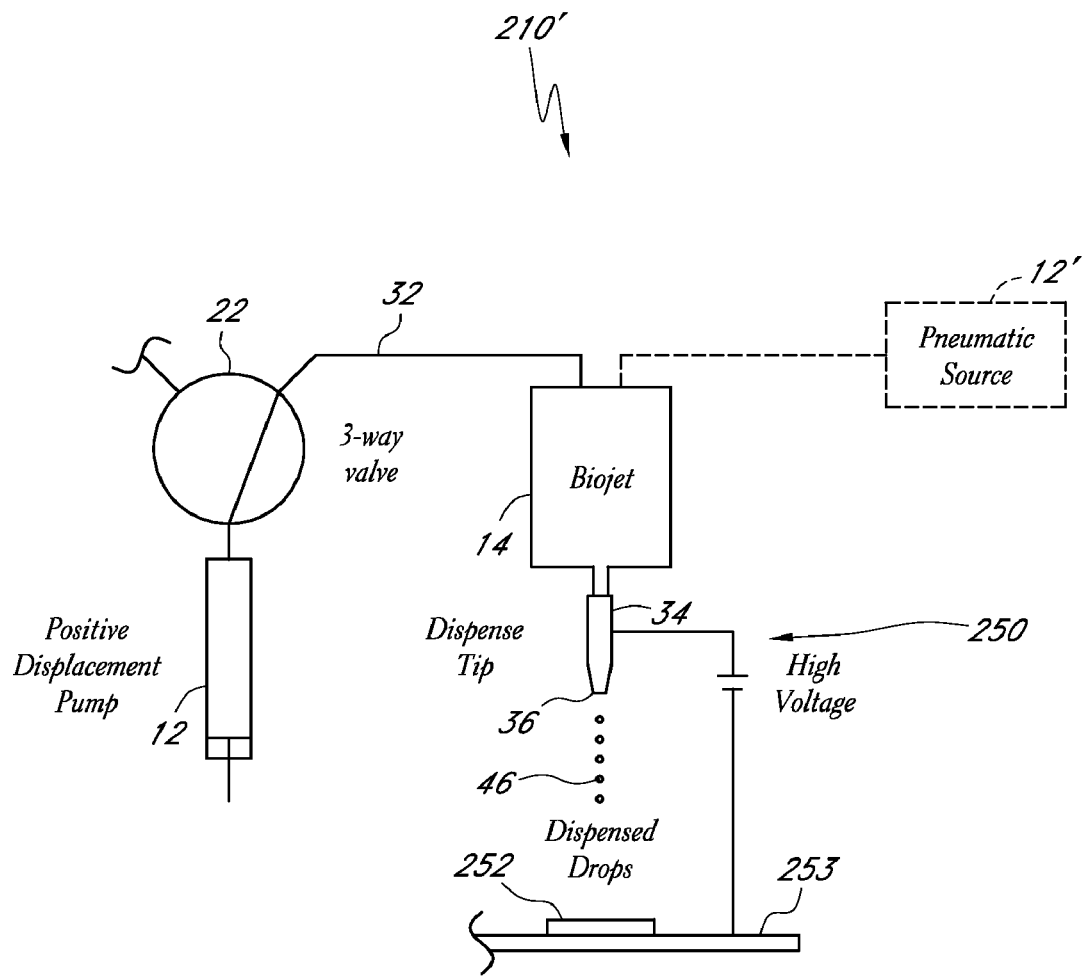
FIG. 6 is a simplified schematic partial view of a dispensing system including an electrostatic dispense field generator having features and advantages in accordance with another embodiment of the invention.
Figure 7:
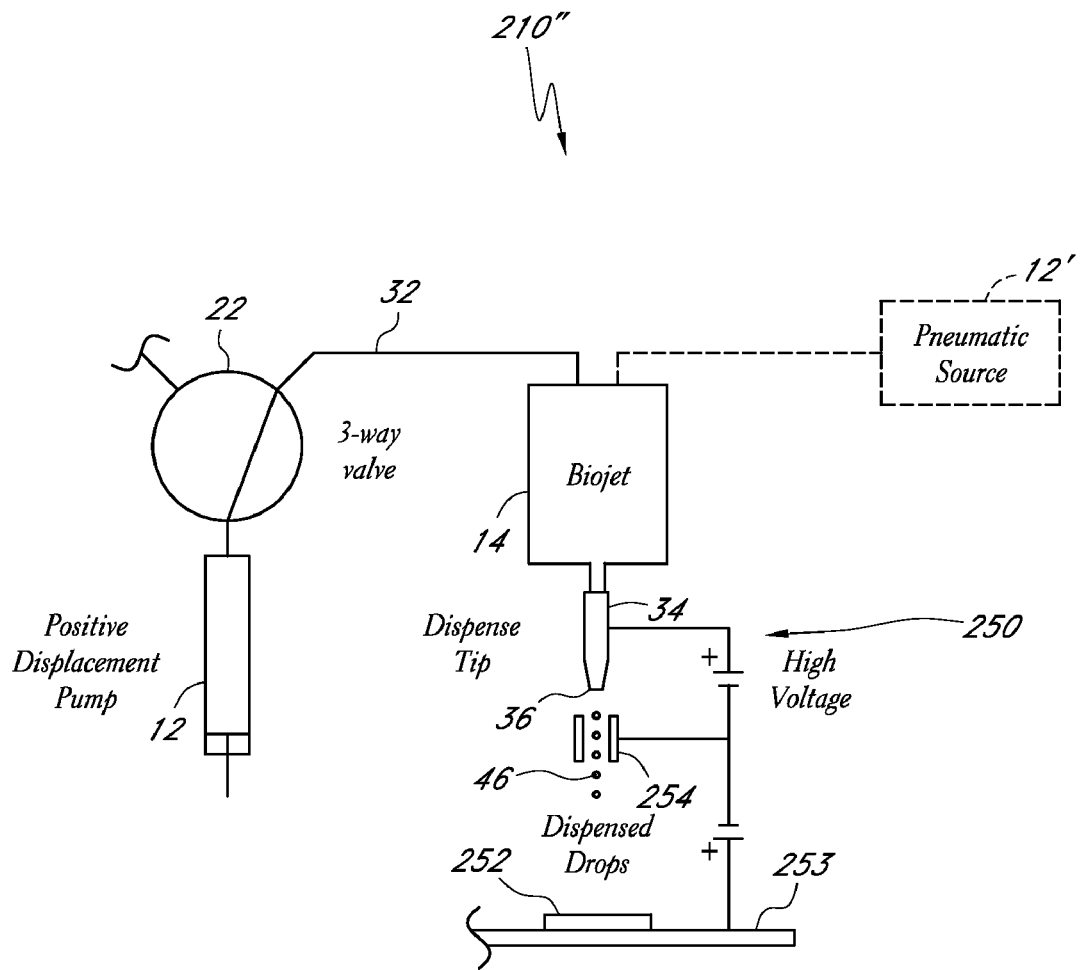
FIG. 7 is a simplified schematic partial view of a dispensing system including an electrostatic dispense field generator having features and advantages in accordance with yet another embodiment of the invention.

FIGS. 5-7 shows some embodiments of dispensing systems 210, 210', 210" including an electric field generator 250 to substantially eliminate or mitigate undesirable static effects that could deflect the droplets 46 from their intended trajectories. This is particularly advantageous for dispensing sub-microfluidic volumes, such as less than about 100 nL. The improved drop trajectories are particularly beneficial on a substrate or target 252 with a difficult topology such as a microtiter plate.

Any of the embodiments as disclosed, taught or suggested herein can utilize a suitable motion control system. This can include one or more robotic arms, X, X-Y or X-Y-Z platforms or tables that provide relative motion between selected system components such as the dispenser 14 (and dispense tip 34) and the substrate 252 (and substrate table 253) as well as components of the electric field generator 250.

Any of the embodiments as disclosed, taught or suggested herein can be configured in the form of a one-dimensional (1×N) or two-dimensional (M×N) array of dispensers 14 (and tips 34). One or more manifold systems may be utilized, as needed or desired. For example, a single pump 12 may be connected to a plurality of dispensers 14 via multi-channel manifold.

Any of the embodiments as disclosed, taught or suggested herein can utilize a suitable control system or controller to control and monitor the operation of the dispensing system and associated components. These include the pump 12, the dispenser 14, the motion system, the electrostatic bias generator 250 and the degassing operations.

Embodiments of the invention advantageously provide the positive displacement device 12, the actuator 14 and the tip 34 in combination with the electrostatic or electric field to improve dispensing characteristics and to enhance combined substrate 252 and drop 46 properties to obtain enhanced results such as smaller drop sizes, accuracy, repeatability and coefficient of variations (CVs), among other.

In the electric field embodiments of FIGS. 5-7, the table or platform 253, in one embodiment, comprises a conductive material with at least a conductive surface on a top portion thereof. The substrate 252 is seated on this conductive surface. In a modified embodiment, a conductive material or surface may be provided intermediate the substrate 252 and table 253.

In the embodiment of FIG. 5, the electrostatic dispense field generator 250 provides the field between the dispense tip 34 (and/or the nozzle 36) and a ring or tube electrode 254 intermediate the tip nozzle 36 and the substrate 252. The generator 250 provides an adjustable potential that allows a predetermined voltage or potential difference to be set between the tip nozzle 36 (and/or fluid therein) and the ring electrode 254. Thus, advantageously, accurate positioning of droplets 46 on the substrate 252 is achieved and release of smaller droplets 46 is facilitated. The ring electrode 254, in one embodiment, can be considered an electrostatic/electric alignment or biasing member or element.

The ring electrode 254 can comprise a suitable metal or the like. The generator 250 can utilize an electrode or the like attached to the tip 34. An array of ring electrodes 254 can be provided in a pattern that generally corresponds to the dispense channel pattern with one each in association with a respective one of the array of dispensing tips 34. The substrate table, platform or plate 253 can have one or more substrates 252 placed thereon.

In the embodiment of FIG. 6, the electrostatic dispense field generator 250 provides the field between the dispense tip 34 (and/or the nozzle 36) and the substrate table 253 (and/or substrates 252). The generator 250 provides an adjustable potential that allows a predetermined voltage or potential difference to be set between the tip nozzle 36 (and/or fluid therein) and the substrate table 253 (and hence the substrate(s) 252 through contact therebetween). Thus, advantageously, accurate positioning of droplets 46 on the substrate 252 is achieved and release of smaller droplets 46 is facilitated. The generator 250 can utilize suitable electrodes or the like attached to the tip 34 and the substrate table 253. The table 253, in one embodiment, can be considered an electrostatic/electric alignment or biasing member or element.

In the embodiment of FIG. 7, the electrostatic dispense field generator 250 can provide electric fields between the dispense tip 34 (and/or the nozzle 36), ring electrode 254 and the substrate table 253 (and/or substrates 252). The generator 250 provides an adjustable potential that allows a predetermined voltage or potential difference to be set between the tip nozzle 36 (and/or fluid therein) and the ring electrode 254. The generator 250 also provides an adjustable potential that can hold the substrate table 253 (and/or substrate(s) 252) at substantially the same potential as the ring electrode 254 or some other potential. Advantageously, accurate positioning of droplets 46 on the substrate 252 is achieved and release of smaller droplets 46 is facilitated. The generator 250 can utilize suitable electrodes or the like attached to the tip 34 and the substrate table 253. The ring electrode 254 and table 253, in one embodiment, can be considered electrostatic/electric alignment or biasing members or elements.

The electric fields of the generators 250 of the embodiments of FIGS. 5 and 6 add an additional component to the drop velocity. The drop impact velocity has a first component that is a function of the drop exit or ejection velocity and a second component that is a function of the biasing electric field. In some cases, if the electric field is large the drop velocity can be high enough that the drop 46 breaks on impact with the substrate 252 which may not be a desired result.

Advantageously, the electric field generator 250 of the embodiment of FIG. 7 allows for drop velocity control that may be used to substantially cancel or reverse the electrostatic velocity component. In one embodiment, the nozzle 36 (and/or fluid therein) is held at a potential +A, the ring electrode 254 is held at ground and the substrate table 253 (and/or substrate 252) is also held at a potential +A to substantially cancel or eliminate the electrostatic velocity component so that the drop impact velocity is substantially a function of the drop ejection velocity. In another embodiment, the substrate table 253 (and/or substrate 252) are held at a potential greater than +A to further reduce the drop impact velocity.

The electric fields applied can have a wide range of strengths. In one embodiment, the field is in the range from about 0.5 kilovolts (kV) to about 5 kV, including all values and sub-ranges therebetween. In another embodiment, the field is in the range from about 0.25 kilovolts (kV) to about 10 kV, including all values and sub-ranges therebetween. In yet another embodiment, the field is in the range from about 0.1 kilovolts (kV) to about 20 kV, including all values and sub-ranges therebetween. In modified embodiments, lower and higher electric fields may be utilized, as needed or desired.

In one embodiment, the electric field is in the form of a static voltage. In another embodiment, the electric field is pulsed at a predetermined frequency and/or duty cycle to provide a pulsed voltage.

In one embodiment, the pulsed electric field is synchronized with the motion and dispensing actions (pump 12, actuator 14). In this embodiment, the field is on when a drop is dispensed either in a step and repeat mode or on the fly and off otherwise.

In one embodiment, the electric field is synchronized or pulsed at substantially the same frequency (and/or duty cycle) as that of one or both of the positive displacement pulse (pump 12) and the valve pulse (dispenser 14). In one embodiment, phase adjustments (lag or lead) are provided between two or more of the electric field pulse, the positive displacement pulse and the valve pulse. In one embodiment, the time and magnitude of any of the electric field pulse, the positive displacement pulse and the valve pulse is varied.

In the embodiments of FIGS. 6 and 7, the electric fields desirably provide the ability to control the surface charge on the substrates 252. The electrostatic field will increase and more evenly distribute the charge on the substrate surface. The charge or some of it may remain even after the field is removed. This can be an advantage as it provides a more uniform surface relative to charge distribution and hence effective hydrophicity.

The electric field embodiments can also be used for bulk dispensing. These embodiments can also be used for aspiration of liquid for a reservoir, receptacle or source by dipping (or immersing) nozzle end of the tip 34 therein and operating the pump 12 in reverse to draw a predetermined amount of reagent or other liquid into the system. Thus, the tip 34 would also require periodic cleaning (washing and drying), for example, after completion of an aspirate-dispense cycle and before aspiration of another liquid.

The embodiment of FIG. 6 can be used for aspiration and cleaning by turning off the electric field during these operations. The embodiments of FIGS. 5 and 7, that include the ring electrode 254, involve further steps since it is not desirable to expose the electrode 254 to a washing action as it may present a shorting path between the tip 34 and the electrode 254.

In one embodiment, the ring electrode 254 is integrated or connected to the dispense tip 34 (and/or nozzle 36) and the electric field is turned off during aspiration and cleaning operations. This arrangement can be extended to an array of tips 34 with ring electrodes 254. In some embodiments, the ring electrode(s) 254 itself would be either dried or cleaned and dried periodically.

In another embodiment, a mechanism (e.g., robotic arm or the like) is provided to withdraw or move the ring electrode 254 (or array of ring electrodes 254) so that it does not interfere with the aspiration or cleaning operations which can then be performed with the electric field turned off. In some embodiments, the ring electrode(s) 254 itself would be either dried or cleaned and dried periodically.

Figure 8:
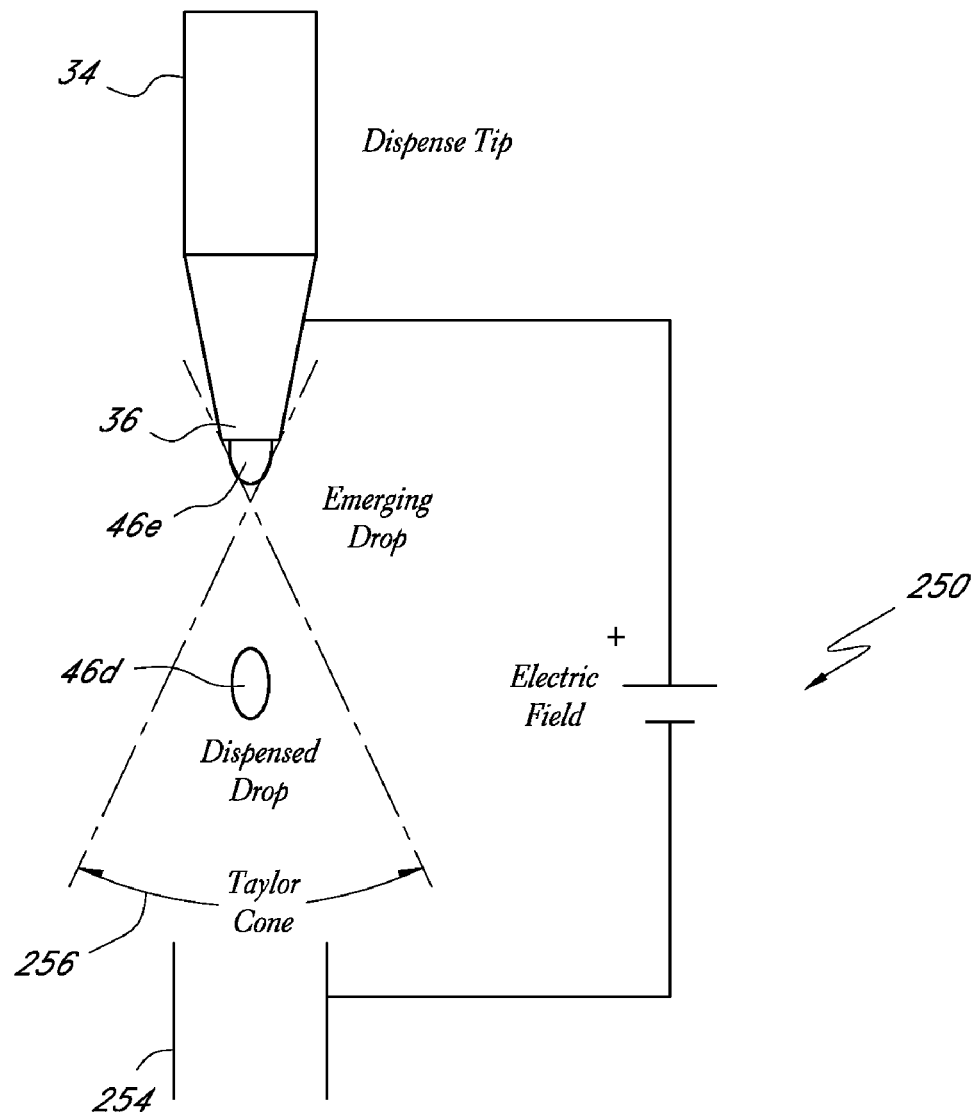
FIG. 8 is a simplified schematic enlarged view of a dispensing tip illustrating the formation of a Taylor cone and drop ejection generator having features and advantages in accordance with one embodiment of the invention.

FIG. 8 illustrates another advantage of the electric field embodiments particularly when the field in is the kilovolt (kV) range. This electric field can perturb the shape of the fluid meniscus in the nozzle tip 36 (see emerging drop 46e) to form a cone shape known as a Taylor cone 256. By forming a Taylor cone 256 and then using a superimposed positive displacement pulse a droplet 46d can be ejected from the tip of the Taylor cone 256.

Embodiments of the invention utilize the superimposed electric field which provides an added bias to the dispenser 14 for improved drop release when small positive displacements are used for sub-microfluidic drop ejection. These sub-microfluidic drop volumes are typically under 100 nL. Accurate and robust dispensing is achieved for drop sizes down to about 1 nL and even in the picoliter range.

Another important aspect is that the electric field, in effect, increases the hydrophobicity of the nozzle surface 36. This can be thought of as a "superficial" hydrophobicity created by the electric field. Thus, the field will drive the fluid build-up around the nozzle 36 into the Taylor cone 256 and advantageously prevent or substantially reduce the build-up of fluid on the outer surface of the nozzle 36. This desirably decreases the interaction of residual fluid on the nozzle tip 36 with the drop ejection. Advantageously, this provides increased drop release robustness, in particular for sub-microfluidic drop dispensing, and improves drop to drop coefficient of variations (CVs). These sub-microfluidic drop volumes are typically under 100 nL. Accurate and robust dispensing is achieved for drop sizes down to about 1 nL and even in the picoliter range.

The electric field embodiments of FIGS. 5-8 can be utilized in conjunction with both hydraulic sources (such as the positive displacement flow rate or "current" source 12) as well as pneumatic pressure or "voltage" sources which drive the dispenser 14. FIGS. 5-7 show a pneumatic source 12' (in phantom) connected to the dispenser 14. The electric field embodiments of FIGS. 5-8 can be used in conjunction with any of the embodiments disclosed, taught or suggested herein.

Figure 9:
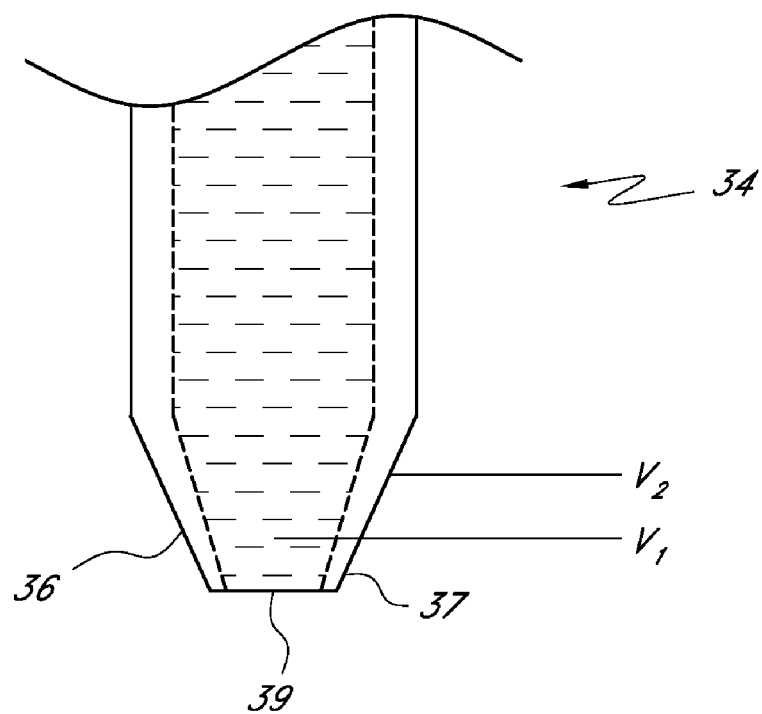
FIG. 9 is a simplified schematic partial view of a dispensing tip wherein a potential difference is maintained between the dispensing tip and the fluid therein having features and advantages in accordance with one embodiment of the invention.

FIG. 9 shows the dispensing tip 34 with the nozzle 36 wherein a voltage difference is maintained between the nozzle 36 (or tip 34) and the fluid therein. In this embodiment, the nozzle 36 (or tip 34) has a repulsive potential relative to the fluid such that the nozzle 36 (or tip 34) acts hydrophobic relative to the fluid. One example is to charge the fluid at $V_1 = -1000$ volts and the nozzle surface at $V_2 = -1100$ volts. The surface of the ceramic nozzle 36 (or tip 34) is coated with a conductive layer or film. The distal end 37 of the nozzle 36 (or tip 34) near the orifice 39 is not conductive.

Static Control of Dispense Nozzles

Figure 10:
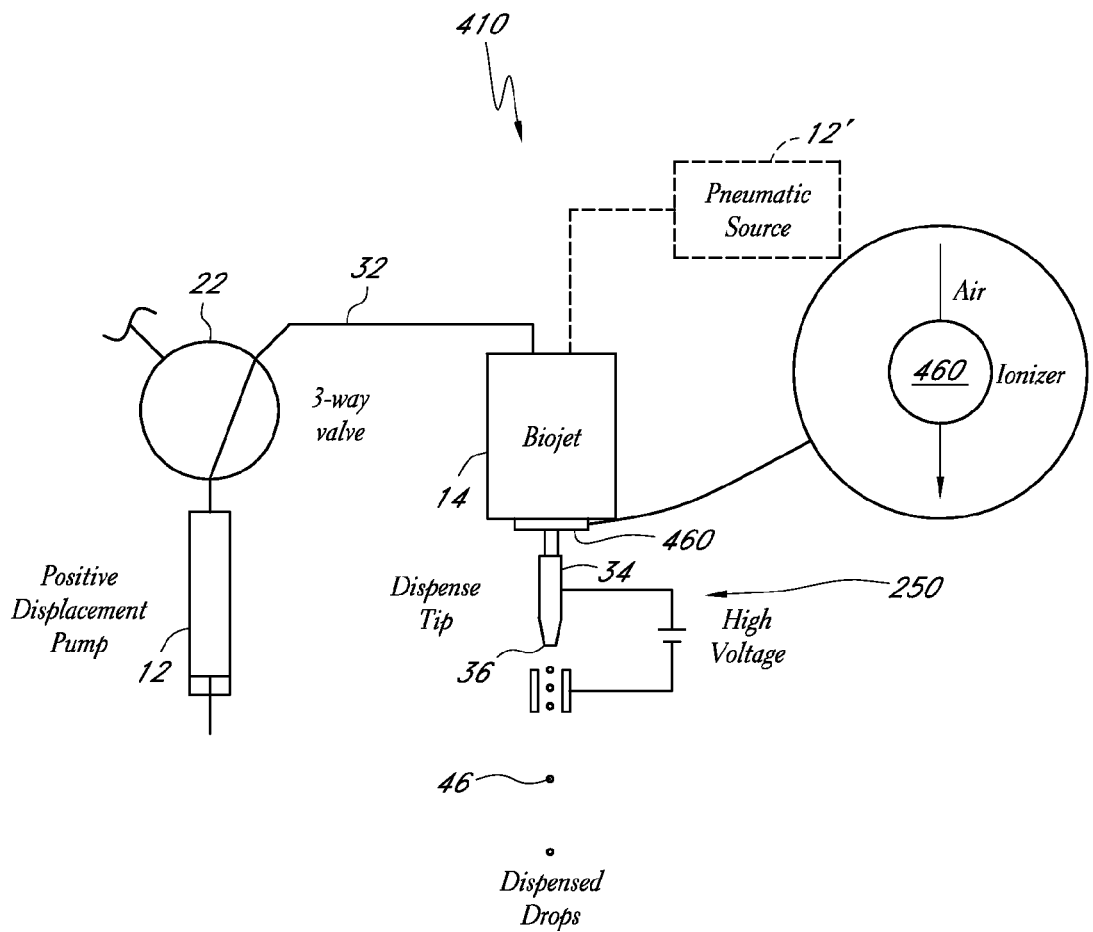
FIG. 10 is a simplified schematic partial view of a dispensing system including an air ionizer for static control having features and advantages in accordance with one embodiment of the invention.

FIG. 10 shows a dispensing system 410 including a miniature ionizer 460 on the dispense head 14 to provide a supply of ionized air around the nozzle 36 and reduce or prevent undesirable static charge build-up. (The ionizer 460 can be used in conjunction with any of the electric field embodiments or other embodiments disclosed, taught or suggested herein.) The presence of this ionized air improves the nozzle dispensing characteristics by inducing a hydrophobic effect on the nozzle surface. This can be thought of as a "superficial" hydrophobicity created by the ionized air.

Referring in particular to FIG. 10, advantageously, the build-up of fluid on the outer surface of the nozzle 36 is substantially prevented or reduced. This desirably decreases the interaction of residual fluid on the nozzle tip 36 with the drop ejection. Advantageously, this provides increased drop release robustness, in particular for sub-microfluidic drop dispensing, and improves drop to drop coefficient of variations (CVs). These sub-microfluidic drop volumes are typically under 100 nL. Accurate and robust dispensing is achieved for drop sizes down to about 1 nL and even in the picoliter range. In some embodiments, ionized air is bled over the substrate surface to further overcome undesirable static charge build-up.

The embodiment of FIG. 10 can be utilized in conjunction with both hydraulic sources (such as the positive displacement flow rate or "current" source 12) as well as pneumatic pressure or "voltage" sources which drive the dispenser 14. FIG. 10 shows a pneumatic source 12' (in phantom) connected to the dispenser 14. The embodiment of FIG. 10 can be utilized in conjunction with any of the embodiments as disclosed, taught or suggested herein.

Transverse Dispense Tip

Often, when dispensing into interior walls of cylinders or other narrow passageways, it is desirable to project drops transverse to the normal fluid flow path. One way to accomplish this is to orient the outlet orifice at right angles to the outlet fluid line itself. This allows the dispense tip to be shaped as a probe with drops emerging from the wall. In so doing, it has been found that the dynamic fluid motion within the outlet capillary can be improved by inserting a shaped surface just prior to the emitting orifice.

Figure 11:
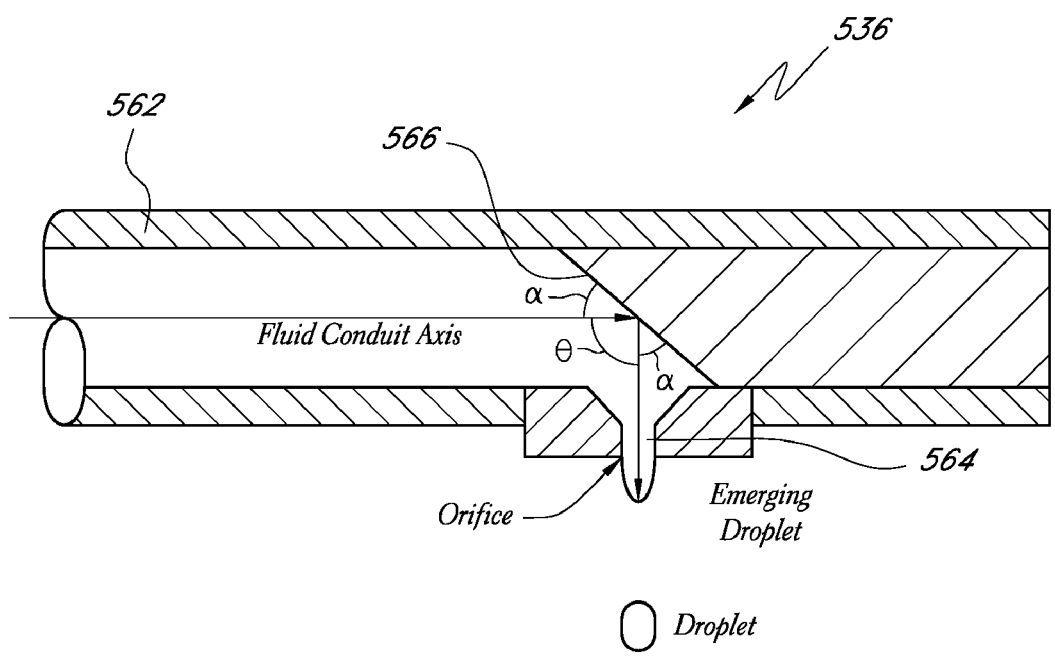
FIG. 11 is a simplified schematic view of a dispensing tip including a transverse ejection configuration having features and advantages in accordance with one embodiment of the invention.

FIG. 11 shows a transverse dispense tip 536 in which the axis of the main fluid conduit or passage 562 is substantially perpendicular to the axis of the outlet conduit or passage 564. A shaped surface 566 in the form of a uniform bevel directs the fluid flow into the outlet passage 564. The angle of the shaped surface 566 is half that of the projected drop axis. Stated differently, $\alpha = \theta/2$, where in this case $\theta = 90°$ and $\alpha = 45°$.

Figure 12:
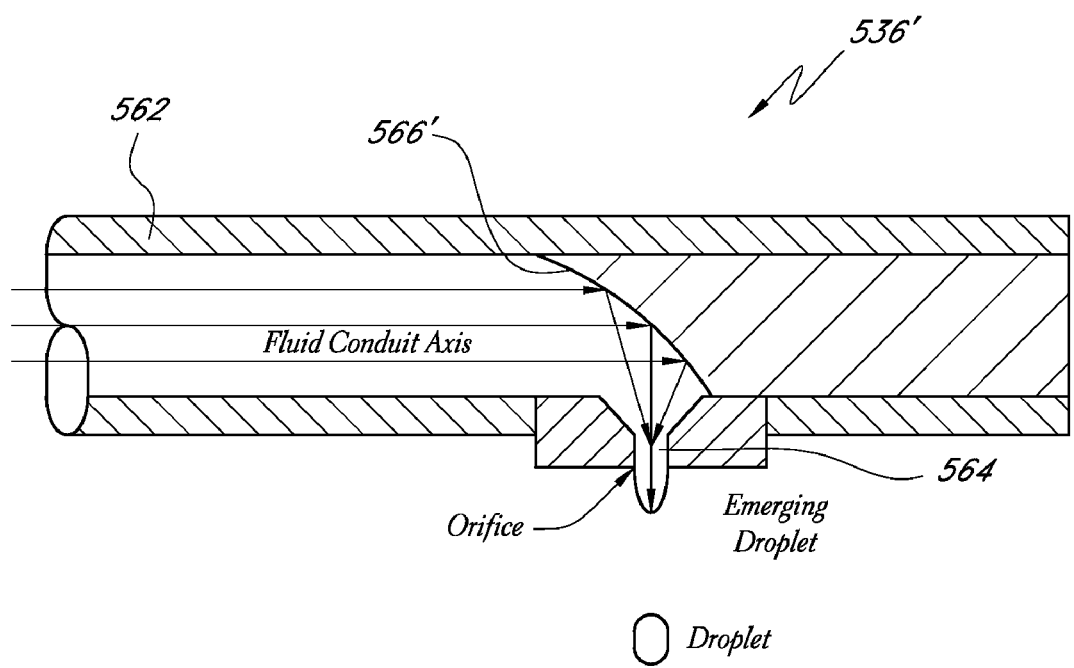
FIG. 12 is a simplified schematic view of a dispensing tip including a transverse ejection configuration having features and advantages in accordance with another embodiment of the invention.

FIG. 12 shows another embodiment of a transverse dispense tip 536' a shaped surface 566' in the outlet flow path that aids in drop dispensing. The contoured surface 566' enhances drop emissions and tends to focus the flow path towards the emitting orifice. The embodiments of FIGS. 11 and 12 can be used in conjunction with any of the electric field embodiments, degassing embodiments or other embodiments disclosed, taught or suggested herein including the dispensing system embodiments without an actuator/dispenser 14 which are described further below.

Dispensing Systems without Actuator

U.S. Pat. Nos. RE38,281 E, reissued Oct. 21, 2003, entitled DISPENSING APPARATUS HAVING IMPROVED DYNAMIC RANGE, and 6,063,339, issued May 16, 2000, entitled METHOD AND APPARATUS FOR HIGH-SPEED DOT ARRAY DISPENSING, the entirety of each one of which is hereby incorporated by reference herein, describe non contact dispensing systems based on a positive displacement pumped solenoid that is capable of accurately delivering individual drop sizes as small as about 10 nanoliters (nL). These systems generally comprises a positive displacement pump, a solenoid dispenser or actuator and a dispense tip. While such systems work very well with benign fluids such as aqueous based fluids, the use of aggressive fluids such as non polar solvents can cause attack or damage of the solenoid system.

Other issues include (1) cost of the solenoids, electrical harnesses and drive circuitry; (2) complex software and hardware to simultaneous operate the positive displacement, solenoid and motion system; (3) geometric and spacing constraints imposed by the size of the valves when an array of dispense channels is used; and (4) the electrical harness can also impose additional complexity with motion when the harnesses are tied to table motion and this complexity increases with the number of channels on a given system.

One solution is to remove the solenoid from the system. However, in such a system the smallest drop sizes achieved is of the order of a microliter. For example, it has been shown, with small orifice nozzles on a positive displacement syringe system (without the solenoid actuator/dispenser), that non contact drops can be ejected down to about 2 microliters (µL) using high frequency positive displacement pulses.

There is a growing need to dispense smaller sub-microfluidic drops (about less than 100 nL). The advantages of small drops include lower cost since may of the reagents or liquids dispensed are expensive.

As noted above, for drops having a volume of about below 100 nL and production applications with long duty cycles several problems can arise. One is an air bubble build up in the fluid lines due to precipitation of air from the liquid solution. Another is a build up of fluid droplets on the dispense nozzle surface which can interfere with the drop release from the nozzle tip. The build up of fluid droplets on the dispense nozzle surface can also be caused by the air bubbles passing through the ejection orifice and bursting to undesirably force fluid around the nozzle tip and cause ejection of unwanted satellite drops.

In addition to the drop release issues, as the drops become smaller, electrostatic deflection of the drops becomes an increasingly more important issue. Many target substrates tend to be dielectric and hence build up static charge that can produce electric fields strong enough to deflect the drops in flight.

Vacuum degassing can be used to prevent or reduce undesirable air bubbles within the liquid. The vacuum degassing involves applying a vacuum or reduced pressure to the reagent-containing reservoir so that dissolved gases precipitate as gas bubbles. In addition, ultrasonic stimulation can be applied to accelerate the precipitation of gas bubbles. Hence, the reagent withdrawn by the positive displacement pump will have reduced levels of dissolved gas.

One of the problems with the use of this vacuum degassing system is that it needs to be turned off when the syringe positive displacement system is pumping fluid from the degassed reservoir. Thus, disadvantageously, a mechanism is needed to turn the vacuum on and off during operation and hence the vacuum degasser becomes a relatively complicated solution to the degassing problem. It also becomes even more complicated and expensive if more than one reagent reservoir is being used in conjunction with a single dispensing machine.

Another issue with vacuum degassing is that when the vacuum is removed, atmospheric gases will quickly redissolve in the fluid hence this method is limited in how low the gas concentration can be reduced in the fluid during the machine operation. There is also a limit to how low a vacuum can be maintained with the fluid.

In some instances, the drops being dispensed often meet geometric constraints where the target zone is inaccessible because of the size of the dispensing device. In many product applications, this can force compromises in both product and dispenser design. This issue is not easily rectified by simply scaling down the size of existing technology.

Embodiments of the invention overcome one or more of the above disadvantages by providing a dispensing system, without a solenoid actuator/dispenser or the like, comprising an electric field generator that facilitates in dispensing sub-microfluidic drop volumes (more particularly, about 100 nL and less). Advantageously, this allows a very inert fluid path and hence use of aggressive fluids, an ability to position dispense tips of an array closer to one another and eliminates the electrical connections of the solenoids.

Some embodiments provide an electric field generator to facilitate ejection of small drops (in one embodiment, about 100 nanoliters and less) by providing an electrostatic bias. Some embodiments provide an electric field generator to substantially eliminate or mitigate undesirable electrostatic deflections of small drops. Some embodiments provide an electric field generator to control the droplet impact velocity.

The electric field embodiments provide several advantages. These include improved control of the drop trajectory to the substrate and facilitation of sub-microfluidic drop ejection. Another advantage is addition of an electrostatic deformation of the fluid meniscus to aid in the drop release of small volume drops of about 100 nL and below. Yet another advantage is reduction of residual fluid on the nozzle surface in proximity to the tip orifice. The electric field embodiments may be used in conjunction with both pneumatically as well as hydraulically driven dispensing systems.

Some embodiments provide a helium sparging degassing system and improve the quality of degassing of one or more reagent reservoirs. Some embodiments provide improved drop release from the nozzle tip for small drops (in one embodiment, about 100 nanoliters and below).

Some embodiments provide ionized air flow over the dispense nozzles to control static charge. Some embodiments utilize a transverse dispensing tip configuration allow for ejecting drops at right angles to the conventional liquid flow path, thereby allowing entry into small dispense target zones.

The degassing embodiments provide several advantages. One advantage is reduced air in the hydraulic fluid lines. Another advantage is improved drop release. Yet another advantage is the elimination or reduction of bubble explosions, which is one source of satellites and fluid accumulation on the nozzles. A further advantage is improved dispensing robustness at small drop volumes, in one embodiment, of about 100 nL and below.

The dispense nozzle static control embodiments have several advantages. One advantage is reduction of residual fluid on the nozzle surface in proximity to the tip orifice. Another advantage is reduction in charging of substrates. The static control embodiments may be used in conjunction with both pneumatically as well as hydraulically driven dispensing systems.

The transverse drop emitting tip configurations provide several advantages. One advantage is enhanced droplet formation at the dispense orifice. Another advantage is the ability to dispense droplets at a predetermined angle to the main outlet fluid flow path.

In one embodiment, the dispensed droplets have a volume of about 30 nL. In another embodiment, the dispensed droplets have a volume in the range from about 20 nL to about 50 nL, including all values and sub-ranges therebetween. In yet another embodiment, the dispensed droplets have a volume in the range from about 10 nL to about 100 nL, including all values and sub-ranges therebetween. In still another embodiment, the dispensed droplets have a volume in the range from about 5 nL to about 200 nL, including all values and sub-ranges therebetween. In a further embodiment, the dispensed droplets have a volume of less than about 500 nL. In another further embodiment, the dispensed droplets have a volume less than about 1 microliter ($\mu$L).

Degassing

The degassing methods and systems disclosed, taught or suggested herein can be used in conjunction with any of the embodiments disclosed, taught or suggested herein. In accordance with one embodiment, and as discussed further below, helium sparging is used for efficient degassing of the reagent or liquid.

In one embodiment, the helium sparging involves substantially continuously bubbling helium gas through the reagent. This approach may be suitable for several types of reagents but may not be compatible with certain types of reagents such as reagents with certain types of surfactants and proteins. The bubbling action can cause foaming of some types of fluids, particularly those fluids with surfactants. The foaming can cause organic molecules to be torn apart on the surface of the foam bubbles, that is, protein denaturing.

Figure 13:
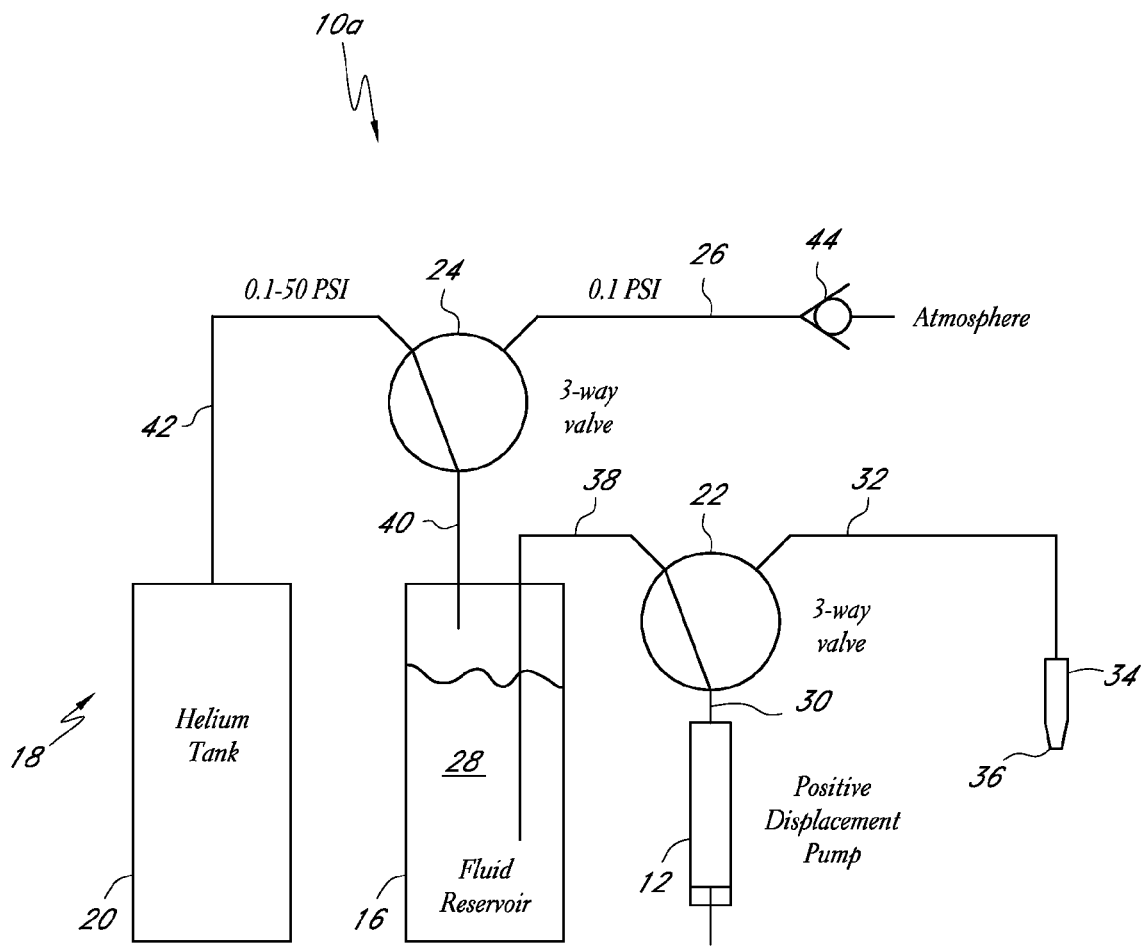
FIG. 13 is a simplified schematic view of a dispensing system including a static helium pressure system and illustrating a reservoir pressurization configuration having features and advantages in accordance with one embodiment of the invention.
Figure 14:
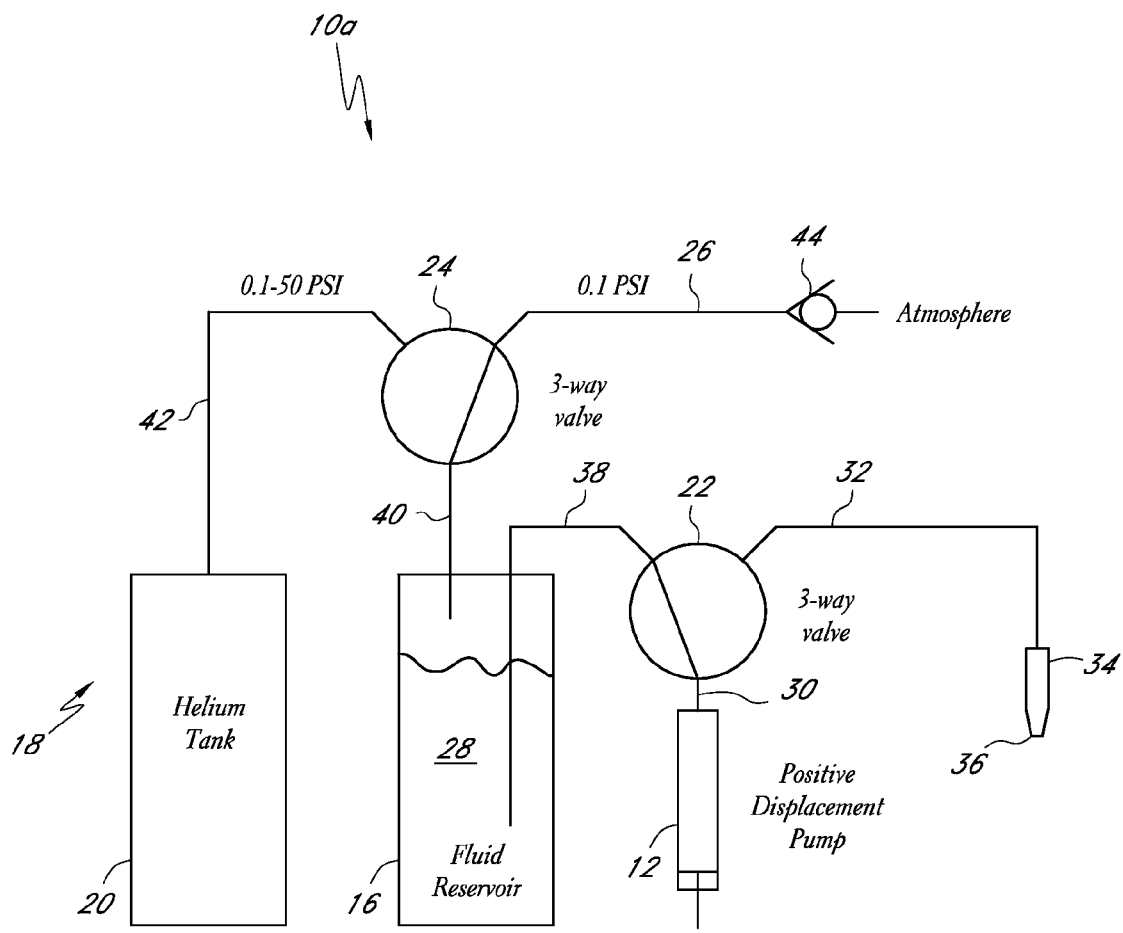
FIG. 14 is a simplified schematic view of the dispensing system of FIG. 13 illustrating a pump filling configuration having features and advantages in accordance with one embodiment of the invention.
Figure 15:
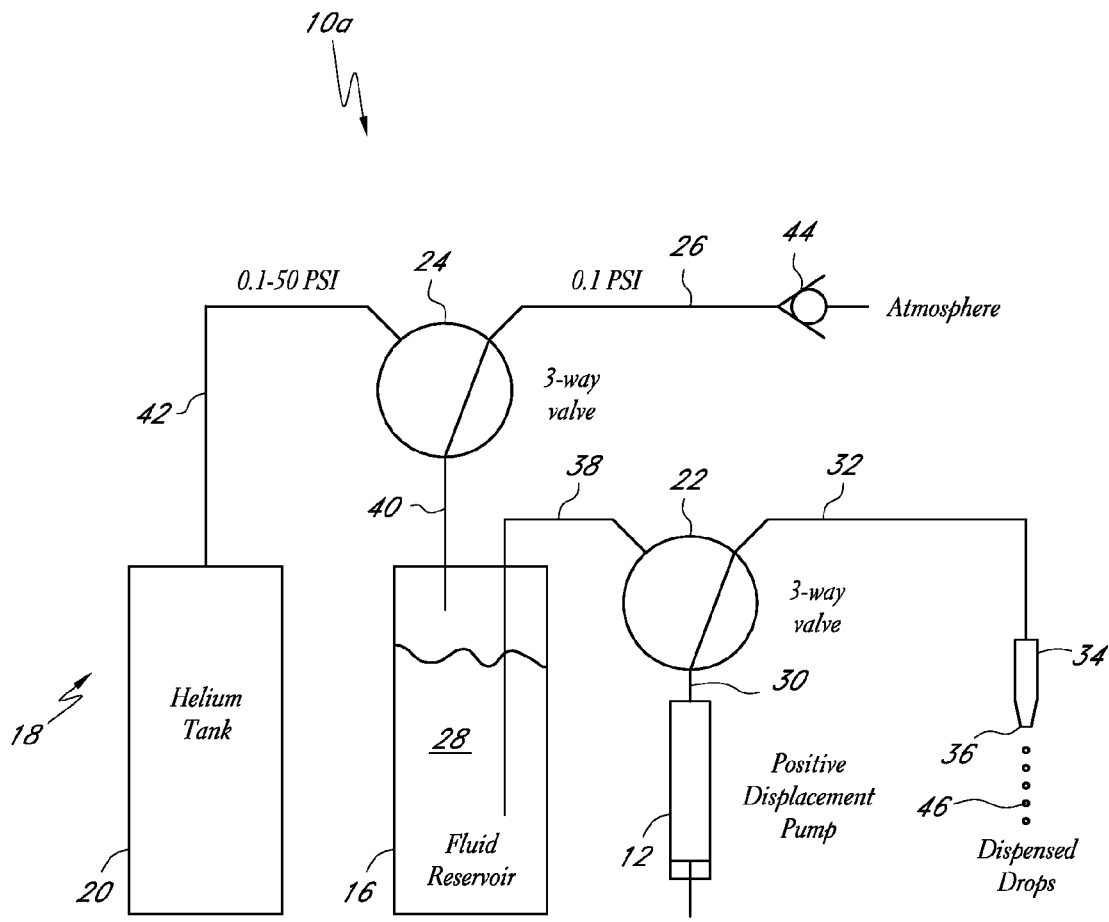
FIG. 15 is a simplified schematic view of the dispensing system of FIG. 13 illustrating a dispense mode configuration having features and advantages in accordance with one embodiment of the invention.

In accordance with another embodiment, which is substantially universally suitable for different types of reagents, the helium sparging involves holding a positive, static pressure over the reservoir reagent or fluid. FIGS. 13-15 schematically illustrate a dispensing system 10a (without an actuator or dispenser 14) and its operation which utilizes degassing by providing a static helium pressure system. Any of the electric field) embodiments as described herein can be used in combination with the system 10a which desirably allows for dispensing of sub-microfluidic volumes.

Referring in particular to FIGS. 13-15, in some embodiments, the dispensing system 10 generally comprises a positive displacement pump 12, a dispense tip 34, a reagent reservoir 16 and a degassing helium pressure system 18 including a helium tank 20. A first three(3)-way valve 22 is connected via feedlines to the positive displacement pump 12, the dispense tip 34 and the reservoir 16. A second three (3)-way valve 24 is connected to the reservoir 16, the helium tank 20 and a vent line 26.

The positive displacement pump 12 draws fluid or reagent 28 from the reservoir 16 and precisely meters it to the dispense tip 34 at the desired flow rate. A feedline 30 connects the pump 12 to the 3-way valve 22. Any number of suitable direct current fluid sources may be utilized. In one embodiment, the pump 12 comprises a syringe pump.

The dispensing tip 34 has a distal end nozzle 36 with an emitting orifice for dispensing reagent or fluid. In some embodiments, the tip 34 comprises a ceramic tip. A feedline 32 connects the tip 34 to the 3-way valve 22.

The reservoir 16 contains the reagent or other liquid 28 to be dispensed. A first feedline 38 connects the reservoir 16 to the 3-way valve 22 and extends through the surface of the fluid 28 in the reservoir 16. A second feedline 40 connects the reservoir 16 to the 3-way valve 24 and terminates above the surface of the fluid 28 in the reservoir 16.

The tank 20 contains helium that is used to pressurize the reservoir 16 and degas the reagent 28, as discussed further below. A feedline 42 connects the tank 20 to the 3-way valve 24.

The vent line 26 has a one(1)-way valve 44 and terminates at an end open to the atmosphere or other ambient conditions. Other suitable valves such as open-close valves and the like may be utilized, as needed or desired, to control the flow within the system.

The degassing helium pressure system 18 provides helium to create a static pressure within the reservoir 16. In one embodiment, the helium static pressure can be varied between about 0.1 psig to about 50 psig, including all values and sub-ranges therebetween. In another embodiment, the helium static pressure can be varied between about 0.05 psig to about 200 psig, including all values and sub-ranges therebetween. In yet another embodiment, the helium static pressure can be varied between about 0.01 psig to about 500 psig, including all values and sub-ranges therebetween.

Referring in particular to FIG. 13, in operation, the 3-way valve 24 is switched so that the helium tank 20 and the reservoir 16 are connected through the feedlines 40, 42. The reservoir 16 is pressurized by helium from the tank 20 to a high pressure $P_H$ for degassing the reservoir liquid 28. The pressure $P_H$ is maintained for a period of time so that the helium diffuses into the liquid 28 and displaces dissolved oxygen and nitrogen.

The pressure $P_H$ is selected to be high enough for suitable degassing of the liquid 28. In one embodiment, the pressure $P_H$ is in the range from about 10 psig to about 30 psig, including all values and sub-ranges therebetween. In another embodiment, the pressure $P_H$ is in the range from about 0.1 psig to about 50 psig, including all values and sub-ranges therebetween. In yet another embodiment, the pressure $P_H$ is in the range from about 4 psig to about 100 psig, including all values and sub-ranges therebetween. In still another embodiment, the pressure $P_H$ is in the range from about 2 psig to about 200 psig, including all values and sub-ranges therebetween. In a further embodiment, the pressure $P_H$ is in the range from about 1 psig to about 500 psig, including all values and sub-ranges therebetween. In other embodiments, suitable higher or lower pressures $P_H$ may be efficaciously used, as needed or desired.

The helium static pressure within the reservoir 16 is reduced to a low positive residual value $P_V$, slightly above atmospheric, suitable for venting the reservoir 16. The 3-way valve 24 is switched so that the reservoir 16 is connected to the vent line 26 through the feedline 40. The one(1)-way valve 44 is opened to atmospheric or ambient conditions thereby venting gas from the reservoir 16.

In one embodiment, the pressure $P_V$ is in the range from about 0.01 psig to about 1 psig, including all values and sub-ranges therebetween. In another embodiment, the pressure $P_V$ is in the range from about 0.02 psig to about 0.5 psig, including all values and sub-ranges therebetween. In yet another embodiment, the pressure $P_V$ is in the range from about 0.05 psig to about 0.2 psig, including all values and sub-ranges therebetween. In still another embodiment, the pressure $P_V$ is about 0.1 psig. In other embodiments, suitable higher or lower pressures $P_V$ may be efficaciously used, as needed or desired.

The pressurization to a high pressure $P_H$ followed by venting to the atmosphere at a low positive residual pressure $P_V$ is typically repeated a number of times. This serial dilution method of re-pressurizing and venting serves to substantially fully, or to a large degree, degas the reservoir reagent 28.

Referring in particular to FIG. 14, after degassing, the positive displacement pump 12 is filled with the reagent 28. The 3-way valve 22 is switched (if not already switched) so that the pump 12 and the reservoir 16 are connected through the feedlines 30, 38. The pump 12 is operated to draw reagent into its syringe barrel.

Referring in particular to FIG. 15, the 3-way valve 22 is switched so that the pump 12 and the dispense tip 34 are connected through the feedlines 30, 32. The pump 12 is operated to provide fluid to the tip 34 with the two being hydraulically coupled.

The pump 12 is operated to meter reagent 28 to the dispense tip 34 to dispense reagent droplets 46 through the nozzle 36 of the dispensing tip 34. A stepper motor or the like can be used to provide, in some embodiments, pulsed operation of the pump 12.

The arrangement of FIGS. 13-15 illustrates a process that provides efficient degassing of the reagent 28 while effectively dispensing from the hydraulic side of the system. During dispensing, the reagent reservoir 16 is maintained at a small helium static pressure $P_D$ or it can be vented to the atmosphere or ambient conditions.

In one embodiment, the pressure $P_D$ is in the range from about 0.01 psig to about 1 psig, including all values and sub-ranges therebetween. In another embodiment, the pressure $P_D$ is in the range from about 0.02 psig to about 0.5 psig, including all values and sub-ranges therebetween. In yet another embodiment, the pressure $P_D$ is in the range from about 0.05 psig to about 0.2 psig, including all values and sub-ranges therebetween. In still another embodiment, the pressure $P_D$ is about 0.1 psig. In other embodiments, suitable higher or lower pressures $P_D$ may be efficaciously used, as needed or desired.

Advantageously, the above degassing process allows increased stability in dispensing sub-microfluidic drops having volumes of about 100 nL or less. Another advantage is that the build up of liquid on the nozzle tip is reduced thereby allowing for greater precision and release of sub-microfluidic droplets.

The manifold system 112 of FIG. 4 can be utilized to allow the helium sparging degassing process to be applied to a number of reagent reservoirs 16 which independently feed individual positive displacement pumps 12, such as on one machine. Advantageously, and as noted above, a single helium tank 20 connected to the manifold 112 can be used for degassing a plurality of reagent reservoirs 16.

Electrostatic Fields

Figure 16:
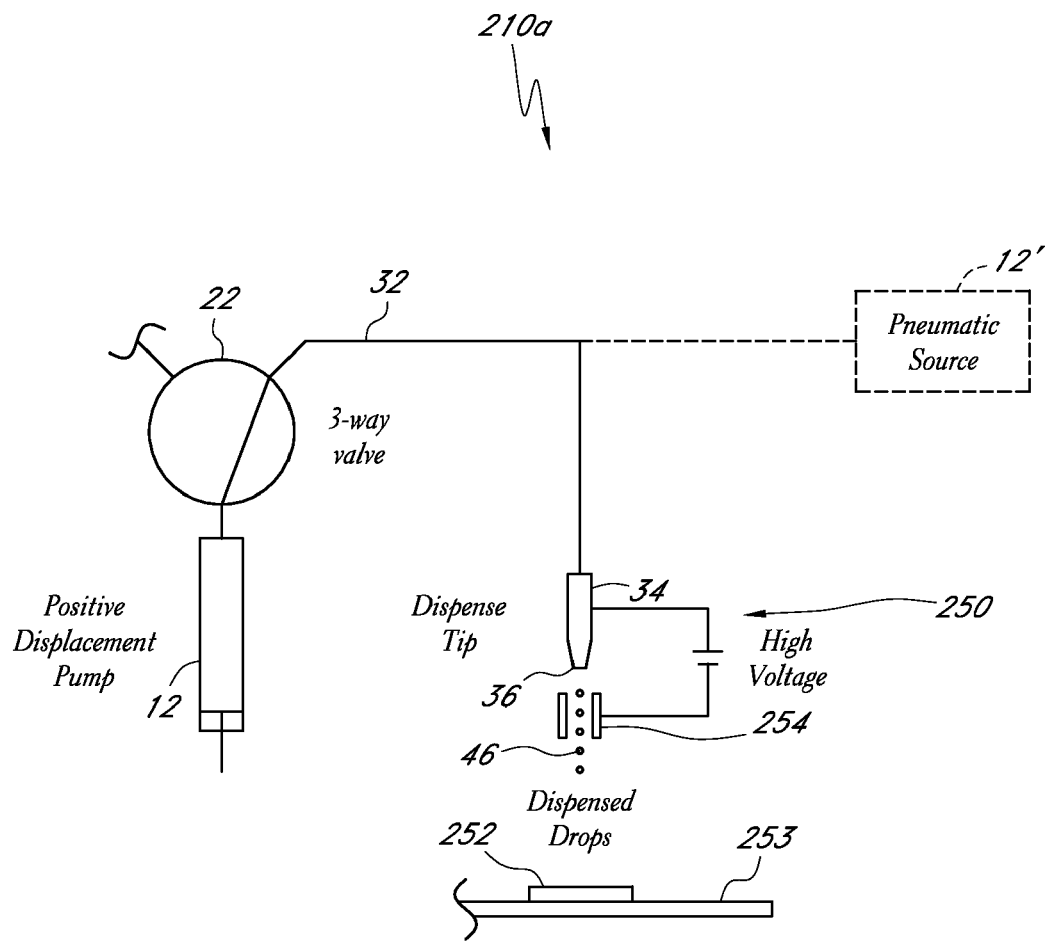
FIG. 16 is a simplified schematic partial view of a dispensing system including an electrostatic dispense field generator having features and advantages in accordance with one embodiment of the invention.
Figure 17:
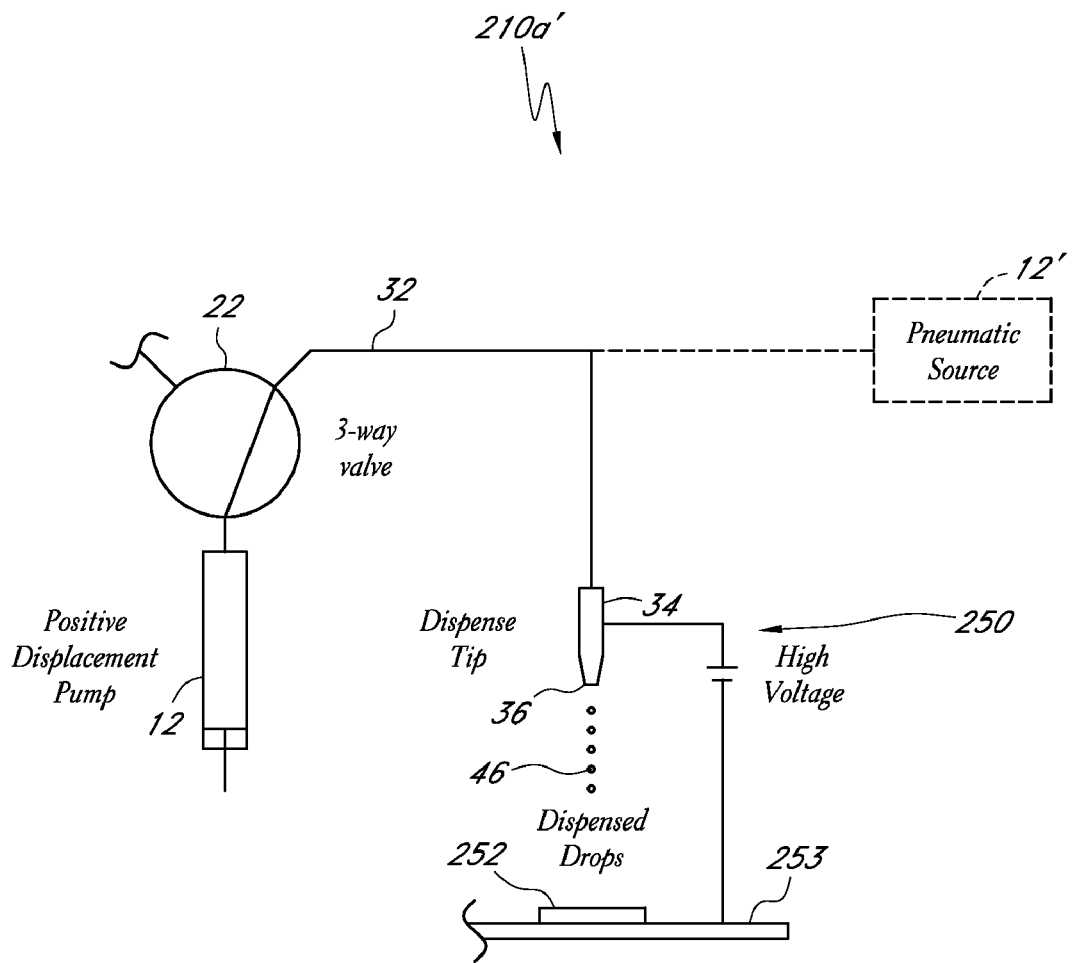
FIG. 17 is a simplified schematic partial view of a dispensing system including an electrostatic dispense field generator having features and advantages in accordance with another embodiment of the invention.
Figure 18:
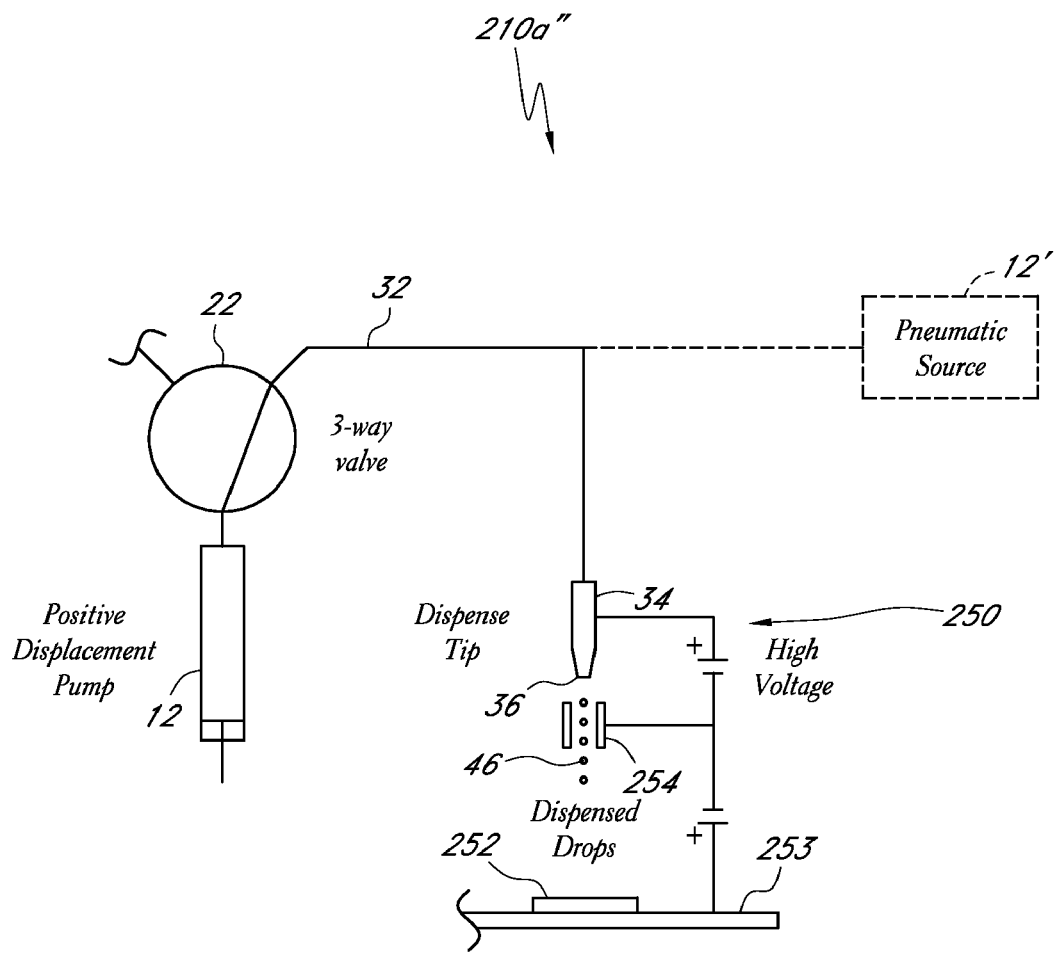
FIG. 18 is a simplified schematic partial view of a dispensing system including an electrostatic dispense field generator having features and advantages in accordance with yet another embodiment of the invention.

FIGS. 16-18 shows some embodiments of dispensing systems 210a, 210a', 210a" including an electric field generator 250. The embodiments of FIGS. 13-18 do not have a solenoid dispenser or actuator intermediate the pump 12 and dispense tip 34.

Advantageously, this provides a very inert fluid path from the pump 12 and the tip 34 and hence allows the use of aggressive fluids such as non polar solvents. In one embodiment, the inert path generally comprises glass (syringe barrel of the pump 12), Teflon® (feedlines 30, 32) and ceramic (dispense tip 34). In other embodiments, other suitable substantially inert materials may be efficaciously used, as needed or desired.

Elimination of the solenoid or the like also advantageously allows dispense tips 34 of an array to be positioned closer to one another. In one embodiment, the dispense tip (and/or nozzle) spacing is as small as about 2 mm. Another advantage is reduced complexity and compactness.

The electric field generator 250 of embodiments of the invention desirably facilitates in dispensing sub-microfluidic drop volumes (more particularly, about 100 nL and less). Some embodiments used pulsed positive displacement in combination with an electrostatic bias to facilitate ejection and release of sub-microfluidic drop volumes (more particularly, about 100 nL and less).

As indicated above, in small drop dispensing, many substrates are made from dielectric materials and hence build up static charge. In addition, most reagents have some level of conductivity/charge associated with them. Thus, as the drop volumes become smaller the electric fields associated with the statically charged surfaces can deflect the drop from its intended trajectory.

The electric field generator 250 of embodiments of the invention can superimpose an electric field gradient substantially parallel to the intended drop trajectory so as to substantially eliminate or mitigate undesirable static effects. The field direction is such as to attract the drop to the substrate surface. This is particularly advantageous for dispensing sub-microfluidic volumes, such as less than about 100 nL. The improved drop trajectories are particularly beneficial on a substrate 252 with a difficult topology such as a microtiter plate.

Any of the embodiments as disclosed, taught or suggested herein can utilize a suitable motion control system. This can include one or more robotic arms, X, X-Y or X-Y-Z platforms or tables that provide relative motion between selected system components such as the dispense tip 34 and the substrate 252 (and substrate table 253) as well as components of the electric field generator 250. One embodiment provides synchronization of the positive displacement pulse with motion in combination with the electrostatic field.

Any of the embodiments as disclosed, taught or suggested herein can be configured in the form of a one-dimensional (1×N) or two-dimensional (M×N) array of tips 34. One or more manifold systems may be utilized, as needed or desired. For example, a single pump 12 may be connected to a plurality of tips 34 via multi-channel manifold.

Any of the embodiments as disclosed, taught or suggested herein can utilize a suitable control system or controller to control and monitor the operation of the dispensing system and associated components. These include the pump 12, the motion system, the electrostatic bias generator 250 and the degassing operations.

Embodiments of the invention advantageously provide the positive displacement device 12 and the tip 34 in combination with the electrostatic or electric field to improve dispensing characteristics and to enhance combined substrate 252 and drop 46 properties to obtain enhanced results such as smaller drop sizes, accuracy, repeatability and CVs, among other.

In the electric field embodiments of FIGS. 16-18, the table or platform 253, in one embodiment, comprises a conductive material with at least a conductive surface on a top portion thereof. The substrate 252 is seated on this conductive surface. In a modified embodiment, a conductive material or surface may be provided intermediate the substrate 252 and table 253.

Experiments, for example, using the configuration shown in FIG. 16 with pulsed positive displacement have shown that drop sizes down to 30 nL can be accurately dispensed with a 100 micron (μm) nozzle orifice in a non contact mode using potentials in the range of about 1.5-3.0 kV using a step and repeat indexing mode. This represents a significant improvement in the minimum drop volume size (about 2 μL) achieved without the electric field and electrostatic bias features.

In the embodiment of FIG. 16, the electrostatic dispense field generator 250 provides the field between the dispense tip 34 (and/or the nozzle 36) and a ring or tube electrode 254 intermediate the tip nozzle 36 and the substrate 252. The generator 250 provides an adjustable potential that allows a predetermined voltage or potential difference to be set between the tip nozzle 36 (and/or fluid therein) and the ring electrode 254. Thus, advantageously, release of smaller droplets 46 is facilitated and accurate positioning of droplets 46 on the substrate 252 is achieved. The ring electrode 254, in one embodiment, can be considered an electrostatic/electric alignment or biasing member or element.

The ring electrode 254 can comprise a suitable metal or the like. The generator 250 can utilize an electrode or the like attached to the tip 34. An array of ring electrodes 254 can be provided in a pattern that generally corresponds to the dispense channel pattern with one each in association with a respective one of the array of dispensing tips 34. The substrate table, platform or plate 253 can have one or more substrates 252 placed thereon.

In the embodiment of FIG. 17, the electrostatic dispense field generator 250 provides the field between the dispense tip 34 (and/or the nozzle 36) and the substrate table 253 (and/or substrates 252). The generator 250 provides an adjustable potential that allows a predetermined voltage or potential difference to be set between the tip nozzle 36 (and/or fluid therein) and the substrate table 253 (and hence the substrate (s) 252 through contact therebetween). Thus, advantageously, release of smaller droplets 46 is facilitated and accurate positioning of droplets 46 on the substrate 252 is achieved. The generator 250 can utilize suitable electrodes or the like attached to the tip 34 and the substrate table 253. The table 253, in one embodiment, can be considered an electrostatic/electric alignment or biasing member or element.

In the embodiment of FIG. 18, the electrostatic dispense field generator 250 can provide electric fields between the dispense tip 34 (and/or the nozzle 36), ring electrode 254 and the substrate table 253 (and/or substrates 252). The generator 250 provides an adjustable potential that allows a predetermined voltage or potential difference to be set between the tip nozzle 36 (and/or fluid therein) and the ring electrode 254. The generator 250 also provides an adjustable potential that can hold the substrate table 253 (and/or substrate(s) 252) at substantially the same potential as the ring electrode 254 or some other potential. Thus, advantageously, release of smaller droplets 46 is facilitated and accurate positioning of droplets 46 on the substrate 252 is achieved. The generator 250 can utilize suitable electrodes or the like attached to the tip 34 and the substrate table 253. The ring electrode 254 and table 253, in one embodiment, can be considered electrostatic/electric alignment or biasing members or elements.

The electric fields of the generators 250 of the embodiments of FIGS. 16 and 17 add an additional component to the drop velocity. The drop impact velocity has a first component that is a function of the drop exit or ejection velocity and a second component that is a function of the biasing electric field. In some cases, if the electric field is large the drop velocity can be high enough that the drop 46 breaks on impact with the substrate 252 which may not be a desired result.

Advantageously, the electric field generator 250 of the embodiment of FIG. 18 allows for drop velocity control that may be used to substantially cancel or reverse the electrostatic velocity component. In one embodiment, the nozzle 36 (and/or fluid therein) is held at a potential +A, the ring electrode 254 is held at ground and the substrate table 253 (and/or substrate 252) is also held at a potential +A to substantially cancel or eliminate the electrostatic velocity component so that the drop impact velocity is substantially a function of the drop ejection velocity. In another embodiment, the substrate table 253 (and/or substrate 252) are held at a potential greater than +A to further reduce the drop impact velocity.

The electric fields applied can have a wide range of strengths. In one embodiment, the field is in the range from about 0.5 kilovolts (kV) to about 5 kV, including all values and sub-ranges therebetween. In another embodiment, the field is in the range from about 0.25 kilovolts (kV) to about 10 kV, including all values and sub-ranges therebetween. In yet another embodiment, the field is in the range from about 0.1 kilovolts (kV) to about 20 kV, including all values and sub-ranges therebetween. In modified embodiments, lower and higher electric fields may be utilized, as needed or desired.

In one embodiment, the electric field is in the form of a static voltage. In another embodiment, the electric field is pulsed at a predetermined frequency and/or duty cycle to provide a pulsed voltage.

In one embodiment, the pulsed electric field is synchronized with the motion and dispensing actions (pump 12). In this embodiment, the field is on when a drop is dispensed either in a step and repeat mode or on the fly and off otherwise.

In one embodiment, the electric field is synchronized or pulsed at substantially the same frequency (and/or duty cycle) as that of the positive displacement pulse (pump 12). In one embodiment, phase adjustments (lag or lead) are provided between the electric field pulse and the positive displacement pulse. In one embodiment, the time and magnitude of any of the electric field pulse and the positive displacement pulse is varied.

In the embodiments of FIGS. 17 and 18, the electric fields desirably provide the ability to control the surface charge on the substrates 252. The electrostatic field will increase and more evenly distribute the charge on the substrate surface. The charge or some of it may remain even after the field is removed. This can be an advantage as it provides a more uniform surface relative to charge distribution and hence effective hydrophicity.

The electric field embodiments can also be used for bulk dispensing. These embodiments can also be used for aspiration of liquid for a reservoir, receptacle or source by dipping (or immersing) nozzle end of the tip 34 therein and operating the pump 12 in reverse to draw a predetermined amount of reagent or other liquid into the system. Thus, the tip 34 would also require periodic cleaning (washing and drying), for example, after completion of an aspirate-dispense cycle and before aspiration of another liquid.

The embodiment of FIG. 17 can be used for aspiration and cleaning by turning off the electric field during these operations. The embodiments of FIGS. 16 and 18, that include the ring electrode 254, involve further steps since it is not desirable to expose the electrode 254 to a washing action as it may present a shorting path between the tip 34 and the electrode 254.

In one embodiment, the ring electrode 254 is integrated or connected to the dispense tip 34 (and/or nozzle 36) and the electric field is turned off during aspiration and cleaning operations. This arrangement can be extended to an array of tips 34 with ring electrodes 254. In some embodiments, the ring electrode(s) 254 itself would be either dried or cleaned and dried periodically.

In another embodiment, a mechanism (e.g., robotic arm or the like) is provided to withdraw or move the ring electrode 254 (or array of ring electrodes 254) so that it does not interfere with the aspiration or cleaning operations which can then be performed with the electric field turned off. In some embodiments, the ring electrode(s) 254 itself would be either dried or cleaned and dried periodically.

The electric field embodiments of FIGS. 16-18, particularly when the field is in the kilovolt (kV) range, can provide another advantage as illustrated in FIG. 8. This electric field can perturb the shape of the fluid meniscus in the nozzle tip 36 (see emerging drop 46e) to form a cone shape known as a Taylor cone 256. By forming a Taylor cone 256 and then using a superimposed positive displacement pulse a droplet 46d can be ejected from the tip of the Taylor cone 256.

Embodiments of the invention utilize the superimposed electric field which provides an added bias for improved drop release when small positive displacements are used for sub-microfluidic drop ejection. These sub-microfluidic drop volumes are typically under 100 nL. Accurate and robust dispensing can be achieved for drop sizes down to about tens of nanoliters and even less.

Another important aspect is that the electric field, in effect, increases the hydrophobicity of the nozzle surface 36. This can be thought of as a "superficial" hydrophobicity created by the electric field. Thus, the field will drive the fluid build-up around the nozzle 36 into the Taylor cone 256 and advantageously prevent or substantially reduce the build-up of fluid on the outer surface of the nozzle 36. This desirably decreases the interaction of residual fluid on the nozzle tip 36 with the drop ejection. Advantageously, this provides increased drop release robustness, in particular for sub-microfluidic drop dispensing, and improves drop to drop coefficient of variations (CVs). These sub-microfluidic drop volumes are typically under 100 nL. Accurate and robust dispensing can be achieved for drop sizes down to about tens of nanoliters and even less.

The electric field embodiments of FIGS. 16-18 can be utilized in conjunction with both hydraulic sources (such as the positive displacement flow rate or "current" source 12) as well as pneumatic pressure or "voltage" sources which drive the fluid displacement. FIGS. 16-18 show a pneumatic source 12' (in phantom) connected to the dispense tip 34.

The electric field embodiments can be used in conjunction with any of the embodiments as disclosed, taught or suggested herein. Any of the electric field embodiments can be used in conjunction with the dispensing systems described in U.S. Patent Application Publication No. US 2003/022824 A1, published Dec. 11, 2003 (U.S. patent application Ser. No. 10/394,402, filed Mar. 19, 2003), entitled APPARATUS FOR LIQUID SAMPLE HANDLING, the entirety of which is hereby incorporated by reference herein.

Figure 19:
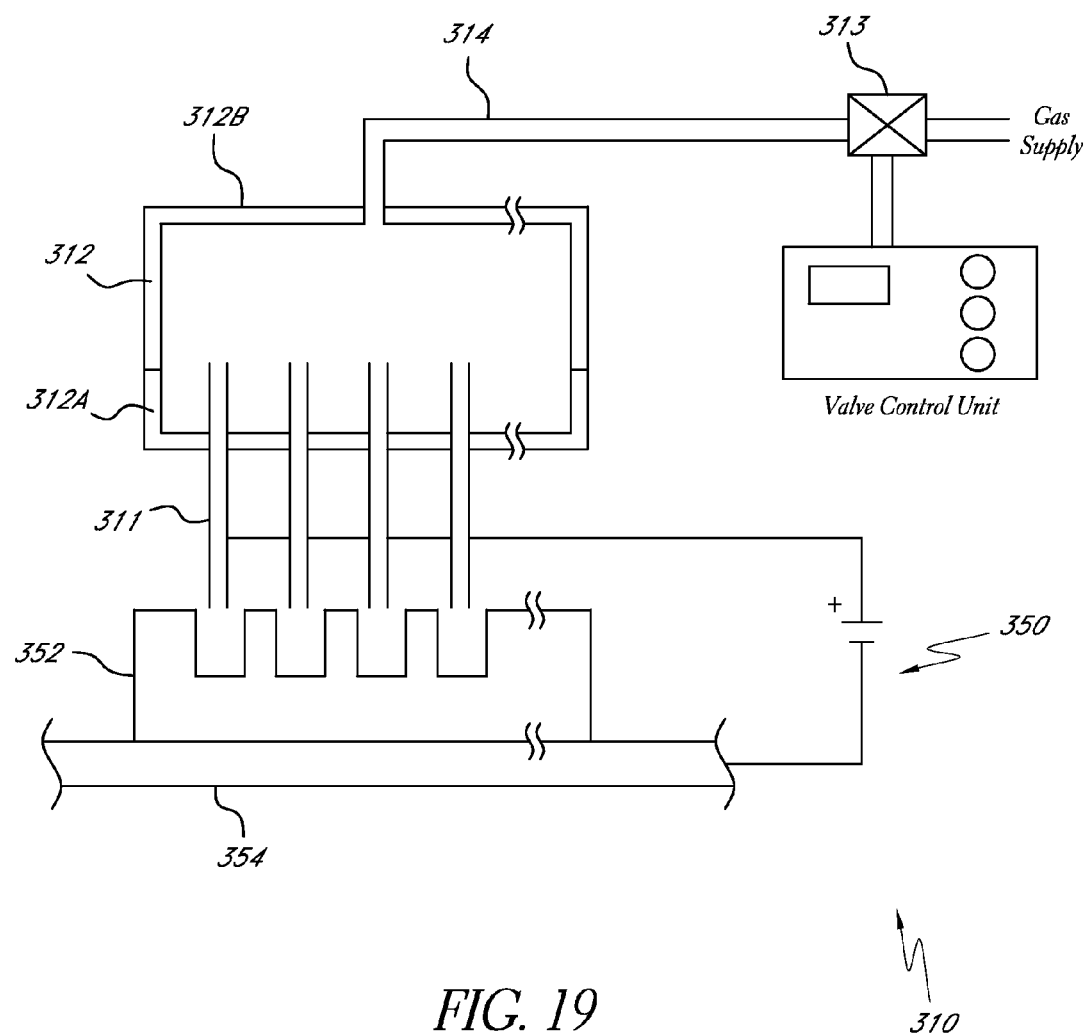
FIG. 19 is a simplified schematic view of a dispensing system including an electrostatic dispense field generator having features and advantages in accordance with a further embodiment of the invention.

FIG. 19 shows a dispensing system 310 including an electric field generator 350 to provide an electrostatic bias and substantially eliminate or mitigate undesirable static effects that could deflect the droplets from their intended trajectories. The apparatus 310 generally comprises a plurality of hollow capillaries 311, a housing 312 which retains the capillaries 311 in their desired orientation and means to effect sample removal from the capillaries 311.

Each capillary 311 is open at both ends and has a defined internal volume. On contact of an open end of the capillary 311 with a sample a defined volume of sample is drawn up into the capillary by capillary action.

The capillaries 311 are retained, within the housing 312 which has two portions which form a cavity. A portion 312A which retains the capillaries 311 in their desired orientation and a portion 312B which is provided with means to supply pressurized gas to the cavity. Portions 312A and 312B are preferably separable but are capable of engaging to form a pressure tight seal. Pressurized gas is provided by means of a control valve 313 and line 314.

Referring to FIG. 19, the capillaries 311 dispense fluid onto or into one or more substrates 352 (e.g. microtiter plates) being held on one or more nests or tables 354. The electric field generator includes a first electrode connected to the capillaries or tips 311 or to the fluid in the tips 311 and a second electrode connected to the nests or substrate tables 354 holding the target plates 352.

The use of the electrostatic field generator 350 charges the bottom of the plates 352 through contact with the nest(s) or table(s) 354. Thus, undesirable static effects that could deflect the dispensed droplets from their intended trajectories are substantially eliminated or mitigated. Advantageously, improved control in accuracy of the volume transfer to the target plate 352 is achieved. Another advantage is that improved control of the drop pattern on the substrate 352 is achieved since any satellites are focused substantially perpendicularly (at 90°) to the nest(s) or table(s) 354 as opposed to at an ejected angle off axis to 90°. The table 354, in one embodiment, can be considered an electrostatic/electric alignment or biasing member or element.

In the electric field embodiment of FIG. 19, the table or platform 354, in one embodiment, comprises a conductive material with at least a conductive surface on a top portion thereof. The substrate 352 is seated on this conductive surface. In a modified embodiment, a conductive material or surface may be provided intermediate the substrate 352 and table 354.

As discussed above, electric fields in the kilovolt (kV) range can perturb the shape of the fluid meniscus in the nozzle tip to form a cone shape known as a Taylor cone. In the embodiment of FIG. 19, by forming a Taylor cone and then using a superimposed displacement or pressure pulse droplets can be ejected from the tips of the Taylor cone. This positive bias to the dispensing of the liquid from the capillaries 311 helps in overcoming surface tension effects (more particularly as droplet size becomes smaller) and reduces the pressure needed to eject the drops.

The dispense tip 34 of FIGS. 16-18 can also be used in accordance with the arrangement of FIG. 9 wherein a voltage difference is maintained between the nozzle 36 (or tip 34) and the fluid therein. In this embodiment, the nozzle 36 (or tip 34) has a repulsive potential relative to the fluid such that the nozzle 36 (or tip 34) acts hydrophobic relative to the fluid. One example is to charge the fluid at $V_1=-1000$ volts and the nozzle surface at $V_2=-1100$ volts. The surface of the ceramic nozzle 36 (or tip 34) is coated with a conductive layer or film. The distal end 37 of the nozzle 36 (or tip 34) near the orifice 39 is not conductive. This voltage difference embodiment of FIG. 9 can also be utilized in connection with any of the embodiments as disclosed, taught or suggested herein.

Static Control of Dispense Nozzles

Figure 20:
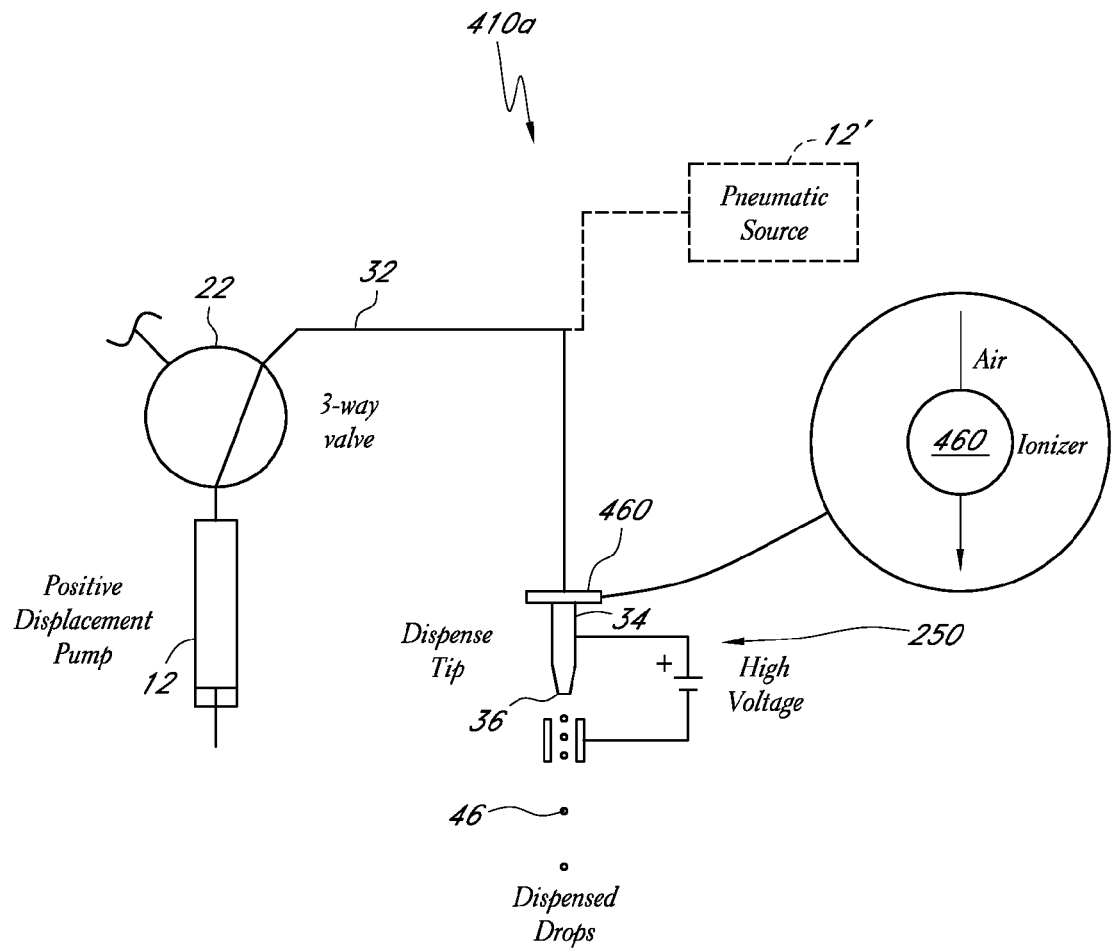
FIG. 20 is a simplified schematic partial view of a dispensing system including an air ionizer for static control having features and advantages in accordance with one embodiment of the invention.

FIG. 20 shows a dispensing system 410 including a miniature ionizer 460 on the dispense head 34 to provide a supply of ionized air around the nozzle 36 and reduce or prevent undesirable static charge build-up. (The ionizer 460 can be used in conjunction with any of the electric field embodiments.) The presence of this ionized air improves the nozzle dispensing characteristics by inducing a hydrophobic effect on the nozzle surface. This can be thought of as a "superficial" hydrophobicity created by the ionized air.

Referring in particular to FIG. 20, advantageously, the build-up of fluid on the outer surface of the nozzle 36 is substantially prevented or reduced. This desirably decreases the interaction of residual fluid on the nozzle tip 36 with the drop ejection. Advantageously, this provides increased drop release robustness, in particular for sub-microfluidic drop dispensing, and improves drop to drop coefficient of variations (CVs). These sub-microfluidic drop volumes are typically, in one embodiment, under 100 nL. Accurate and robust dispensing is achieved for drop sizes down to about tens of nanoliters and even less. In some embodiments, ionized air is bled over the substrate surface to further overcome undesirable static charge build-up.

The embodiment of FIG. 20 can be utilized in conjunction with both hydraulic sources (such as the positive displacement flow rate or "current" source 12) as well as pneumatic pressure or "voltage" sources which drive the system. FIG. 20 shows a pneumatic source 12' (in phantom) connected to the dispense tip 34.

The embodiment illustrated by FIG. 20 can be used in conjunction any of the embodiments as disclosed, taught or suggested herein including the dispensing systems disclosed in U.S. Patent Application Publication No. US 2003/022824 A1, published Dec. 11, 2003 (U.S. patent application Ser. No. 10/394,402, filed Mar. 19, 2003), entitled APPARATUS FOR LIQUID SAMPLE HANDLING, the entirety of which is hereby incorporated by reference herein.

Further Embodiments

Any of the embodiments disclosed, taught or suggested herein can utilize a number of types of sources, devices or pumps 12 including those with or without positive displacement and those with or without mass flow control. Any one of number of positive displacement devices can be utilized. In one embodiment, a syringe pump is utilized. In another embodiment, a pneumatic or gas pressure source with mass control feedback is utilized. In yet another embodiment, a pneumatic or gas pressure source with positive displacement is utilized. In still another embodiment, an electronically regulated pressurized source is utilized. In other embodiments, a rotary pump or device, a rotary piston pump or device, a peristaltic pump or device, a squash-plate pump or device and a deflection device may be utilized, as needed or desired.

The dispense tips 34 (and/or nozzle 36) can be configured in a wide variety of manners. These include various shapes such as tapered, frusto-conical, with varying or constant diameters, among others. They may comprise a wide variety of suitable materials including ceramics, plastics, metals, alloys, combinations thereof, among others. The surface properties can be selected and suitable coatings applied thereon, as needed or desired, for example to control surface charge, inertness, hydrophobicity, among others.

Any of the embodiments disclosed, taught or suggested herein can utilize additional elements in the fluid line (e.g., feedline 32), the dispense tip 34 and/or nozzle 36 to enhance dispensing properties such as drop size, accuracies and CVs, among others. In one embodiment, highly elastic elements are provided in the fluid line (e.g., feedline 32), the dispense tip 34 and/or nozzle 36. In another embodiment, constrictors are provided in the fluid line (e.g., feedline 32), the dispense tip 34 and/or nozzle 36, for example, to reduce the diameter such as at or proximate the dispense orifice. In yet another embodiment, dampeners are provided in the fluid line (e.g., feedline 32) to substantially eliminate or mitigate standing waves or reflected waves that could undesirably interfere with the dispensing operations.

Any of the embodiments disclosed, taught or suggested herein with an actuator or dispenser 14 can utilize a number of types of actuators or dispensers. In one embodiment, a solenoid actuator or dispenser is utilized. In another embodiment, a piezo or piezoelectric actuator or dispenser is utilized. In yet another embodiment, an aerosol or air jet actuator or dispenser is utilized. In still another embodiment, a pinch valve actuator or dispenser is utilized. In other embodiments, a magneto constriction actuator or dispenser, a fluid impulse actuator or dispenser, a heat actuated dispenser, a bubble jet actuator or dispenser and a deflection actuator or dispenser may be utilized, as needed or desired.

Substrate Assembly Embodiments

As indicated above for the electric field embodiments, in some embodiments, the table or platform 253 comprises a conductive material with at least a conductive surface on a top portion thereof. The substrate(s) 252 is seated on this conductive surface. The conductive material desirably facilitates creation of a strong electric field gradient to allow accurate dispensing of sub-microfluidic droplets.

Many practical substrates 253 are dielectric such as plastic microtiter plates and glass or plastic slides, among others. In many cases, special coatings are placed on substrate surfaces to enhance binding reactions of added chemistries. These coatings include wet chemistry which is dried on the surface and bonded membrane materials.

In some cases, if a relatively thick dielectric substrate is placed on top of the conductive surface (e.g. of the table 253) then the field gradient between the tip nozzle 36 and dielectric surface of the substrate 252 can be reduced and may not be strong enough to enhance the dispensing of small drops.

In one example, accurate dispensing of droplets having a volume in the 0.5 nL range was achieved using electrostatic bias with the solenoid and syringe dispensing system. In this example, a high field gradient in the range of 2-3 kilovolts over a distance of about 3 mm or less was used between the dispense tip nozzle 36 and the conductive surface. Under substantially the same conditions, when a dielectric substrate 252 (having a thickness greater than about 0.5 mm) was placed intermediate the dispense tip nozzle 36 and the conductive surface, the field gradient was altered enough to affect the accuracy of dispensing 0.5 nL droplets.

Accordingly, in some embodiments, a suitably thin dielectric substrate is used to mitigate the effect on the electric field gradient. For substantially the same conditions as in the above example, a conductive layer (e.g. a metal or the like) was provided intermediate a bonded membrane (thickness of about 100 µm) and a glass slide surface to provide enhanced dispensing with drop volumes down into the 0.5 nL range.

Advantageously, dielectric substrates can be used for enhanced electrostatic bias dispensing by adding a conductive layer. In one embodiment, the conductive layer is in combination with a secondary dielectric coating (e.g. wet chemistry). In another embodiment, the conductive layer is in combination with a membrane or the like.

Figure 21:
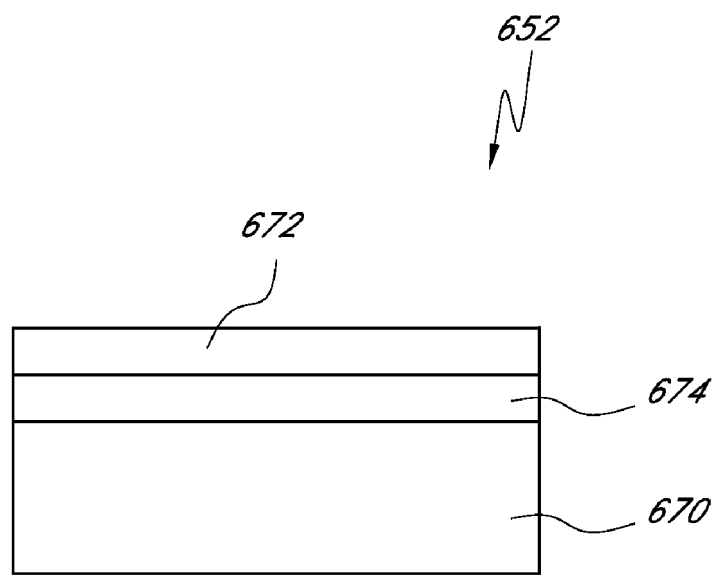
FIG. 21 is a simplified schematic view of a substrate assembly with a conductive layer having features and advantages in accordance with one embodiment of the invention.

FIG. 21 shows one embodiment of a target, substrate or substrate assembly 652 generally comprising a base or passive substrate element or portion 670, an active or functional substrate element or portion 672 on which droplets are dispensed and an intermediate conductive layer 674 for enhanced sub-microfluidic dispensing. In a modified embodiment, the substrate 652 may be constructed without the substrate element 670. The substrate embodiment of FIG. 21 can be used in conjunction with any of the electric field embodiments as disclosed, taught or suggested herein.

The substrate elements 670, 672 typically comprise a dielectric material. For example, the substrate element 670 can comprise glass or plastic slides and plastic microtiter plates, among others.

In one embodiment, the substrate element 672 comprises a functional coating such as to enhance chemistry binding. This can be applied, for example, by wet chemistry or the like. In another embodiment, the substrate element 672 comprises a membrane.

In one embodiment, the substrate element 672 has a thickness of about 150 μm. In another embodiment, the substrate element 672 has a thickness in the range from about 100 μm to about 200 μm, including all values an sub-ranges therebetween. In yet another embodiment, the substrate element 672 has a thickness in the range from about 75 μm to about 300 μm, including all values an sub-ranges therebetween. In still another embodiment, the substrate element 672 has a thickness in the range from about 50 μm to about 400 μm, including all values an sub-ranges therebetween. In a further embodiment, the substrate element 672 has a thickness less than about 500 μm.

In some cases, substrates are provided with a functional coating, for example, to enhance chemistry binding. In one embodiment, this functional. coating is also conductive. Advantageously, the functional and conductive coating can be used for enhanced electrostatic bias dispensing.

Figure 22:
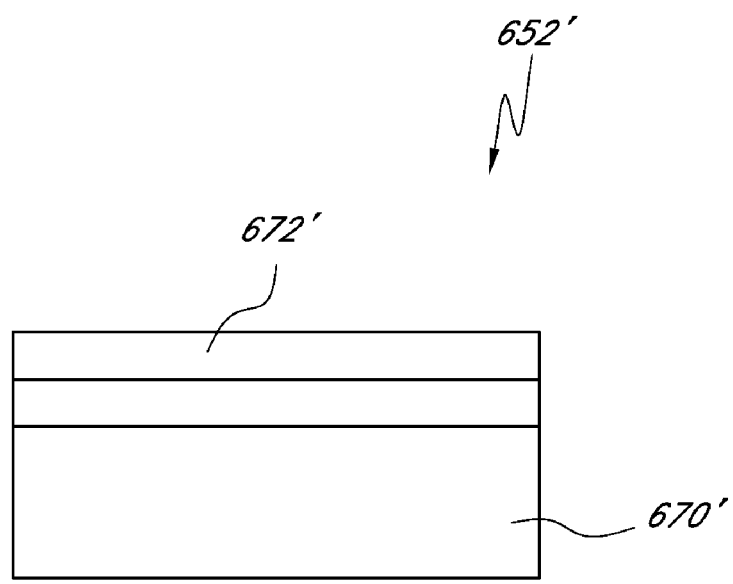
FIG. 22 is a simplified schematic view of a substrate assembly with a conductive layer or pattern having features and advantages in accordance with another embodiment of the invention.

FIG. 22 shows one embodiment of a substrate or substrate assembly 652' generally comprising a base or passive substrate element or portion 670' and an active or functional substrate element or portion 672' on which droplets are dispensed and which is also conductive for enhanced sub-microfluidic dispensing. In a modified embodiment, the substrate 652' may be constructed without the substrate element 670'. The substrate embodiment of FIG. 22 can be used in conjunction with any of the electric field embodiments as disclosed, taught or suggested herein.

The substrate element 670' typically comprise a dielectric material. For example, the substrate element 670' can comprise glass or plastic slides and plastic microtiter plates, among others.

In one embodiment, the substrate element or portion 672' comprises a conductive surface with a conductive pattern such as a circuit pattern where the conductive electrode pattern can be held at a particular and/or predetermined electrostatic or electric bias relative to the nozzle 36 and/or tip 34. In this embodiment, drops are dispensed on the electrode pattern such as in a biosensor or the like. This substrate embodiment can be used in conjunction with any of the electric field embodiments as disclosed, taught or suggested herein.

In some embodiments, dispensing onto surfaces with strong electric fields (in the kilovolt range) may have additional effects on molecular motion and binding reactions in the liquid state after dispensing. These effects could be beneficial and/or controllable and typically would depend on the particular application or use. Advantageously, using such strong electric fields during dispensing can provide effects of one or both of molecular distribution and binding reactions.

Some Dispensing System Arrangements

Any of the embodiments disclosed, taught or suggested herein can be used in conjunction with the arrangements, systems, methods, applications and uses as disclosed, taught or suggested in U.S. Pat. Nos. RE38,281 E, reissued Oct. 21, 2003, entitled DISPENSING APPARATUS HAVING IMPROVED DYNAMIC RANGE, and 6,063,339, issued May 16, 2000, entitled METHOD AND APPARATUS FOR HIGH-SPEED DOT ARRAY DISPENSING, U.S. Patent Application Publication No. US 2002/0159919 A1, published Oct. 31, 2002 (U.S. patent application Ser. No. 09/945,388, filed Aug. 30, 2001), copending U.S. patent application Ser. No. 10/765,001, filed Jan. 26, 2004, both entitled METHOD AND APPARATUS FOR HIGH-SPEED MICROFLUIDIC DISPENSING USING TEXT FILE CONTROL, PCT International Patent Application Publication No. WO 03/072258 A1, published Sep. 24, 2003 (PCT International Patent Application No. PCT/US03/05569, filed Feb. 24, 2003), and copending U.S. patent application Ser. No. 10/373,254, filed Feb. 24, 2003, both entitled METHOD AND APPARATUS FOR DISPERSING REAGENT DROPLETS BELOW A FLUID SURFACE USING NON-CONTACT DISPENSING, the entirety of each one of which is hereby incorporated by reference herein.

U.S. Pat. Nos. 6,063,339, 5,916,524, 5,738,728, 5,743,960 and 5,741,554, the entirety of each one of which is hereby incorporated by reference, disclose the concept of a reagent dispensing apparatus and method in which a positive displacement syringe pump is used in combination with a liquid dispenser/actuator, such as a solenoid valve dispenser or piezoelectric dispenser, to achieve improved dispensing operations. The syringe pump meters a predetermined quantity or flow rate of reagent to the dispenser to regulate the quantity or flow rate of liquid reagent dispensed. Simultaneously, an associated X, X-Y or X-Y-Z table is controlled so as to move a substrate in coordinated relation with the dispenser operation such that the reagent density can be controlled, for example, in terms of volume of reagent deposited per unit length of substrate substantially independently of the particular flow characteristics of the liquid reagent or the particular operating parameters of the dispenser (within a given range).

Providing a positive displacement pump in series with the dispenser advantageously allows the quantity or flow rate of reagent to be controlled independently of the particular flow characteristics of the liquid being dispensed and/or the operating parameters of the particular dispenser. For example, the size of droplets formed by a dispenser can be adjusted by changing the operating frequency (for a solenoid valve or piezoelectric dispenser) or by adjusting the air pressure or exit orifice size (for an air brush dispenser) without affecting the flow rate of reagent. Also, the reagent flow rate can be controlled without substantial regard to the system operating parameters otherwise required to achieve stable dispensing operations. The quantity or flow rate of reagent dispensed is controlled or regulated independently by the positive displacement pump.

U.S. Patent Application Publication No. US 2002/0159919 A1, published Oct. 31, 2002 (U.S. patent application Ser. No. 09/945,388, filed Aug. 30, 2001), and copending U.S. patent application Ser. No. 10/765,001, filed Jan. 26, 2004, both entitled METHOD AND APPARATUS FOR HIGH-SPEED MICROFLUIDIC DISPENSING USING TEXT FILE CONTROL, the entirety of each one of which is hereby incorporated by reference, disclose the concept of a method and apparatus for dispensing reagents and other liquids onto a target or substrate and, in particular, a method and apparatus for high-speed precision dispensing, controlled by input data from a user-defined text file, of multiple chemical or biological reagents with the ability to dispense a wide dynamic range of dispense volumes in complex combinatorial patterns, ratios and arrays onto or into a high-density microwell plate, glass slide, receptive membrane, test strip, vial or other suitable target.

In some embodiments, the system operation is controlled by data accessed from a customized user-defined text file. Advantageously, the use of such text file control allows high-speed precision dispensing of one or more reagents with a wide dynamic range of dispense volumes in complex combinatorial patterns, ratios and arrays onto or into multiple predetermined locations of a desired target or substrate. This is particularly advantageous when a large number of permutations of different reagent and permutations of reagent volume ratios are involved. In some embodiments, the systems are operated in a high frequency modulated mode to further improve accuracy and reliability.

PCT International Patent Application Publication No. WO 03/072258 A1, published Sep. 24, 2003 (PCT International Patent Application No. PCT/US03/05569, filed Feb. 24, 2003), and copending U.S. patent application Ser. No. 10/373,254, filed Feb. 24, 2003, both entitled METHOD AND APPARATUS FOR DISPERSING REAGENT DROPLETS BELOW A FLUID SURFACE USING NON-CONTACT DISPENSING, the entirety of each one of which is hereby incorporated by reference herein, relate to methods and systems of dispersing, suspending or arranging microfluidic or sub-microfluidic volumes of droplets of chemical, biological or other reagents or liquids below the surface of a cover or host fluid using non-contact dispensing for creating an assay or reaction that produces a detectable signal or a by-product such as a harvestable protein crystal. Advantageously, evaporation of valuable reagents is substantially prevented or reduced. Another advantage, in the case of miscible reagents, is that the drop velocities provide good mixing. Yet another advantage is that, in the non-contact dispensing scheme, the nozzle or tip is not immersed into the host fluid, thereby facilitating cleaning.

FIGS. 23-32 show some dispensing systems and components. Any of the embodiments disclosed, taught or suggested herein can be efficaciously used in conjunction with the arrangements of FIGS. 23-32.

Figure 23:
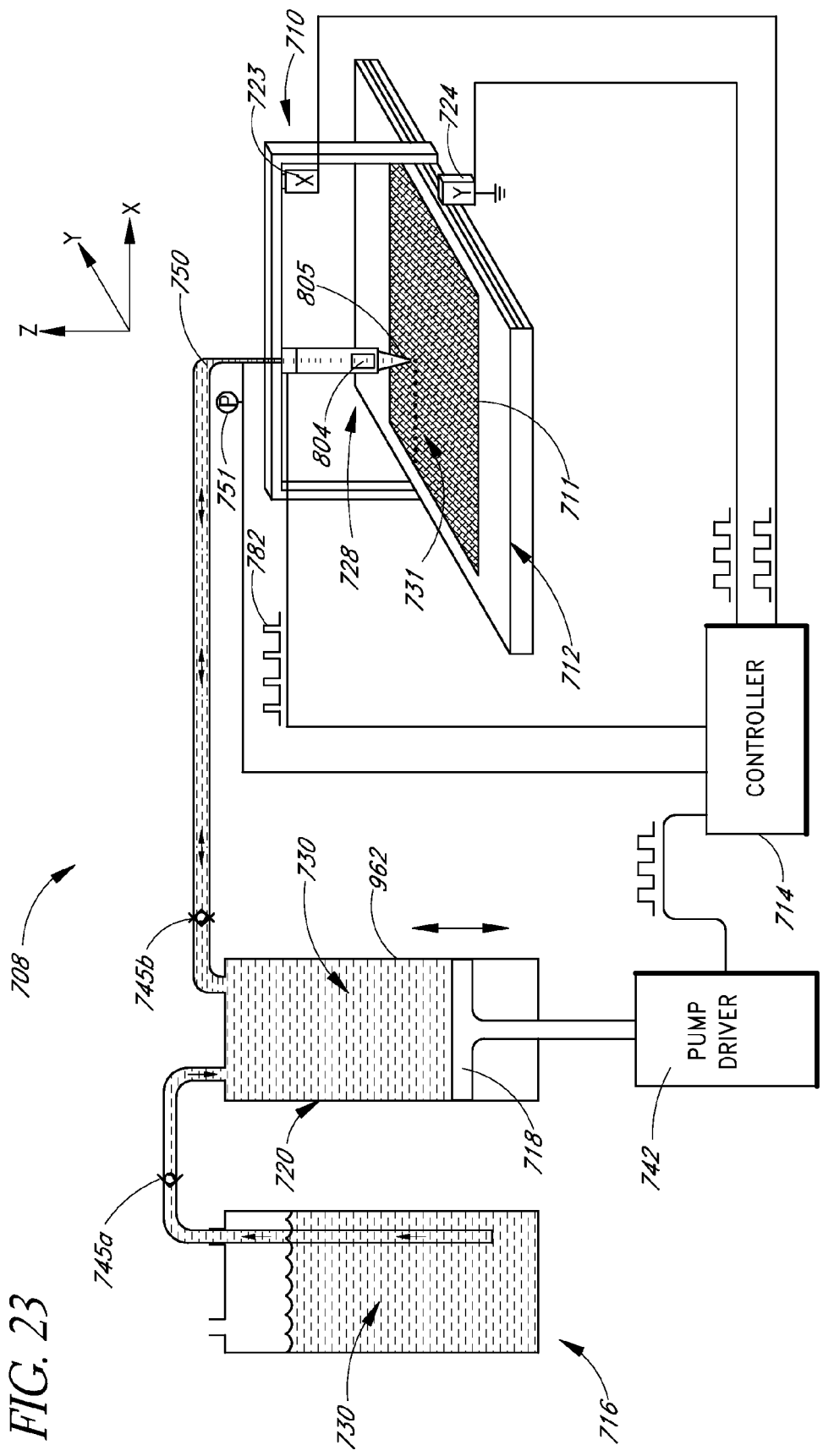
FIG. 23 is a simplified view of a dispensing apparatus having features and advantages in accordance with one embodiment of the invention.

FIG. 23 illustrates one embodiment dispensing apparatus 708 having certain features and advantages in accordance with one embodiment. The dispensing apparatus 708 is particularly adapted for automated high-speed precision dispensing (and aspirating) of liquids such as chemical and biological reagents, for example, DNA, cDNA, RNA, proteins, peptides, oligonucletides, other organic or inorganic compounds, among others.

The dispensing apparatus 708 generally comprises a dispensing head or dispenser 728 having a valve or other dispensing means 804 operated by an actuator, such as a solenoid. The dispenser 728 is hydraulically coupled or in fluid communication with a positive displacement pump 720 for metering precise quantities of fluid or liquid 730 to or towards the dispenser 728. The dispenser 728 is mounted on or in association with an X-Y table or gantry 710.

As shown in FIG. 23, a substrate or target 711 is mounted on a carrier platform, table or carriage 712 to receive reagent or liquid dispensed from the dispenser 728. The target 711 can comprise one or more microtiter plates, glass slides, receptive membranes, test strips, or other suitable porous or non-porous targets such as one or more single-well receptacles, vials or tubes. The microtiter plates can be configured in 96, 384, 1536 and 2080 well plate formats, among other configurations.

Those skilled in the art will appreciate that the X-Y table 710 (FIG. 23) may include one or more position stepper motors 723, 724 or the like, which are operable to move either the dispenser 728 and/or the carrier platform or table 712 relative to one another in the X, X-Y or X-Y-Z directions, as indicated in the drawing. Alternatively, or in addition, one or more suitable robot arms may be efficaciously used, as needed or desired, to provide controlled relative motion between the dispenser 728 and the target substrate 711 and/or other components or associated components of the apparatus 708.

Though FIG. 23 shows only a single dispenser 728, in other preferred embodiments, it is contemplated that multiple dispensers in linear (1×N) or two-dimensional (M×N) arrays are used. These may be provided and operated either in parallel or in another coordinated fashion, as desired. It should be understood that any discussion herein with specific reference to the single dispenser embodiment is substantially equally applicable, with possible modifications as apparent to the skilled artisan, to multiple dispensers each connected to respective pumps or a single pump.

The positive displacement pump 720, in one embodiment, comprises a syringe pump though other direct current (DC) fluid sources may be used with efficacy. The syringe pump 720 is hydraulically coupled to or in fluid communication with a fluid reservoir 716 through a first one-way check valve or open-close valve 745a. The syringe pump 720 draws fluid 730 from the fluid reservoir 716 and provides it to the dispenser 728 through a second check valve or open-close valve 745b on a supply line or feedline 750.

The syringe pump 720 7 has a movable piston 718 within a syringe barrel 962. The syringe pump 720 is operated by a syringe pump driver 742 comprising, for example, a stepper motor and an associated lead screw, for extending and retracting the piston 718 within the syringe barrel 962. Those skilled in the art will readily appreciate that when the piston 718 is retracted, fluid 730 is drawn from the reservoir 716 into the syringe pump 720. When the piston 718 is again extended, fluid 730 is forced to flow from the syringe barrel 962 into the dispenser 728 via the supply tube 750, whereupon it is ejected by the dispenser 728 onto or into the target substrate 711 in the form of droplets 731 or a spray pattern.

In one embodiment, the fluid or liquid 730 comprises the reagent that is dispensed onto or into the target 711. That is the system (reservoir 716, pump barrel 962, dispenser 728 and other connection lines) is filled with the reagent 730 to be dispensed. This set-up is particularly advantageous when relatively large quantities of the same reagent are to be dispensed.

In another embodiment, the fluid or liquid 730 comprises a system fluid or backing reagent, such as distilled water, and the dispensing apparatus 708 operates in a "suck-and-spit" mode. In this embodiment, the dispenser 728 is used to aspirate a predetermined amount of fluid, liquid or reagent from a source receptacle or microtiter plate and the like and then dispense the aspirated reagent onto or into the target 711. As the skilled artisan will appreciate, reagent is aspirated by retracting or decrementing the pump piston 718 with the valve 745b open to create a reduced pressure or partial vacuum to draw source reagent into the dispenser 728 via a suitable tip or nozzle thereon.

A controller 714 oversees operation of the pump 720, X-Y table 710 (or X, or X-Y-Z table) and the dispenser 728, among other associated components. The controller 714 coordinates and controls the motion of each of the stepper motors 723, 724, and the syringe pump driver 742, as well as the opening and closing of the dispensing valve 804 to precisely dispense an amount of reagent at one or more predetermined location (s) on or in the target substrate 711. The controller 714 also controls and coordinates aspiration of source reagent, as and if needed.

A computer software program is interfaced with the controller 714 to guide dispensing (and/or aspirating) for different modes of operation and different applications. In one embodiment, a user-defined text file is created, for example, from a spreadsheet of values or template, with lists of numbers of user-defined dispense volumes of one or more reagents and corresponding coordinates of the dispense (and/or aspirate) operation. The controller 714 uses this text file data in cooperation with the software program to precisely control and coordinate the operation of the dispensing apparatus 708.

Advantageously, the use of such text file control allows high-speed precision dispensing of one or more reagents with a wide dynamic range of dispense volumes in complex combinatorial patterns, ratios and arrays onto or into multiple predetermined locations of a desired target or substrate. This is particularly advantageous when a large number of permutations of different reagent and permutations of reagent volume ratios are involved. In such cases, typically, more than one dispenser (see FIGS. 24 and 25) or a manifold system (see FIG. 26) or a combination thereof is utilized to facilitate process efficiency. These multiple dispensers can be operated in parallel or in synchronous coordination.

Figure 24:
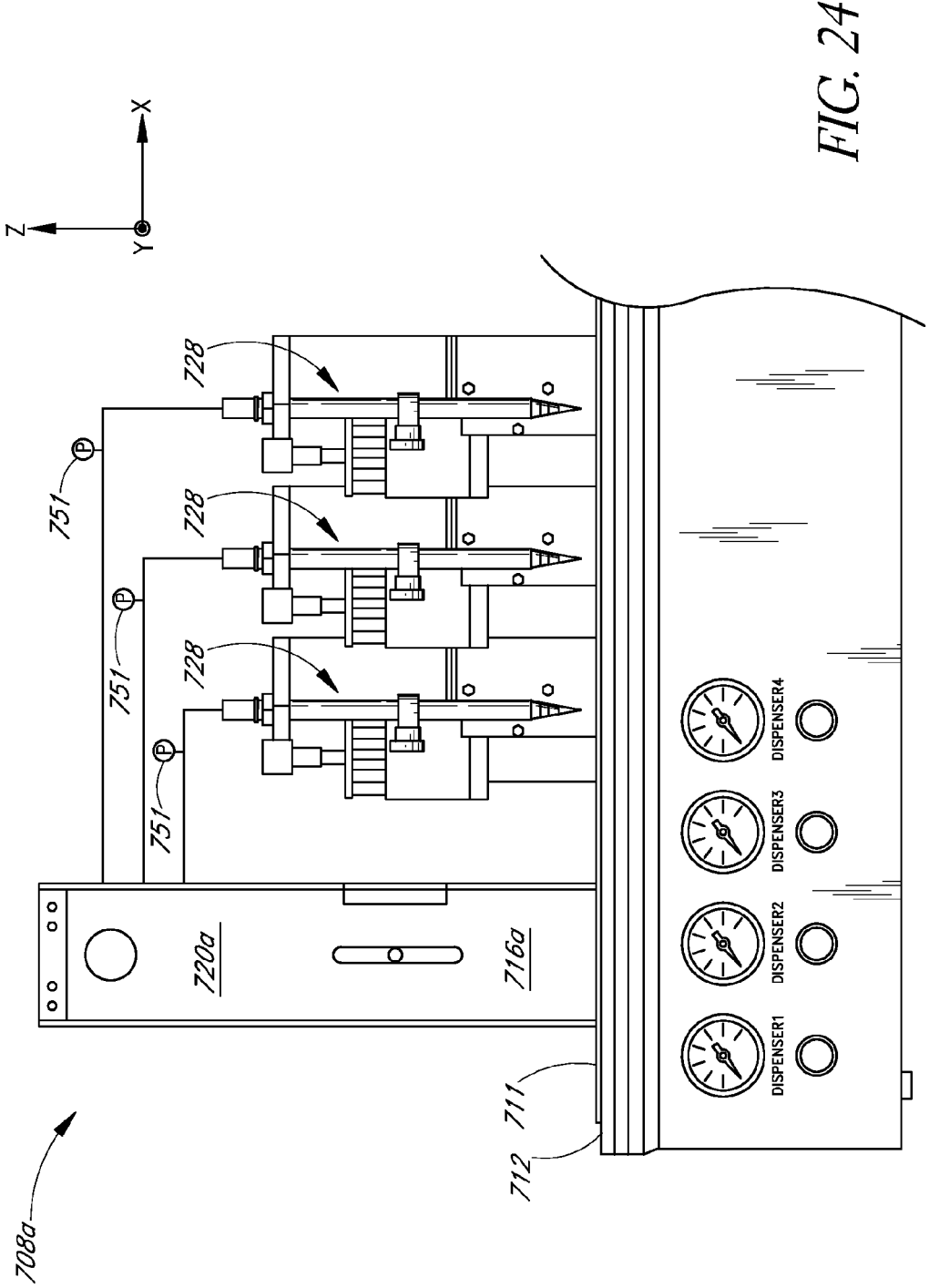
FIG. 24 is a simplified view of a dispensing apparatus with multiple dispensers having features and advantages in accordance with one embodiment of the invention.

FIG. 24 shows a dispensing apparatus 708a comprising a plurality of dispensers 728. As has been described above in reference to FIG. 23, each dispenser 728 is connected to a respective pump 720 (in FIG. 24, the pumps 720 are part of a pump bank 720a and a reservoir bank 716a comprises the reservoirs 716). A single reagent may be dispensed by all of the dispensers 728 or multiple reagents, as needed or desired. Moreover, reagent(s) can be first aspirated and then dispensed, as discussed above.

Still referring in particular to FIG. 24, relative motion is provided between the substrate or target 711 and the dispensing channels 728. The dispensers 728 and/or the platform 712 are movable in the X, X-Y or X-Y-Z directions to allow for precision dispensing at predetermined locations. Multiple targets 711 may be placed on the table 712, as needed or desired. The dispensers 728 can be independently moved or together in the form of a dispense head comprising multiple dispense channels 728 spaced from one another by predetermined distance(s). Moreover, the dispensers 728 can be individually (serially or sequentially) operated or substantially simultaneously (parallely) or a combination thereof, as needed or desired. A central or main controller, possibly in conjunction with sub-controllers, is used to control and coordinate the actuations of the pumps 720, dispensers 728 and relative movement between the target 711 and dispense channels 728.

Figure 25:
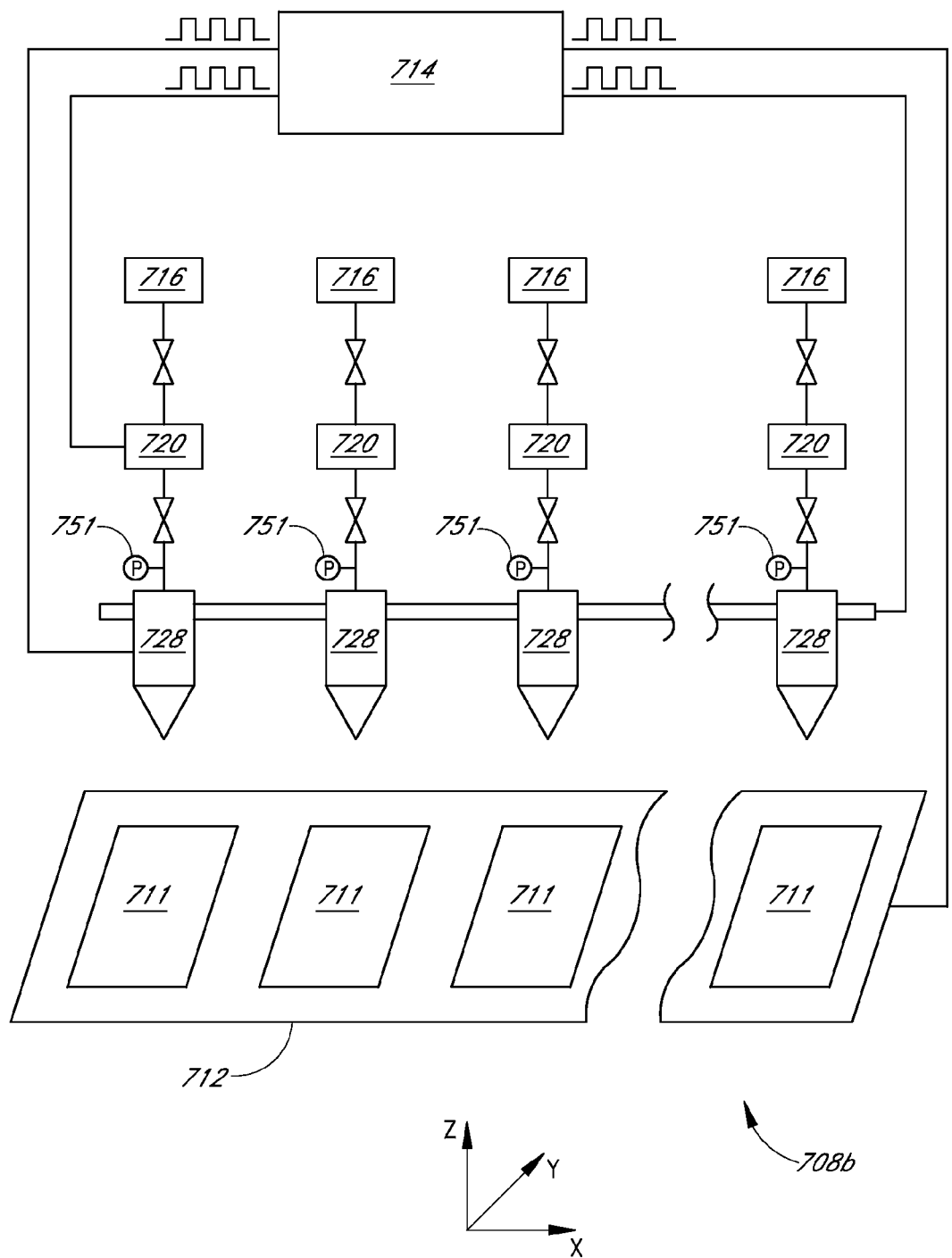
FIG. 25 is a schematic generalized illustration of a dispensing apparatus with an array of dispensers having features and advantages in accordance with one embodiment of the invention.

FIG. 25 shows a dispensing apparatus 708b comprising a plurality of dispensers 728. In general, the dispensing apparatuses described herein can comprise one or more dispensers 728 arranged in a wide variety of configurations such as linear (1×N), two-dimensional (M×N) or even three-dimensional (M×N×K) arrays. It should be noted that the array or collection of dispensers or dispenser heads 728 may be referred to as a "dispensing head" comprising multiple dispense channels 728.

Figure 26:
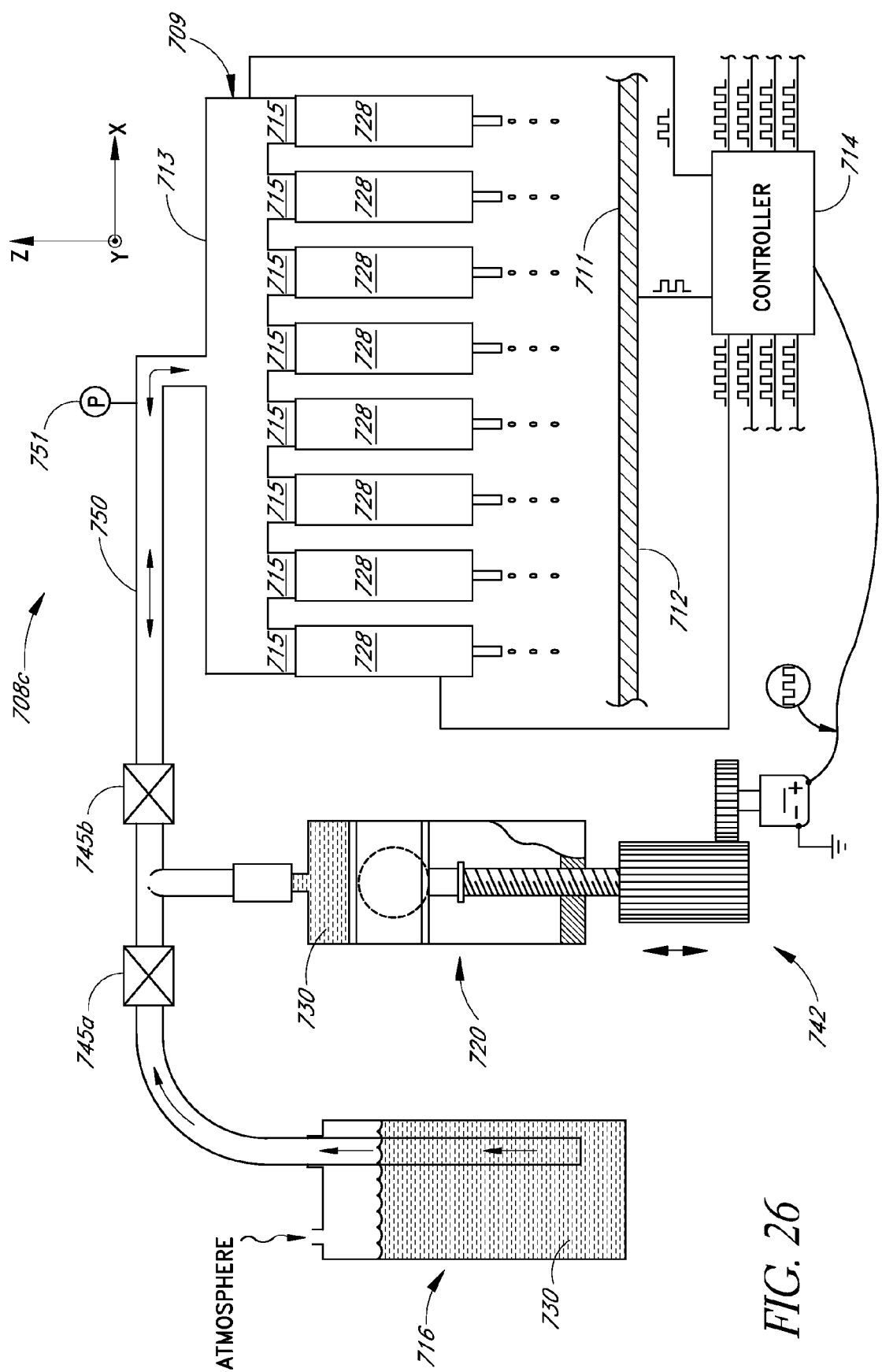
FIG. 26 is a simplified view of a dispensing apparatus with a manifold having features and advantages in accordance with one embodiment of the invention.

FIG. 26 shows a dispensing apparatus 708c comprising a manifold 709 connected to a plurality of dispensers 728. The manifold generally comprises a main supply line 713 in fluid communication (hydraulically coupled) with a plurality of independent channels 715 each of which is in fluid communication (hydraulically coupled) with a respective one of the dispensers 728. A positive displacement syringe pump 720 is in fluid communication (hydraulically coupled) with the manifold 709 via the feedline 750. Reagent(s) can be first aspirated and then dispensed or a single reagent may fill the system, as discussed above.

Still referring in particular to FIG. 26, relative motion is provided between the substrate or target 711 and the dispensing channels 728. The dispensers 728 and/or the platform 712 are movable in the X, X-Y or X-Y-Z directions to allow for precision dispensing at predetermined locations. Multiple targets 711 may be placed on the table 712, as needed or desired. The dispensers 728 are in the form of multiple dispense channels spaced from one another by predetermined distance(s). More than one manifold may be utilized, as needed or desired.

The dispensers 728 (FIG. 26) can be individually (serially or sequentially) operated or substantially simultaneously (parallely) or a combination thereof, as needed or desired. A linear (1×N) or two-dimensional (M×N) array of dispensers 728 may be used with efficacy. A central or main controller 714 is used to control and coordinate the actuations of the pump 720, dispensers 728 and relative movement between the target 711 and dispense channels 728. Some embodiments of a multi-channel aspirate-dispense system comprising a manifold are described in U.S. Patent Application Publication No. US 2003/0215957 A1, published Nov. 20, 2003 (copending U.S. patent application Ser. No. 10/445,625, filed May 7, 2003), entitled MULTI-CHANNEL DISPENSING SYSTEM, the entirety of which is hereby incorporated by reference herein.

Advantageously, and as shown in FIG. 26, the use of a manifold 709 allows only one pump 720 to meter fluid to and from a plurality of dispensers 728. Desirably, this saves on cost. Moreover, balanced and controlled output can be achieved by adjusting the frequency and/or duty cycle of one or more of the dispensers 728 to compensate for any variations in flow resistances between channels.

Solenoid Valve Dispenser

Figure 27:
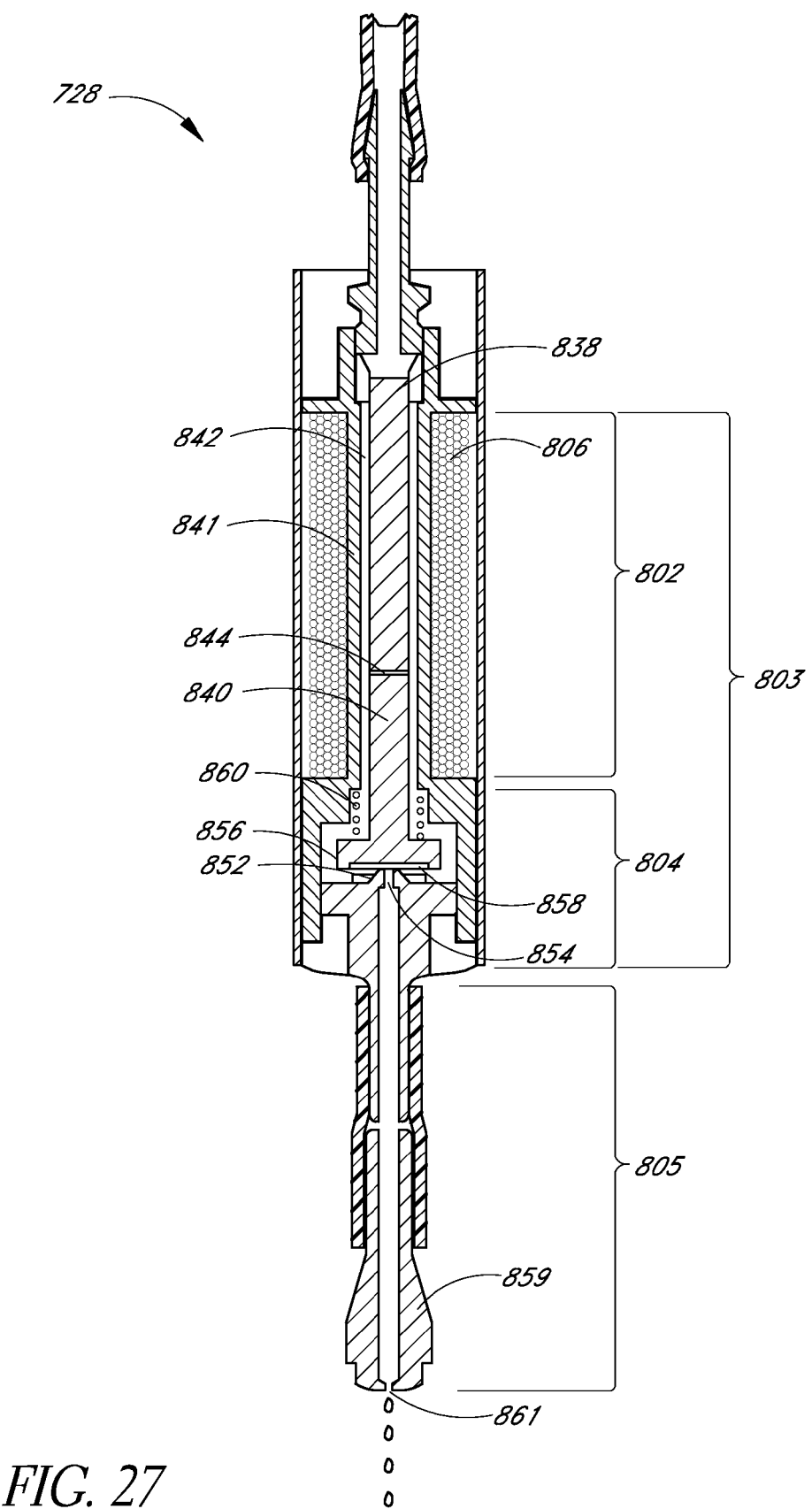
FIG. 27 is a simplified cross-sectional view of a solenoid valve dispensing head having features and advantages in accordance with one embodiment of the invention.

FIG. 27 shows one embodiment of a solenoid valve dispensing head 728 for use with the dispensing (and/or aspiration) systems as described herein. Solenoid valve dispensers of the type shown in FIG. 27 are commonly used for ink-jet printing applications and are commercially available from sources such as The Lee Company of Westbrook, Conn. Other suitable drop-on-demand dispensers, actuators and valves may be efficaciously used, as needed or desired.

The drop-on-demand dispenser 728 (FIG. 27) generally comprises a solenoid portion 802, a valve portion 804 and a tube, capillary, tip or nozzle portion 805. The solenoid portion 802 and the valve portion 804 in combination can be termed a drop-on-demand valve, a solenoid-actuated valve or a micro-solenoid valve 803. The tip 805 may be considered part of the dispenser 728 or a separate component.

The solenoid portion 802 comprises an electromagnetic coil or winding 806, a static core 838 and a movable plunger 840. The static core 838 and movable plunger 840 are disposed within a hollow cylindrical sleeve 841 and are preferably spaced at least slightly away from the inner walls of the sleeve 841 so as to form an annular passage 842 there between through which the reagent 730 or other liquid to be dispensed may flow. The static core 838 and movable plunger 840 are in one embodiment, formed of a ferrous or magnetic material, such as an iron alloy, and are separated by a small gap 844. Those skilled in the art will appreciate that when the solenoid coil 806 is energized, for example by a current or voltage, a magnetic field is created which draws the plunger 840 upward toward the static core 838, closing the gap 844 and opening the valve 834.

The valve portion 804 comprises a valve seat 852, having an orifice opening 854, and a stopper 856 having a valve face 858 adapted to seal against the valve seat 852. The stopper 856 is in electromechanical communication with the plunger 840 and is spring biased toward the valve seat 852 via coil spring 860. Again, those skilled in the art will readily appreciate that as the plunger 840 moves up and down, the valve 834 will open and close, accordingly, hence providing selective fluid communication with the tip 805. Moreover, each time the valve 834 opens and closes, a volume of liquid is allowed to escape through the valve orifice 854. This, in conjunction with the metering of fluid by the pump 720, forms an energy pulse or pressure wave which causes a droplet of liquid to be ejected from the exit orifice 861 of the nozzle tip 859.

As indicated above, in one embodiment, the pump 720 (see, for example, FIG. 23) is a positive displacement pump and is provided in series with the solenoid valve dispenser 728. Configuring the dispensing system in this manner has the benefit of forcing the solenoid valve dispenser 728 to admit and eject a quantity and/or flow rate of reagent as determined solely by the positive displacement pump 720, with which it is hydraulically in series. For example, the syringe pump could be instructed to deliver a flow rate of 1 microliter per second of reagent to the solenoid valve dispenser 728 at a steady rate. As the valve stopper 856 is opened and closed at a given frequency and duty cycle a series of droplets are formed which will exactly match the desired flow rate. The syringe pump acts as a forcing function for the entire system, ensuring that the desired flow rate is maintained regardless of the duty cycle or frequency of the dispensing valve.

Advantageously, within a certain operating range the frequency and/or velocity of the droplets can be adjusted without affecting the flow rate of reagent simply by changing the frequency and/or duty cycle of the energizing pulses 782 (FIG. 23) provided to the solenoid valve dispenser 728. Of course, there are physical limitations of valve open time or duty-cycle necessary to achieve stable droplet formation. If the open time is too short relative to the flow rate, the pressure will increase and possibly prevent the valve dispenser 728 from functioning properly. If the open time is too long relative to the flow rate, then drop formation may be impaired or may not be uniform for each open/close cycle. Nevertheless, for a given flow rate of reagent 730 provided by the syringe pump 720 there will be a range of compatible frequencies and/or valve open times or duty-cycles in which stable dispensing operations may be achieved at the desired flow rate and droplet size. This range may be determined experimentally for a given production set up.

Some embodiments of a solenoid actuated dispenser are described in U.S. Pat. No. 6,537,505 B1, issued Mar. 25, 2003, entitled REAGENT DISPENSING VALVE, the entirety of which is hereby incorporated by reference herein.

Those skilled in the art will recognize that other types of dispensers and valve actuation devices exist and may be used with efficacy. These may include, for example, but are not limited to piezoelectric dispensers, fluid impulse dispensers, heat actuated dispensers, air brush dispensers, and the like.

Figure 28:
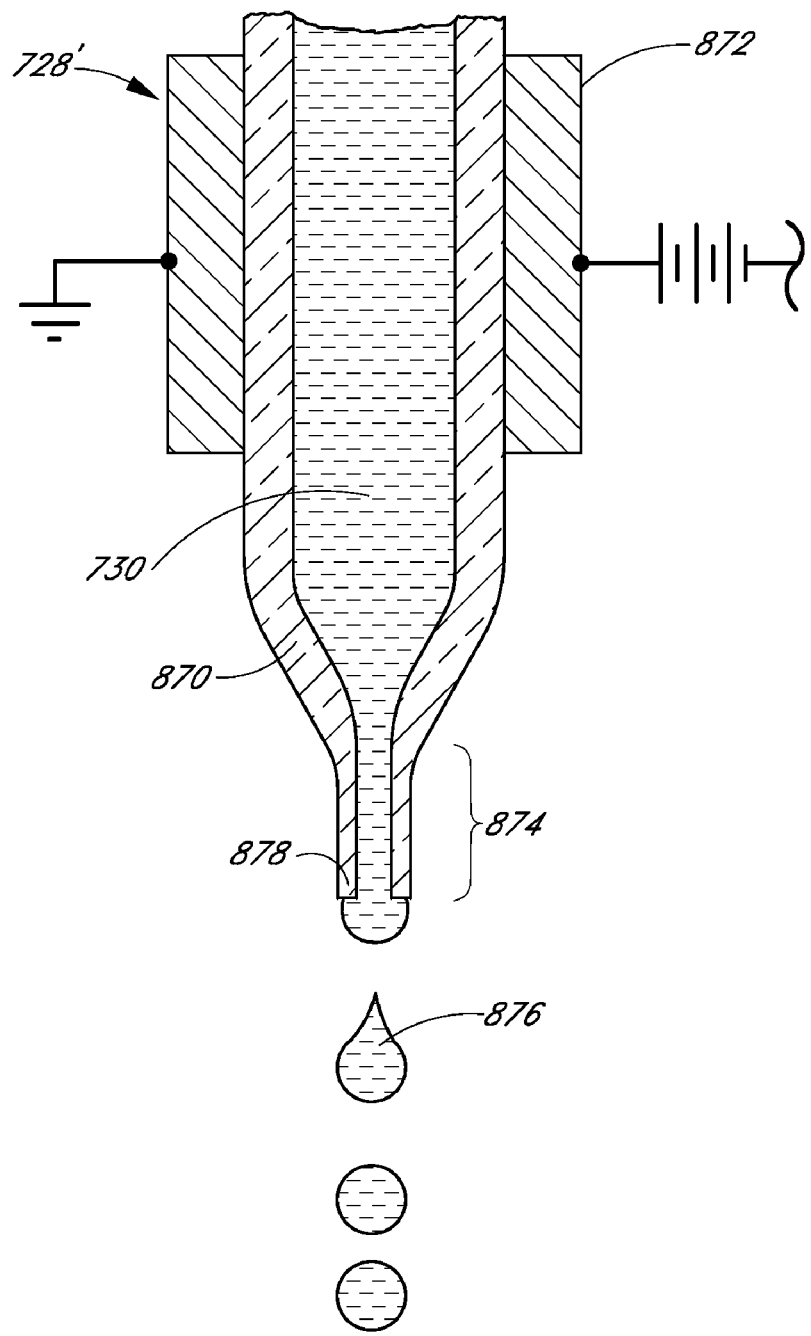
FIG. 28 is a simplified cross-sectional view of a piezo electric dispensing head having features and advantages in accordance with one embodiment of the invention.

FIG. 28 shows a cross-sectional view of a piezoelectric dispenser 728' which also has advantageous use in accordance with embodiments of the invention. The piezoelectric dispenser 728' generally comprises a capillary tube 870 made of glass or other suitable material and a piezoelectric constrictor 872 disposed around the capillary tube 870, as shown. The capillary tube 870 has a nozzle portion 874 of a reduced diameter. When the capillary tube 870 is constricted by the piezoelectric constrictor 872, droplets 876 are formed at the exit orifice 878 of the nozzle portion 874. Advantageously, the dynamics of the piezoelectric dispenser 728' are such that it may be able to operate at even higher frequencies and shorter duty cycles than typical solenoid valve dispensers, resulting in even smaller droplets 876. Operation of the piezoelectric dispenser 828' in terms of adjusting droplet size, frequency, velocity and flow rates is substantially the same or similar to that described in connection with the solenoid valve dispenser 828 of FIG. 27 and, therefore, will not be repeated here.

Figure 30:
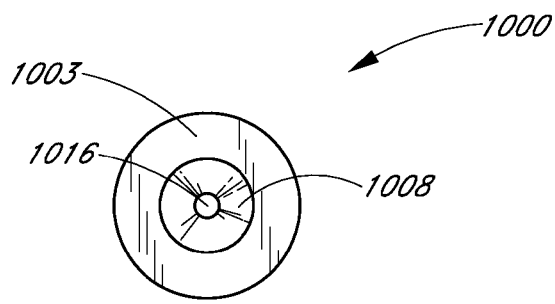
FIG. 30 is a simplified top view of the tip of FIG. 29.
Figure 29:
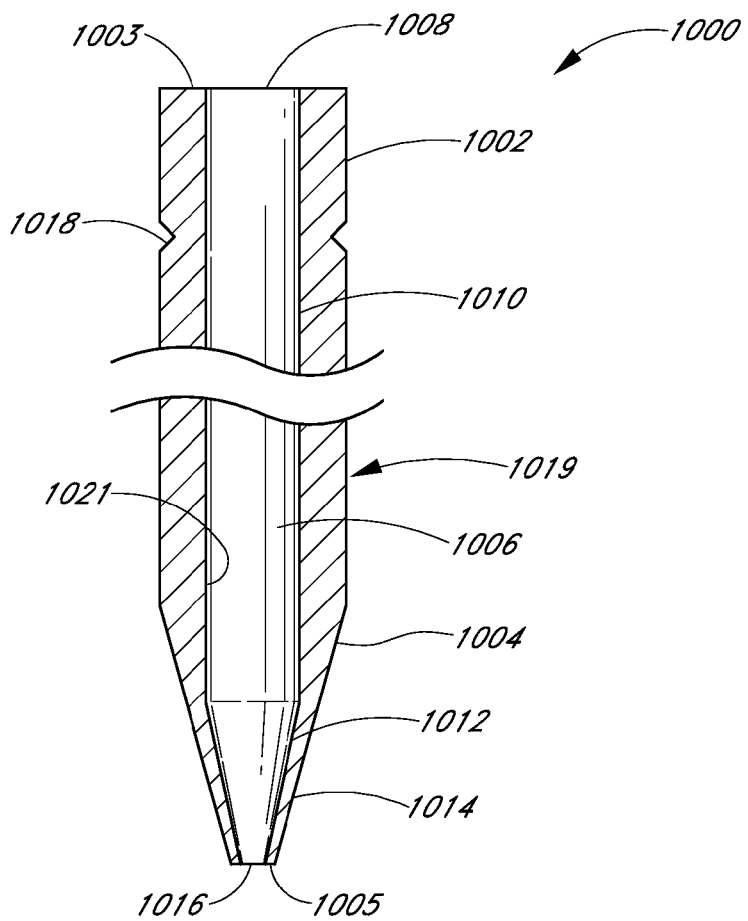
FIG. 29 is a simplified cross-sectional view of a dispensing tip having features and advantages in accordance with one embodiment of the invention.
Figure 31:
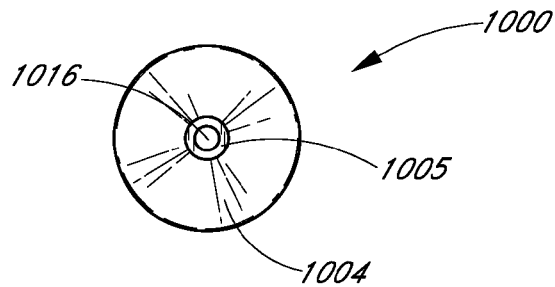
FIG. 31 is a simplified bottom view of the tip of FIG. 29.

FIGS. 29-31 show different views of a non-contact dispensing capillary tip or tube 1000 having features and advantages in accordance with one embodiment of the invention. The dispensing tip 1000 may be incorporated into any of the dispensing systems disclosed, taught or suggested herein. Some embodiments of such tips are disclosed in U.S. Pat. No. 6,551,557 B1, issued Apr. 22, 2003, entitled TIP DESIGN AND RANDOM ACCESS ARRAY FOR MICROFLUIDIC TRANSFER, the entirety of which is hereby incorporated by reference herein.

In the illustrated embodiment of FIGS. 29-31, the tip 1000 is generally cylindrical in shape and comprises a non-tapered upper portion or shank 1002 with an upper proximal end 1003, a tapered lower portion/outer surface 1004 with a lower distal end 1005 and an inner lumen or through cavity 1006. The inner lumen 1006 is generally cylindrical in shape with a top opening 1008, a non-tapered upper portion 1010, and a tapered lower portion/inner surface 1012 to form a nozzle 1014 having a drop emitting orifice or opening 1016. Advantageously, the outer taper 1004 leads to less accumulation of fluid on the tip outer surface, for example, during aspiration. Also, advantageously, the inner taper 1012 is a desirable shape for capillary action, and reduces fluid mixing during aspiration and reduces the precipitation of gaseous bubbles within the fluid during aspirate-dispense operations.

Optionally, as shown in FIG. 29, the tip 1000 may further include a generally circumferential groove, slot or notch 1018 on the non-tapered upper portion 1002. The slot 1018 is generally V-shaped. The notch 1018 advantageously provides an easy break point in the case of accidental hard or jarring contact between the tip 1000 and a contacting surface of the fluid source or target.

The tip 1000 is desirably fabricated from a ceramic material, and, in one embodiment, from alumina. Advantageously, the ceramic material provides chemical inertness since alumina is inert to most chemical solvents. Moreover, the ceramic material provides robustness, and hence can withstand extreme mechanical stress. In other embodiments, the tip 1000 can be fabricated from a wide variety of materials with efficacy such as metals, alloys, and plastics, as required or desired, giving due consideration to the goals of providing chemical inertness and robustness.

In one embodiment, the outer surface 1019 of the tip 1000 is coated with a thin film or coating that is not only chemically inert and mechanically robust but is also hydrophobic to most fluids such as aqueous reagents, DMSO, and other common solvents. The film helps in keeping the tip 1000 dry and also improves the microfluidic or sub-microfluidic transfer. In one embodiment, the film comprises a wear-resistant material so that it has an enhanced lifetime. Suitable films or coatings include silicon nitride, silicon carbide, titanium nitride, among others. The film or coating can be applied by a variety of methods such as plasma deposition and sputtering, among others, as is known in the art. A suitable hydrophobic coating may also be applied to selected portions of the inner surface 1021 of the tip 1000, as needed or desired.

The tip 1000 may be dimensioned in a wide variety of manners with efficacy, as required or desired, giving due consideration to the goals of providing reliable and repeatable microfluidic and sub-microfluidic transfer of fluid. In one embodiment, the tip 1000 has a length of 16 mm and an internal volume of about 20 microliters (μL). In some embodiments, the inner diameter at the nozzle end of the tip 1000 is in the range from about 20 to 180 microns (μm) and the outer diameter is in the range from about 50 to 400 μm or more. In other embodiments, the inner diameter at the nozzle end of the tip 200 is in the range from about 100 to 300 μm and the outer diameter is in the range from about 400 to 900 μm.

Syringe Pump

Figure 32:
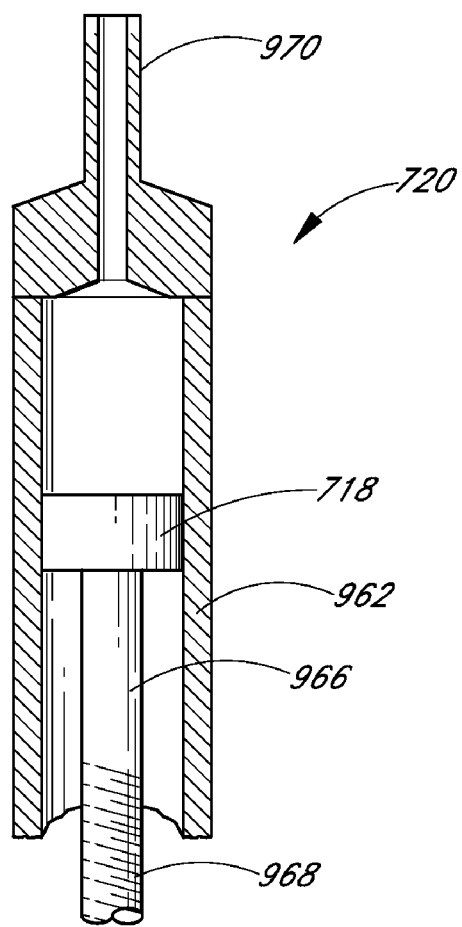
FIG. 32 is a simplified cross-sectional view of a positive-displacement syringe pump having features and advantages in accordance with one embodiment of the invention.

Referring in particular to FIGS. 23 and 32, the pump 720, in one embodiment, is a high-resolution, positive displacement syringe pump hydraulically coupled to the dispenser 728. Alternatively, pump 720 may be any one of several varieties of commercially available pumping devices for metering precise quantities of liquid. A syringe-type pump 720 can be advantageous because of its convenience and commercial availability. A wide variety of other direct current fluid source means may be used, however, to achieve the benefits and advantages as disclosed herein. These may include, without limitation, rotary pumps, peristaltic pumps, squash-plate pumps, and the like, or an electronically regulated fluid current source.

As illustrated in FIG. 32, one suitable syringe pump 720 generally comprises a syringe housing 962 of a predetermined volume and a plunger 718 which is sealed against the syringe housing by O-rings or the like (not shown). The plunger 718 mechanically engages a plunger shaft 966 having a lead screw portion 968 adapted to thread in and out of a base support (not shown). Those skilled in the art will readily appreciate that as the lead screw portion 968 of the plunger shaft 966 is rotated the plunger 718 will be displaced axially, forcing reagent 730 from the syringe housing 962 into the exit tube 970. Any number of suitable motors or mechanical actuators may be used to drive the lead screw 968. In one embodiment, a pump driver 742 including a stepper motor (FIG. 23) or other incremental or continuous actuator device is used so that the amount and/or flow rate of reagent 730 can be precisely regulated.

Several suitable syringe pumps are commercially available. One such syringe pump is the Bio-Dot CV1000 Syringe Pump Dispenser, available from BioDot, Inc. of Irvine, Calif. This particular syringe pump incorporates an electronically controlled stepper motor for providing precision liquid handling using a variety of syringe sizes. The CV1000 is powered by a single 24 DC volt power supply and is controlled via an industry-standard RS232 or RS485 bus interface. The syringe pump may have anywhere from 3,000-24,000 steps, although higher resolution pumps having 48,000-192,000 steps or more may also be with efficacy. Higher resolution pumps, such as piezoelectric motor driven pumps, may also be used to provide even finer resolutions as desired.

The lead screw 968 (FIG. 32) may optionally be fitted with an optical encoder or similar device to detect any lost steps. Alternatively, the lead screw of the metering pump can be replaced with a piezoelectric slide to provide both smaller volume increments and also faster acceleration/deceleration characteristics. Multiple syringe pumps may also be used in parallel, for example, for delivering varying concentrations of reagent 730 and/or other liquids to the dispenser or for alternating dispensing operations between two or more reagents. This could have application, for instance, to ink jet printing using one or more colored inks or liquid toners.

Syringe size may vary from less than 50 microliters (μL) to 50 milliliters (mL), or more as needed. The minimum incremental displacement volume of the pump will depend on the pump resolution and syringe volume. For example, for a syringe housing volume of 50 μL and 192,000 step resolution pump the minimum incremental displacement volume will be about 0.260 nanoliters (nL). Minimum incremental displacement volumes from about 0.25 nanoliters to about tens of milliliters (mL) are preferred, although higher or lower incremental displacement volumes may also be used while still enjoying the benefits disclosed, taught or suggested herein.

Of course, a wide variety of other positive displacement or "direct current" fluid sources may also be used to achieve the benefits and advantages as disclosed herein. These may include, for example and without limitation, rotary pumps, peristaltic pumps, squash-plate pumps, pumps incorporating hydraulic or electronic feedback control and the like.

In one embodiment, one or more pressure sensors 751 are provided in conjunction with the aspirate-dispense apparatuses 708 (FIG. 23), 708a (FIG. 24), 708b (FIG. 25) and 708c (FIG. 26) to monitor the system pressure and provide diagnostic information about various fluid and flow parameters within the hydraulic system. The pressure sensors 751 may be used in conjunction with any of the embodiments as disclosed, taught or suggested herein.

The one or more pressure sensors 751 are provided at appropriate locations on the respective systems. In one embodiment, the pressure sensors 751 are placed intermediate the syringe pump(s) 720 and the dispenser(s) 728, such as on the feedline 750 (see, for example, FIG. 23). Alternatively, or in addition, the pressure sensor(s) 751 can be situated at the dispenser(s) 728 such as on the valve portion(s) 804.

In one embodiment, for an aspirate function a system pressure close to or below zero is preferred, while for a dispense function a finite and positive predetermined steady state pressure is preferred. The one or more pressure sensors 751 facilitate in achieving these pressures.

A discussion of the theoretical predicted behavior and theoretical flow models relating to positive displacement dispensing and aspirating systems, some embodiments of pressure compensation or adjustment, for example, prior to dispense and aspirate functions, and some embodiments of methods for estimating steady state dispense pressure are disclosed in U.S. Patent Application Publication No. US 2003/0207464 A1, published Nov. 6, 2003 (copending U.S. patent application Ser. No. 10/443,699, filed May 23, 2003), entitled METHODS FOR MICROFLUIDIC ASPIRATING AND DISPENSING, U.S. Patent Application Publication No. US 2003/0215957 A1, published Nov. 20, 2003 (copending U.S. patent application Ser. No. 10/445,625, filed May 7, 2003), entitled MULTI-CHANNEL DISPENSING SYSTEM, and U.S. Pat. No. 6,589,791 B1, issued Jul. 8, 2003, entitled STATE-VARIABLE CONTROL SYSTEM, the entirety of each one of which is hereby incorporated by reference herein.

The methods which are described and illustrated herein are not limited to the sequence of acts described, nor are they necessarily limited to the practice of all of the acts set forth. Other sequences of acts, or less than all of the acts, or simultaneous occurrence of the acts, may be utilized in practicing embodiments of the invention.

From the foregoing description, it will be appreciated that a novel approach for microfluidic and sub-microfluidic dispensing has been disclosed. While the components, techniques and aspects of the invention have been described with a certain degree of particularity, it is manifest that many changes may be made in the specific designs, constructions and methodology herein above described without departing from the spirit and scope of this disclosure.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the appended claims, including the full range of equivalency to which each element thereof is entitled.

What is claimed is:

1. A method of accurately dispensing sub-microfluidic droplets of a liquid onto or into a target supported on a table, comprising:

providing a dispensing system comprising a substantially inert fluid path and a dispensing tip having a nozzle and a droplet emitting orifice at a distal end;

generating an electric field between said tip and said table by maintaining said tip at a first potential and said table at a second potential;

positively displacing said liquid through said tip to dispense droplets onto or into said target with said electric field providing a bias that facilitates droplet ejection and release from said tip so that droplets having a volume of less than about one microliter are reliably dispensed; and flowing ionized air over said nozzle to induce a hydrophobic effect.

2. The method of claim 1, wherein said electric field provides a gradient substantially parallel to the intended droplet trajectory.

3. The method of claim 1, wherein said method further comprises providing a ring electrode at a third potential and positioned intermediate said tip and said target and/or table.

4. The method of claim 3, wherein said method further comprises adjusting said first, second and third potentials to control droplet impact velocity on said target.

5. The method of claim 3, wherein said first and said second potentials are substantially the same while said third potential is lower so that droplet impact velocity is substantially a function of ejection velocity.

6. The method of claim 3, wherein said first potential is lower than said second potentials while said third potential is lower than both so that droplet impact velocity is reduced compared to that without any electric field.

7. The method of claim 1, wherein said electric field perturbs the fluid meniscus at said orifice to form a Taylor cone and said method further comprises applying a superimposed positive displacement pulse to aid in ejection of said droplets from said orifice.

8. The method of claim 1, wherein said method further comprises maintaining a voltage difference between said nozzle and said liquid therein.

9. The method of claim 8, wherein said nozzle has an outer surface coated with a conductive layer except for a portion at said distal end of said tip.

10. The method of claim 1, wherein said method further comprises controlling the surface charge on said target.

11. The method of claim 1, wherein a hydraulic source positively displaces said liquid.

12. The method of claim 1, wherein a pneumatic source positively displaces said liquid.

13. The method of claim 1, wherein said droplets have a volume less than about 100 nanoliters.

14. The method of claim 1, wherein said electric field is in the range from about 0.5 kV to about 5 kV.

15. The method of claim 3, wherein said ring electrode is integrated with said tip.

16. The method of claim 3, wherein said ring electrode is movable from under said tip.

17. The method of claim 1, wherein positive displacement pulses provide said liquid to said tip.

18. The method of claim 17, wherein said displacement pulses are substantially synchronized with motion of said tip and/or said target.

19. The method of claim 17, wherein said method further comprises providing electric field pulses.

20. The method of claim 19, wherein said field pulses are substantially synchronized with said displacement pulses.

21. The method of claim 19, wherein said field pulses and said displacement pulses are offset by a phase lag or lead.

22. The method of claim 19, wherein said field pulses and said displacement pulses are substantially synchronized with motion of said tip and/or said target.

23. The method of claim 19, wherein said pulses are variable in pulse time and magnitude.

24. The method of claim 1, wherein said method further comprises providing an array of tips.

25. The method of claim 24, wherein adjacent tips are spaced by at least 2 mm.

26. The method of claim 1, wherein said method further comprises pressurizing a reservoir containing said liquid to be dispensed to a degassing high first pressure by providing a static pressure from a helium source over said liquid to degas said liquid.

27. The method of claim 26, wherein said method further comprises reducing said first pressure in said reservoir to a low second pressure.

28. The method of claim 27, wherein said method further comprises venting said reservoir to ambient conditions.

29. The method of claim 27, wherein said method further comprises operating a pump connected to said reservoir to draw said liquid from said reservoir into said pump.

30. The method of claim 1, wherein said tip has a first conduit and a second conduit having a drop emitting orifice with said conduits being angled with respect to one another.

31. The method of claim 30, wherein said tip comprises a shaped surface proximate to a junction between said conduits to direct said liquid from said first conduit towards said orifice.

32. The method of claim 31, wherein said first conduit and said second conduit are substantially perpendicular to one another.

33. The method of claim 32, wherein said shaped surface comprises a substantially uniform bevel.

34. The method of claim 33, wherein said bevel is angled relative to said first and said second conduits by an angle substantially equal to half the angle between said first and said second conduits.

35. The method of claim 32, wherein said shaped surface comprises a contoured and/or curved surface.

36. The method of claim 1, wherein said method further comprises providing an elastic element in the fluid path.

37. The method of claim 1, wherein said method further comprises providing a constrictor in the fluid path.

38. The method of claim 1, wherein said method further comprises providing a dampener in the fluid path.

39. The method of claim 1, wherein said liquid comprises a reagent.

40. A method of accurately dispensing sub-microfluidic droplets of a liquid onto or into a target supported on a table, comprising:
   providing a dispensing system comprising a substantially inert fluid path and a dispensing tip having a nozzle and a droplet emitting orifice at a distal end;
   generating an electric field between said tip and said table by maintaining said tip at a first potential and said table at a second potential;
   positively displacing said liquid through said tip to dispense droplets onto or into said target with said electric field providing a bias that facilitates droplet ejection and release from said tip so that droplets having a volume of less than about one microliter are reliably dispensed; and
   maintaining a voltage difference between said nozzle and said liquid therein;
   wherein said nozzle has an outer surface coated with a conductive layer except for a portion at said distal end of said tip.

41. The method of claim 40, wherein said electric field provides a gradient substantially parallel to the intended droplet trajectory.

42. The method of claim 40, wherein said method further comprises providing a ring electrode at a third potential and positioned intermediate said tip and said target and/or table.

43. The method of claim 42, wherein said method further comprises adjusting said first, second and third potentials to control droplet impact velocity on said target.

44. The method of claim 42, wherein said first and said second potentials are substantially the same while said third potential is lower so that droplet impact velocity is substantially a function of ejection velocity.

45. The method of claim 42, wherein said first potential is lower than said second potentials while said third potential is lower than both so that droplet impact velocity is reduced compared to that without any electric field.

46. The method of claim 42, wherein said ring electrode is integrated with said tip.

47. The method of claim 42, wherein said ring electrode is movable from under said tip.

48. The method of claim 40, wherein said electric field perturbs the fluid meniscus at said orifice to form a Taylor cone and said method further comprises applying a superimposed positive displacement pulse to aid in ejection of said droplets from said orifice.

49. The method of claim 40, wherein said liquid comprises a reagent.

50. The method of claim 40, wherein said method further comprises controlling the surface charge on said target.

51. The method of claim 40, wherein a hydraulic source positively displaces said liquid.

52. The method of claim 40, wherein a pneumatic source positively displaces said liquid.

53. The method of claim 40, wherein said droplets have a volume less than about 100 nanoliters.

54. The method of claim 40, wherein said electric field is in the range from about 0.5 kV to about 5 kV.

55. The method of claim 40, wherein positive displacement pulses provide said liquid to said tip.

56. The method of claim 55, wherein said displacement pulses are substantially synchronized with motion of said tip and/or said target.

57. The method of claim 55, wherein said method further comprises providing electric field pulses.

58. The method of claim 57, wherein said field pulses are substantially synchronized with said displacement pulses.

59. The method of claim 57, wherein said field pulses and said displacement pulses are offset by a phase lag or lead.

60. The method of claim 57, wherein said field pulses and said displacement pulses are substantially synchronized with motion of said tip and/or said target.

61. The method of claim 57, wherein said pulses are variable in pulse time and magnitude.

62. The method of claim 40, wherein said method further comprises providing an array of tips.

63. The method of claim 62, wherein adjacent tips are spaced by at least 2mm.

64. The method of claim 40, wherein said method further comprises pressurizing a reservoir containing said liquid to be dispensed to a degassing high first pressure by providing a static pressure from a helium source over said liquid to degas said liquid.

65. The method of claim 64, wherein said method further comprises reducing said first pressure in said reservoir to a low second pressure.

66. The method of claim 65, wherein said method further comprises venting said reservoir to ambient conditions.

67. The method of claim 65, wherein said method further comprises operating a pump connected to said reservoir to draw said liquid from said reservoir into said pump.

68. The method of claim 40, wherein said tip has a first conduit and a second conduit having a drop emitting orifice with said conduits being angled with respect to one another.

69. The method of claim 68, wherein said tip comprises a shaped surface proximate to a junction between said conduits to direct said liquid from said first conduit towards said orifice.

70. The method of claim 69, wherein said first conduit and said second conduit are substantially perpendicular to one another.

71. The method of claim 70, wherein said shaped surface comprises a substantially uniform bevel.

72. The method of claim 71, wherein said bevel is angled relative to said first and said second conduits by an angle substantially equal to half the angle between said first and said second conduits.

73. The method of claim 70, wherein said shaped surface comprises a contoured and/or curved surface.

74. The method of claim 40, wherein said method further comprises providing an elastic element in the fluid path.

75. The method of claim 40, wherein said method further comprises providing a constrictor in the fluid path.

76. The method of claim 40, wherein said method further comprises providing a dampener in the fluid path.

* * * * *

UNITED STATES PATENT AND TRADEMARK OFFICE
CERTIFICATE OF CORRECTION

PATENT NO.       : 7,470,547 B2
APPLICATION NO.  : 10/909934
DATED            : December 30, 2008
INVENTOR(S)      : Tisone et al.

Page 1 of 1

It is certified that error appears in the above-identified patent and that said Letters Patent is hereby corrected as shown below:

At column 10, line 2, change "can," to --can--.

At column 17, line 48, change "field)" to --field--.

At column 24, line 1, change "retained," to --retained--.

At column 27, line 28, change "functional." to --functional--.

At column 32, line 63, change "are" to --are,--.

At column 33, line 7, change "electromechanical" to --electro-mechanical--.

Signed and Sealed this

Second Day of June, 2009

JOHN DOLL
*Acting Director of the United States Patent and Trademark Office*